US012714107B2

(12) United States Patent
Zimmermann et al.

(10) Patent No.: US 12,714,107 B2
(45) Date of Patent: Aug. 25, 2026

(54) DIOXAZOLINES AND THEIR USE AS HERBICIDES

(71) Applicant: BASF SE, Ludwigshafen (DE)

(72) Inventors: Gunther Zimmermann, Ludwigshafen (DE); Markus Kordes, Ludwigshafen (DE); Tobias Seiser, Ludwigshafen (DE); Trevor William Newton, Limburgerhof (DE); Gerd Kraemer, Limburgerhof (DE); Thomas Seitz, Ludwigshafen (DE); Aimone Porri, Limburgerhof (DE); Ruth Campe, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 528 days.

(21) Appl. No.: 17/913,262

(22) PCT Filed: Mar. 18, 2021

(86) PCT No.: PCT/EP2021/056897
§ 371 (c)(1),
(2) Date: Sep. 21, 2022

(87) PCT Pub. No.: WO2021/191035
PCT Pub. Date: Sep. 30, 2021

(65) Prior Publication Data

US 2023/0148603 A1 May 18, 2023

(30) Foreign Application Priority Data

Mar. 25, 2020 (EP) .................................... 20165514

(51) Int. Cl.
*A01N 43/82* (2006.01)
*A01P 13/02* (2006.01)
*C07D 273/01* (2006.01)

(52) U.S. Cl.
CPC .............. *A01N 43/82* (2013.01); *A01P 13/02* (2021.08); *C07D 273/01* (2013.01)

(58) Field of Classification Search
None
See application file for complete search history.

(56) References Cited

U.S. PATENT DOCUMENTS

| | | | |
|---|---|---|---|
| 3,809,763 A | 5/1974 | Sasse et al. | |
| 5,591,695 A | 1/1997 | Newton | |
| 7,232,792 B2 | 6/2007 | von Deyn et al. | |
| 2014/0100108 A1* | 4/2014 | Willms .................. | A01N 43/56 504/105 |

FOREIGN PATENT DOCUMENTS

| | | | |
|---|---|---|---|
| CN | 1134935 | A | 11/1996 |
| EP | 0647635 | A1 | 4/1995 |
| EP | 0726263 | A2 | 8/1996 |
| WO | WO-98/31681 | A1 | 7/1998 |
| WO | WO-2012/130798 | A1 | 10/2012 |
| WO | WO-2014/048882 | A1 | 4/2014 |
| WO | WO-2018/228985 | A1 | 12/2018 |
| WO | WO-2018/228986 | A1 | 12/2018 |
| WO | WO-2019/034602 | A1 | 2/2019 |
| WO | WO-2019/145245 | A1 | 8/2019 |

OTHER PUBLICATIONS

Koyanagi (Ch. 2: Bioisosterism in Agrochemicals, 1995, from Baker et al. Syn. and Chem. of Agrochemicals IV, p. 1-24).*

US20140100108 to Willms et al., megatable relevant pages, 2 pg. 2014, from https://seqdata.uspto.gov/?pageRequest=docDetail &DocID=US20140100108A1.*

Barillari et al., Classical bioisosteres: Brown:Bioisosteres Med CHO-BK, In: Bioisosteres in Medicinal Chemistry: Brown:Bioisosteres Med CHO-BK, Wiley-VCH Verlag GMBH& Co KGAA, pp. 15-29 (Aug. 2012).

European Search Report for EP Patent Application No. 20165514.9, Issued on Jul. 24, 2020, 5 pages.

Huisgen et al., 1.3-Dipolare cycloadditionen, 66. 1.3.4-dioxazole aus nitriloxiden und carbonylverbindungen, Chemische Berichte, 105(9):2805-13 (Sep. 1972).

International Application No. PCT/EP2021/056897, International Search Report and Written Opinion, mailed Jun. 28, 2021.

* cited by examiner

*Primary Examiner* — Erin E Hirt
(74) *Attorney, Agent, or Firm* — MARSHALL, GERSTEIN & BORUN LLP

(57) ABSTRACT

The invention relates to compounds of formula (I), (I) and their use as herbicides. In said formula, $R^1$ to $R^7$ represent groups such as hydrogen, halo-gen or organic groups such as alkyl, alkenyl, alkynyl, or alkoxy; X is a bond or a divalent unit; Y is hydrogen, cyano, hydroxyl or a linear or cyclic organic group. The invention further refers to a composition comprising such compound and to the use thereof for controlling unwanted vegetation.

(I)

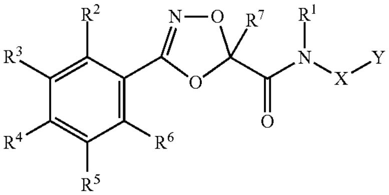

9 Claims, No Drawings

DIOXAZOLINES AND THEIR USE AS HERBICIDES

CROSS-REFERENCE TO RELATED APPLICATIONS

This is the U.S. national phase of International Application No. PCT/EP2021/056897, filed Mar. 18, 2021, which claims the benefit of European Patent Application No. 20165514.9, filed on Mar. 25, 2020.

The present invention relates to Dioxazoline compounds and compositions comprising the same. The invention also relates to the use of the Dioxazoline compounds or the corresponding compositions for controlling unwanted vegetation. Furthermore, the invention relates to methods of applying the Dioxazoline compounds or the corresponding compositions.

For the purpose of controlling unwanted vegetation, especially in crops, there is an ongoing need for new herbicides that have high activity and selectivity together with a substantial lack of toxicity for humans and animals.

WO12130798, WO1404882, WO14048882, WO18228985, WO18228986, WO19034602, and WO19145245 describe 3-phenylisoxazoline-5-carboxamides and their use as herbicides.

The compounds of the prior art often suffer from insufficient herbicidal activity, in particular at low application rates, and/or unsatisfactory selectivity resulting in a low compatibility with crop plants.

Accordingly, it is an object of the present invention to provide compounds having a strong herbicidal activity, in particular even at low application rates, a sufficiently low toxicity for humans and animals and/or a high compatibility with crop plants. The Dioxazoline compounds should also show a broad activity spectrum against a large number of different unwanted plants.

These and further objectives are achieved by the compounds of formula (I) defined below including their agriculturally acceptable salts, amides, esters or thioesters.

Accordingly, the present invention provides compounds of formula (I)

(I)

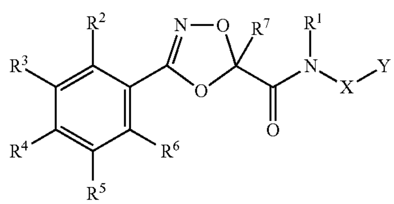

wherein the substituents have the following meanings:

$R^1$ hydrogen, $(C_1-C_3)$-alkyl, $(C_3-C_4)$-cycloalkyl, $(C_1-C_3)$-haloalkyl, $(C_2-C_3)$-alkenyl, $(C_2-C_3)$-haloalkenyl, $(C_2-C_3)$-alkynyl, $(C_2-C_3)$-haloalkynyl, $(C_1-C_3)$-alkoxy-$(C_1-C_3)$-alkyl, $(C_1-C_3)$-alkoxy, $(C_1-C_3)$-haloalkoxy, $(C_1-C_3)$-alkoxy-$(C_1-C_3)$-alkoxy;

$R^2$ hydrogen, halogen, hydroxyl, cyano, $(C_1-C_3)$-alkyl, $(C_1-C_3)$-haloalkyl, $(C_1-C_3)$-alkoxy, $(C_1-C_3)$-haloalkoxy;

$R^3$ hydrogen, halogen, nitro, hydroxyl, cyano, $(C_1-C_3)$-alkyl, $(C_1-C_3)$-haloalkyl, hydroxy-$(C_1-C_3)$-alkyl, $(C_3-C_5)$-cycloalkyl, $(C_3-C_5)$-halocycloalkyl, hydroxy-$(C_3-C_5)$-cycloalkyl, $(C_1-C_3)$-alkoxy, $(C_1-C_3)$-haloalkoxy, $(C_1-C_3)$-alkoxycarbonyl, $(C_2-C_3)$-alkenyl, $(C_2-C_3)$-haloalkenyl, $(C_2-C_3)$-alkynyl, $(C_2-C_3)$-haloalkynyl, $(C_1-C_3)$-alkylthio, $(C_1-C_3)$-alkylsulfinyl, $(C_1-C_3)$-alkylsulfonyl;

$R^4$ hydrogen, halogen, hydroxyl, cyano, $(C_1-C_3)$-alkyl, $(C_1-C_3)$-haloalkyl, $(C_3-C_4)$-halocycloalkyl, $(C_1-C_3)$-alkoxy, $(C_1-C_3)$-haloalkoxy, $(C_2-C_3)$-haloalkenyl, $(C_2-C_3)$-haloalkynyl, $(C_1-C_3)$-alkylthio;

$R^5$ hydrogen, halogen, nitro, hydroxyl, cyano, $(C_1-C_3)$-alkyl, $(C_1-C_3)$-haloalkyl, hydroxy-$(C_1-C_3)$-alkyl, $(C_3-C_5)$-cycloalkyl, $(C_3-C_5)$-halocycloalkyl, hydroxy-$(C_3-C_5)$-cycloalkyl, $(C_1-C_3)$-alkoxy, $(C_1-C_3)$-haloalkoxy, $(C_1-C_3)$-alkoxycarbonyl, $(C_2-C_3)$-alkenyl, $(C_2-C_3)$-haloalkenyl, $(C_2-C_3)$-alkynyl, $(C_2-C_3)$-haloalkynyl, $(C_1-C_3)$-alkylthio, $(C_1-C_3)$-alkylsulfinyl, $(C_1-C_3)$-alkylsulfonyl;

$R^6$ hydrogen, halogen, hydroxyl, cyano, $(C_1-C_3)$-alkyl, $(C_1-C_3)$-haloalkyl, $(C_1-C_3)$-alkoxy, $(C_1-C_3)$-haloalkoxy;

$R^7$ fluorine, cyano, or $(C_1-C_6)$-alkyl, $(C_3-C_6)$-cycloalkyl, $(C_2-C_6)$-alkenyl, $(C_2-C_6)$-alkynyl, $(C_1-C_6)$-alkoxy, each substituted by m radicals from the group consisting of fluorine, chlorine, bromine, iodine, hydroxyl, cyano and $(C_1-C_6)$-alkoxy;

X a bond ($X^0$) or a divalent unit from the group consisting of ($X^1$), ($X^2$), ($X^3$), ($X^4$), ($X^5$), and ($X^6$):

($X^1$)

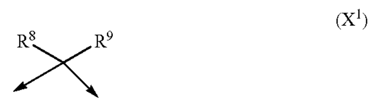

($X^2$)

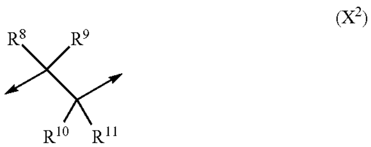

($X^3$)

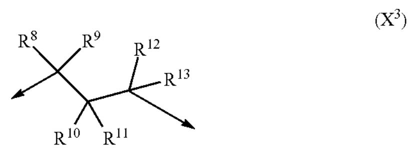

($X^4$)

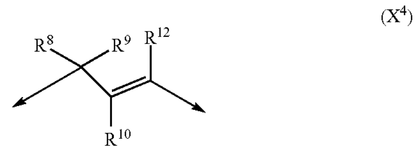

($X^5$)

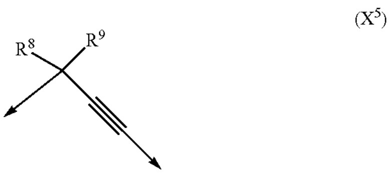

($X^6$)

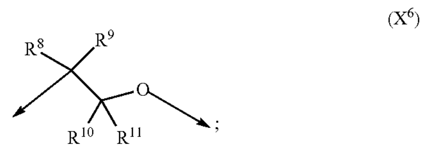

;

$R^8$-$R^{13}$ each independently hydrogen, fluorine, chlorine, bromine, iodine, hydroxyl, cyano, $CO_2R^e$, $CONR^bR^d$, $NR^bCO_2R^e$, $R^a$, or $(C_1-C_6)$-alkyl, $(C_3-C_5)$-cycloalkyl, $(C_2-C_6)$-alkenyl, $(C_2-C_6)$-alkynyl, each substituted by m radicals from the group consisting of fluorine, chlorine, bromine, iodine, hydroxyl and cyano, or $(C_1-C_6)$-alkoxy, $(C_3-C_6)$-cycloalkoxy, $(C_3-C_6)$-alkenyloxy, $(C_3-C_6)$-alkynyloxy, $(C_1-C_3)$-alkylthio, $(C_1-C_3)$-alkylsulfinyl, $(C_1-C_3)$-alkylsulfonyl, each substituted by m radicals from the group consisting of fluorine, chlorine, bromine, iodine, cyano and $(C_1-C_2)$-alkoxy;

Y hydrogen, cyano, hydroxyl, Z, or $(C_1-C_{12})$-alkyl, $(C_3-C_8)$-cycloalkyl, $(C_2-C_{12})$-alkenyl or $(C_2-C_{12})$-alkynyl, each substituted by m radicals from the group consisting of fluorine, chlorine, bromine, iodine, cyano, hydroxyl, $OR^d$, Z, OZ, NHZ, $S(O)_nR^a$, $SO_2NR^bR^d$, $SO_2NR^bCOR^e$, $CO_2R^e$, $CONR^bR^h$, $COR^b$, $CONR^eSO_2R^a$, $NR^bR^e$, $NR^b$-$COR^e$, $NR^bCONR^eR^e$, $NR^bCO_2R^e$, $NR^bSO_2R^e$ $NR^bSO_2NR^bR^e$, $OCONR^bR^e$, $OCSNR^bR^e$, $POR^fR^f$ and $C(R^b)$=$NOR^e$;

Z a three-, four-, five- or six-membered saturated, partly unsaturated, fully unsaturated or aromatic ring, except phenyl, which is formed from r carbon atoms, n nitrogen atoms, n sulfur atoms and n oxygen atoms, and which is substituted by m radicals from the group consisting of $CO_2R^e$, $CONR^bR^h$, $S(O)_nR^a$, $SO_2NR^bR^d$, $SO_2NR^bCOR^e$, $COR^b$, $CONR^eSO_2R^a$, $NR^bR^e$, $NR^b$-$COR^e$, $NR^bCONR^eR^e$, $NR^bCO_2R^e$, $NR^bSO_2R^e$, $NR^bSO_2NR^bR^e$, $OCONR^bR^e$, $OCSNR^bR^e$, $POR^fR^f$ and $C(R^b)$=$NOR^e$, $R^b$, $R^c$, $R^e$ and $R^f$, and where the sulfur atoms and carbon atoms bear n oxo groups;

$R^a$ $(C_1-C_6)$-alkyl or $(C_3-C_6)$-cycloalkyl, each of which is substituted by m radicals selected from the group consisting of fluorine, chlorine, bromine, iodine, cyano, hydroxy, and $(C_1-C_3)$-alkoxy;

$R^b$ hydrogen, $(C_1-C_3)$-alkoxy or $R^a$;

$R^c$ fluorine, chlorine, bromine, iodine, cyano, hydroxyl, $S(O)_nR^a$ or $(C_1-C_6)$-alkoxy, $(C_3-C_6)$-alkenyloxy or $(C_3-C_6)$-alkynyloxy, each of which is substituted by m radicals selected from the group consisting of fluorine, chlorine, bromine, cyano and $(C_1-C_2)$-alkoxy;

$R^d$ hydrogen or $(C_1-C_6)$-alkyl, $(C_3-C_6)$-cycloalkyl, $(C_2-C_4)$-alkenyl, $(C_3-C_6)$-cycloalkyl-$(C_1-C_3)$-alkyl, phenyl-$(C_1-C_3)$-alkyl, furanyl-$(C_1-C_3)$-alkyl or $(C_2-C_4)$-alkynyl, each of which is substituted by m radicals selected from the group consisting of fluorine, chlorine, bromine, cyano, $CO_2R^a$, $CONR^bR^h$, $(C_1-C_2)$-alkoxy, $(C_1-C_3)$-alkylthio, $(C_1-C_3)$-alkylsulfinyl, $(C_1-C_3)$-alkylsulfonyl, phenylthio, phenylsulfinyl, and phenylsulfonyl;

$R^e$ $R^d$.

$R^f$ $(C_1-C_3)$-alkyl or $(C_1-C_3)$-alkoxy;

$R^h$ hydrogen or $(C_1-C_6)$-alkyl, $(C_1-C_2)$-alkoxy, $(C_3-C_6)$-cycloalkyl, $(C_2-C_4)$-alkenyl, $(C_1-C_6)$-alkoxycarbonyl-$(C_1-C_6)$-alkyl, or $(C_2-C_4)$-alkynyl, each of which is substituted by m radicals selected from the group consisting of fluorine, chlorine, bromine, cyano, $CO_2R^a$ and $(C_1-C_2)$-alkoxy;

m 0, 1, 2, 3, 4 or 5;

n 0, 1 or 2;

r 1, 2, 3, 4, 5 or 6;

including their agriculturally acceptable salts, amides, esters or thioesters, provided the compounds of formula (I) have a carboxyl group; with the exception of 5-methyl-3-phenyl-1,4,2-dioxazole-5-carboxamide.

The present invention also provides formulations comprising at least one compound of formula (I) and auxiliaries customary for formulating crop protection agents.

The present invention also provides combinations comprising at least one compound of formula (I) (component A) and at least one further compound selected from the herbicidal compounds B (component B) and safeners C (component C).

The present invention also provides the use of compounds of formula (I) as herbicides, i.e. for controlling undesired vegetation.

The present invention furthermore provides a method for controlling undesired vegetation where a herbicidal effective amount of at least one compound of formula (I) is allowed to act on plants, their seeds and/or their habitat.

If the compounds of formula (I), the herbicidal compounds B and/or the safeners C as described herein are capable of forming geometric isomers, for example E/Z isomers, it is possible to use both, the pure isomers and mixtures thereof, according to the invention.

If the compounds of formula (I), the herbicidal compounds B and/or the safeners C as described herein have one or more centres of chirality and, as a consequence, are present as enantiomers or diastereomers, it is possible to use both, the pure enantiomers and diastereomers and their mixtures, according to the invention.

If the compounds of formula (I), the herbicidal compounds B and/or the safeners C as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diethylammonium, diisopropylammonium, trimethylammonium, triethylammonium, tris (isopropyl)ammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri ($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Compounds of formula (I), herbicidal compounds B and/or safeners C as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides.

Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

The terms used for organic groups in the definition of the variables are, for example the expression "halogen", collective terms which represent the individual members of these groups of organic units.

The prefix $C_x$-$C_y$ denotes the number of possible carbon atoms in the particular case. All hydrocarbon chains can be straight-chain or branched.

halogen: fluorine, chlorine, bromine, or iodine, especially fluorine, chlorine or bromine; alkyl and the alkyl moieties of composite groups such as, for example, alkoxy, alkylamino, alkoxycarbonyl: saturated straight-chain or branched hydrocarbon radicals having 1 to 10 carbon atoms, for example $C_1$-$C_{10}$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; heptyl, octyl, 2-ethylhexyl and positional isomers thereof; nonyl, decyl and positional isomers thereof;

haloalkyl: straight-chain or branched alkyl groups having 1 to 10 carbon atoms (as mentioned above), where some or all of the hydrogen atoms in these groups are replaced by halogen atoms as mentioned above. In one embodiment, the alkyl groups are substituted at least once or completely by a particular halogen atom, preferably fluorine, chlorine or bromine. In a further embodiment, the alkyl groups are partially or fully halogenated by different halogen atoms; in the case of mixed halogen substitutions, the combination of chlorine and fluorine is preferred. Particular preference is given to ($C_1$-$C_3$)-haloalkyl, more preferably ($C_1$-$C_2$)-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl and also the alkenyl moieties in composite groups, such as alkenyloxy: unsaturated straight-chain or branched hydrocarbon radicals having 2 to 10 carbon atoms and one double bond in any position. According to the invention, it may be preferred to use small alkenyl groups, such as ($C_2$-$C_4$)-alkenyl; on the other hand, it may also be preferred to employ larger alkenyl groups, such as ($C_5$-$C_8$)-alkenyl. Examples of alkenyl groups are, for example, $C_2$-$C_5$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

haloalkenyl: alkenyl groups as mentioned above which are partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl; alkynyl and the alkynyl moieties in composite groups, such as alkynyloxy: straight-chain or branched hydrocarbon groups having 2 to 10 carbon atoms and one or two triple bonds in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl; haloalkynyl: alkynyl groups as mentioned above which are partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

cycloalkyl and also the cycloalkyl moieties in composite groups: mono- or bicyclic saturated hydrocarbon groups having 3 to 10, in particular 3 to 6, carbon ring members, for example $C_3$-$C_6$-cycloalkyl, such as cyclopropyl, cyclobutyl, cyclopentyl, cyclohexyl, cycloheptyl or cyclooctyl. Examples of bicyclic radicals comprise bicyclo[2.2.1]heptyl, bicyclo[3.1.1]heptyl, bicyclo[2.2.2]octyl and bicyclo[3.2.1]octyl. In this connection, optionally substituted $C_3$—C— cycloalkyl means a cycloalkyl radical having from 3 to 8 carbon atoms, in which at least one hydrogen atom, for example 1, 2, 3, 4 or 5 hydrogen atoms, is/are replaced by substituents which are inert under the conditions of the reaction. Examples of inert substituents are CN, $C_1$-$C_6$-alkyl, $C_1$-$C_4$-haloalkyl, $C_1$-$C_6$-alkoxy, $C_3$-$C_6$-cycloalkyl, and $C_1$-$C_4$-alkoxy-$C_1$-$C_6$-alkyl; halocycloalkyl and the halocycloalkyl moieties in halocycloalkoxy, halocycloalkylcarbonyl and the like: monocyclic saturated hydrocarbon groups having 3 to 10 carbon ring members (as mentioned above) in which some or all of the hydrogen atoms may be replaced by halogen atoms as mentioned above, in particular fluorine, chlorine and bromine;

cycloalkoxy: cycloalkyl groups as mentioned above which are attached via an oxygen; alkoxy and also the alkoxy moieties in composite groups, such as alkoxyalkyl: an alkyl group as defined above which is attached via an oxygen, preferably having 1 to 10, more preferably 2 to 6, carbon atoms. Examples are: methoxy, ethoxy, n-propoxy, 1-methylethoxy, butoxy, 1-methylpropoxy, 2-methylpropoxy or 1,1-dimethylethoxy, and also for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy; haloalkoxy: alkoxy as defined above, where some or all of the hydrogen atoms in these groups are replaced by halogen atoms as described above under haloalkyl, in particular by fluorine, chlorine or bromine. Examples are $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy; and also 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

alkylthio: an alkyl group as defined above, which is attached via a sulfur atom preferably having 1 to 6, more preferably 1 to 3, carbon atoms.

alkylsulfinyl: an alkyl group as defined above, which is attached via S(O), preferably having 1 to 6, more preferably 1 to 3, carbon atoms.

alkysulfonyl: an alkyl group as defined above, which is attached via $S(O)_2$, preferably having 1 to 6, more preferably 1 to 3, carbon atoms.

hydroxyl: OH group which is attached via an O atom;

cyano: CN group which is attached via an C atom;

nitro: $NO_2$ group which is attached via an N atom.

The preferred embodiments of the invention mentioned herein below have to be understood as being preferred either independently from each other or in combination with one another.

According to particular embodiments of the invention, preference is given to those compounds of formula (I) wherein the variables, either independently of one another or in combination with one another, have the following meanings:

Preferred compounds according to the invention are compounds of formula (I), wherein $R^1$ is selected from the group consisting of hydrogen, ($C_1$-$C_3$)-alkyl, ($C_3$-$C_4$)-cycloalkyl, ($C_1$-$C_3$)-haloalkyl, ($C_2$-$C_3$)-alkenyl, ($C_2$-$C_3$)-alkynyl, ($C_1$-$C_3$)-alkoxy-($C_1$-$C_3$)-alkyl, ($C_1$-$C_3$)-alkoxy.

More preferred compounds according to the invention are compounds of formula (I), wherein $R^1$ is selected from the group consisting of hydrogen, ($C_1$-$C_3$)-alkyl, ($C_3$-$C_4$)-cycloalkyl, and ($C_1$-$C_3$)-alkoxy-($C_1$-$C_3$)-alkyl.

Also preferred compounds according to the invention are compounds of formula (I), wherein $R^1$ is selected from the group consisting of hydrogen, methyl, and methoxymethyl.

In particular, $R^1$ is hydrogen.

Further preferred compounds according to the invention are compounds of formula (I), wherein $R^2$ is selected from the group consisting of hydrogen, halogen and ($C_1$-$C_3$)-alkyl.

Also preferred compounds according to the invention are compounds of formula (I), wherein $R^2$ is selected from the group consisting of hydrogen, fluorine, chlorine and methyl.

In particular, $R^2$ is hydrogen.

Further preferred compounds according to the invention are compounds of formula (I), wherein $R^3$ is selected from the group consisting of hydrogen, halogen, hydroxyl, cyano, ($C_1$-$C_3$)-alkyl, ($C_1$-$C_3$)-haloalkyl, and ($C_1$-$C_3$)-haloalkoxy.

More preferred compounds according to the invention are compounds of formula (I), wherein $R^3$ is selected from the group consisting of halogen, cyano, and ($C_1$-$C_3$)-alkyl.

Also preferred compounds according to the invention are compounds of formula (I), wherein $R^3$ is selected from the group consisting of hydrogen, halogen, hydroxyl, cyano, methyl, trifluoromethyl and trifluoromethoxy.

In particular, $R^3$ is hydrogen or halogen, very particular chlorine or fluorine.

Further preferred compounds according to the invention are compounds of formula (I), wherein $R^4$ is selected from the group consisting of hydrogen and halogen.

Also preferred compounds according to the invention are compounds of formula (I), wherein $R^4$ is selected from the group consisting of hydrogen, fluorine, chlorine and bromine.

In particular, $R^4$ is hydrogen or hydrogen, fluorine or chlorine, very particular hydrogen.

Further preferred compounds according to the invention are compounds of formula (I), wherein $R^5$ is selected from the group consisting of hydrogen, halogen, hydroxyl, cyano, $(C_1-C_3)$-alkyl, $(C_1-C_3)$-haloalkyl, and $(C_1-C_3)$-haloalkoxy.

More preferred compounds according to the invention are compounds of formula (I), wherein $R^5$ is selected from the group consisting of halogen, cyano, and $(C_1-C_3)$-alkyl.

Also preferred compounds according to the invention are compounds of formula (I), wherein $R^5$ is selected from the group consisting of hydrogen, halogen, hydroxyl, cyano, methyl, trifluoromethyl and trifluoromethoxy.

In particular, $R^5$ is hydrogen or halogen, very particular chlorine or fluorine.

Further preferred compounds according to the invention are compounds of formula (I), wherein $R^3$ and $R^5$ are selected from the group consisting of hydrogen, halogen, hydroxyl, cyano and $(C_1-C_3)$-alkyl, and wherein at least one of $R^3$ and $R^5$ is not hydrogen.

Further preferred compounds according to the invention are compounds of formula (I), wherein $R^6$ is selected from the group consisting of hydrogen, halogen and $(C_1-C_3)$-alkyl.

Also preferred compounds according to the invention are compounds of formula (I), wherein $R^6$ is selected from the group consisting of hydrogen, fluorine, chlorine and methyl.

In particular, $R^6$ is hydrogen.

Further preferred compounds according to the invention are compounds of formula (I), wherein $R^7$ is selected from the group consisting of $(C_1-C_3)$-alkyl, $(C_3-C_4)$-cycloalkyl, $(C_2-C_3)$-alkenyl, and $(C_1-C_3)$-alkoxy, each substituted by m radicals from the group consisting of fluorine, chlorine, and $(C_1-C_2)$-alkoxy. In this context, m is preferably 0, 1, 2, or 3.

Also preferred compounds according to the invention are compounds of formula (I), wherein $R^7$ is selected from the group consisting of $(C_1-C_2)$-alkyl, cyclopropyl, $(C_1-C_2)$-haloalkyl, $(C_2-C_3)$-alkenyl, and $(C_1-C_2)$-alkoxy.

In particular, $R^7$ is methyl, chloromethyl, trifluoromethyl, cyclopropyl, ethenyl, and methoxy, very particular methyl.

In the compounds of formula (I), X is selected from the group consisting of a bond ($X^0$) or a divalent unit from the group consisting of ($X^1$), ($X^2$), ($X^3$), ($X^4$), ($X^5$) and ($X^6$), wherein the orientation of ($X^1$), ($X^2$), ($X^3$), ($X^4$), ($X^5$) and ($X^6$) within the molecule is as depicted, the left arrow representating the bond to the adjacent nitrogen, the right arrow representating the bond to the adjacent group Y.

($X^1$)

($X^2$)

($X^3$)

($X^4$)

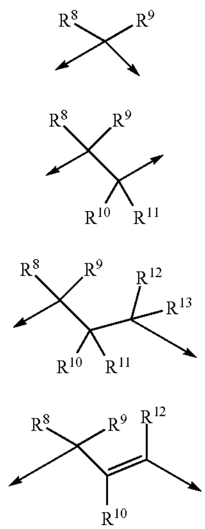

-continued ($X^5$)

($X^6$)

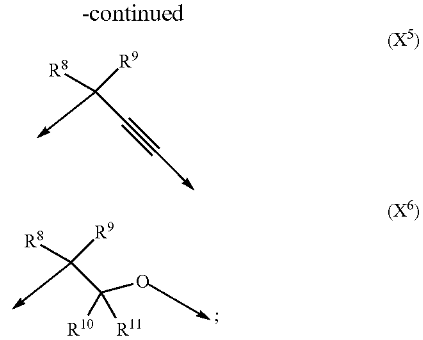

In a preferred embodiment (compounds of formula ($I.X^0$)), X is a bond ($X^0$):

($I.X^0$)

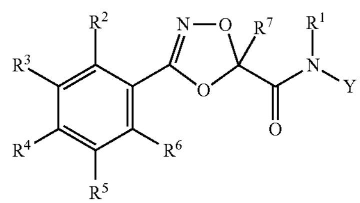

In another preferred embodiment (compounds of formula ($I.X^1$)), X is ($X^1$), wherein the orientation of ($X^1$) within the molecule is as depicted, the left arrow representating the bond to the adjacent nitrogen, the right arrow representating the bond to the adjacent group Y:

($I.X^1$)

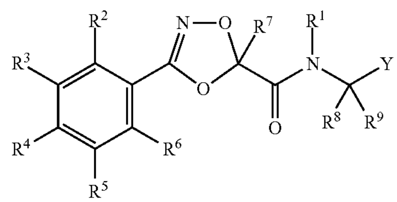

In another preferred embodiment (compounds of formula ($I.X^2$)), X is ($X^2$), wherein the orientation of ($X^2$) within the molecule is as depicted, the left arrow representating the bond to the adjacent nitrogen, the right arrow representating the bond to the adjacent group Y:

($I.X^2$)

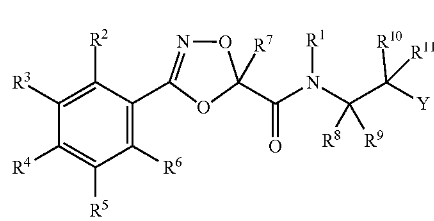

In another preferred embodiment (compounds of formula ($I.X^3$)), X is ($X^3$), wherein the orientation of ($X^3$) within the molecule is as depicted, the left arrow representating the bond to the adjacent nitrogen, the right arrow representating the bond to the adjacent group Y:

(I.X$^3$)

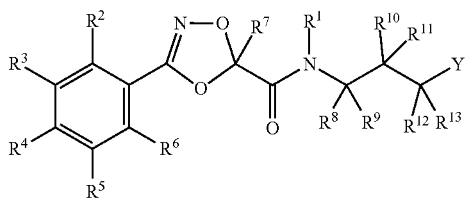

In another preferred embodiment (compounds of formula (I.X$^4$)), X is (X$^4$), wherein the orientation of (X$^4$) within the molecule is as depicted, the left arrow representating the bond to the adjacent nitrogen, the right arrow representating the bond to the adjacent group Y:

(I.X$^4$)

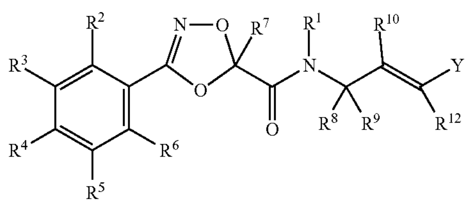

In another preferred embodiment (compounds of formula (I.X$^5$)), X is (X$^5$), wherein the orientation of (X$^5$) within the molecule is as depicted, the left arrow representating the bond to the adjacent nitrogen, the right arrow representating the bond to the adjacent group Y:

(I.X$^5$)

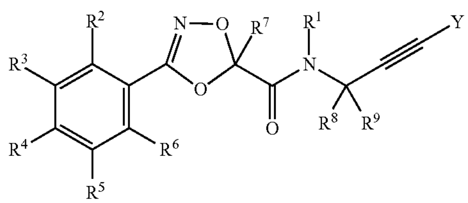

In another preferred embodiment (compounds of formula (I.X$^6$)), X is (X$^6$), wherein the orientation of (X$^6$) within the molecule is as depicted, the left arrow representating the bond to the adjacent nitrogen, the right arrow representating the bond to the adjacent group Y:

(I.X$^6$)

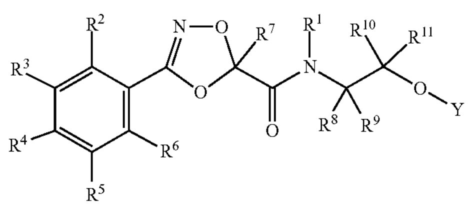

Further preferred compounds according to the invention are compounds of formula (I), wherein X is selected from the group consisting of a bond (X$^0$) or a divalent unit from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, C(iPr)$CH_3$, $CH(CH_2$iPr)$CH_2$, $CH_2CH{=}CH$, $C(CH_3)_2C{=}C$, $CH(CF_3)CH_2$, $CH(CH_3)CH_2O$, $CH_2CH_2O$, CH(cPr)$CH_2O$, $CH(CH_2OCH_3)$, $CH(CH_2CH_2SCH_3)$, CH(COOH), $CH(COOCH_3)$, CH(COOH)$CH_2$, $CH(COOCH_3)CH_2$, $CH_2COH(CF_3)$, $CH(CONHCH_3)$, $CH(CONHCH_3)CH_2$ and $CH_2CH_2CONHCH_2$.

Further preferred compounds according to the invention are compounds of formula (I), wherein R$^8$-R$^{13}$ each independently is selected from the group consisting of hydrogen, fluorine, chlorine, bromine, iodine, hydroxyl, cyano, $CO_2R^e$, $CONR^bR^d$, or ($C_1$-$C_6$)-alkyl, ($C_3$-$C_5$)-cycloalkyl, ($C_2$-$C_6$)-alkenyl, each substituted by m radicals from the group consisting of fluorine, or ($C_1$-$C_6$)-alkoxy, ($C_3$-$C_6$)-cycloalkoxy, ($C_3$-$C_6$)-alkenyloxy, ($C_3$-$C_6$)-alkynyloxy, ($C_1$-$C_3$)-alkylsulfinyl, ($C_1$-$C_3$)-alkylsulfonyl, ($C_1$-$C_3$)-alkylthio, each substituted by m radicals from the group consisting of fluorine.

Also preferred compounds according to the invention are compounds of formula (I), wherein R$^3$-R$^{13}$ each independently is selected from the group consisting of hydrogen, fluorine, chlorine, bromine, iodine, hydroxyl, cyano, $CO_2R^e$, $CONR^bR^d$, or ($C_1$-$C_6$)-alkyl, ($C_3$-$C_5$)-cycloalkyl, ($C_2$-$C_6$)-alkenyl, each substituted by m radicals from the group consisting of fluorine, or ($C_1$-$C_6$)-alkoxy, ($C_3$-$C_6$)-cycloalkoxy, ($C_3$-$C_6$)-alkenyloxy, ($C_3$-$C_6$)-alkynyloxy, each substituted by m radicals from the group consisting of fluorine.

Also preferred compounds according to the invention are compounds of formula (I), wherein R$^8$-R$^{13}$ each independently is selected from the group consisting of hydrogen, fluorine, chlorine, $CO_2R^e$, $CONR^bR^d$, or ($C_1$-$C_6$)-alkyl, substituted by m radicals from the group consisting of fluorine, or ($C_1$-$C_6$)-alkoxy, substituted by m radicals from the group consisting of fluorine.

In particular, R$^8$-R$^{13}$ each independently is selected from the group consisting of halogen, ($C_1$-$C_6$)-alkyl, ($C_1$-$C_3$)-alkoxy, and $CO_2R^e$.

Further preferred compounds according to the invention are compounds of formula (I), wherein Y is selected from the group consisting of hydrogen, cyano, hydroxyl, Z, or ($C_1$-$C_{12}$)-alkyl, ($C_3$-$C_8$)-cycloalkyl, ($C_2$-$C_{12}$)-alkenyl or ($C_2$-$C_{12}$)-alkynyl, each substituted by m radicals from the group consisting of fluorine, chlorine, bromine, iodine, cyano, hydroxyl, Z, $CO_2R^e$, and $CONR^bR^h$.

Also preferred compounds according to the invention are compounds of formula (I), wherein Y is selected from the group consisting of hydrogen, cyano, hydroxyl, Z, or ($C_1$-$C_{12}$)-alkyl, and ($C_3$-$C_3$)-cycloalkyl, each substituted by m radicals from the group consisting of fluorine, $CO_2R^e$, and $CONR^bR^h$.

Also preferred compounds according to the invention are compounds of formula (I), wherein Y is selected from the group consisting of ($C_1$-$C_{12}$)-alkyl, ($C_3$-$C_8$)-cycloalkyl, ($C_2$-$C_{12}$)-alkenyl or ($C_2$-$C_{12}$)-alkynyl, each substituted by m radicals from the group consisting of fluorine, chlorine, bromine, iodine, cyano, hydroxyl, $OR^d$, Z, OZ, NHZ, $S(O)_nR^a$, $SO_2NR^bR^d$, $SO_2NR^bCOR^e$, $CO_2R^e$, $CONR^bR^h$, $COR^b$, $CONR^eSO_2R^a$, $NR^bR^e$, $NR^bCOR^e$, $NR^bCONR^eR^e$, $NR^bCO_2R^e$, $NR^bSO_2R^e$ $NR^bSO_2NR^bR^e$, $OCONR^bR^e$, $OCSNR^bR^e$, $POR^fR^f$ and $C(R^b){=}NOR^e$.

Also preferred compounds according to the invention are compounds of formula (I), wherein Y is selected from the group consisting of ($C_1$-$C_{12}$)-alkyl, ($C_3$-$C_8$)-cycloalkyl, ($C_2$-$C_{12}$)-alkenyl or ($C_2$-$C_{12}$)-alkynyl, each substituted by m radicals from the group consisting of fluorine and $CO_2R^e$. In particular, Y is selected from the group consisting of Z, or ($C_1$-$C_{12}$)-alkyl, and ($C_3$-$C_8$)-cycloalkyl, each substituted by m radicals from the group consisting of fluorine, $(C_1-C_2)$-alkoxy, $CO_2R^e$, and $CONR^bR^h$.

According to one preferred embodiment, Y is Z.

Preferred compounds according to the invention are compounds of formula (I), wherein Z is selected from the group consisting of four-, five- or six-membered saturated, partly unsaturated, fully unsaturated or aromatic rings, except phenyl, which are formed from r carbon atoms and n oxygen atoms, each substituted by m radicals from the group consisting of $CO_2R^e$, $CONR^bR^h$, $S(O)_nR^a$, $SO_2NR^bR^d$, $SO_2NR^bCOR^e$, $COR^b$, $CONR^eSO_2R^a$, $NR^bR^e$, $NR^bCOR^e$, $NR^bCONR^eR^e$, $NR^bCO_2R^e$, $NR^bSO_2R^e$, $NR^bSO_2NR^bR^e$, $OCONR^bR^e$, $OCSNR^bR^e$, $POR^fR^f$ and $C(R^b){=}NOR^e$, $R^b$, $R^c$, $R^e$ and $R^f$, and where carbon atoms bear n oxo groups.

Also preferred compounds according to the invention are compounds of formula (I), wherein Z is selected from the group consisting of four-, five- or six-membered saturated, partly unsaturated, fully unsaturated or aromatic rings, except phenyl, which are formed from r carbon atoms and n oxygen atoms, each substituted by m radicals from the group consisting of $CO_2R^e$, $CONR^bR^h$, $R^b$, $R^c$, $R^e$ and $R^f$, and where carbon atoms bear n oxo groups.

Further preferred compounds according to the invention are compounds of formula (I), wherein Z is selected from the group consisting of three-, four-, five- or six-membered saturated, partly unsaturated, fully unsaturated or aromatic rings, except phenyl, which are formed from r carbon atoms, n nitrogen atoms, n sulfur atoms and n oxygen atoms, and which are substituted by m radicals from the group consisting of $CO_2R^e$, $CONR^bR^h$, $CONR^eSO_2R^a$, $R^b$, $R^c$, $R^e$ and $R^f$, and where the sulfur atoms and carbon atoms bear n oxo groups.

Representative examples for the three-, four-, five- or six-membered saturated, partly unsaturated, fully unsaturated or aromatic rings mentioned above, are the following structures:

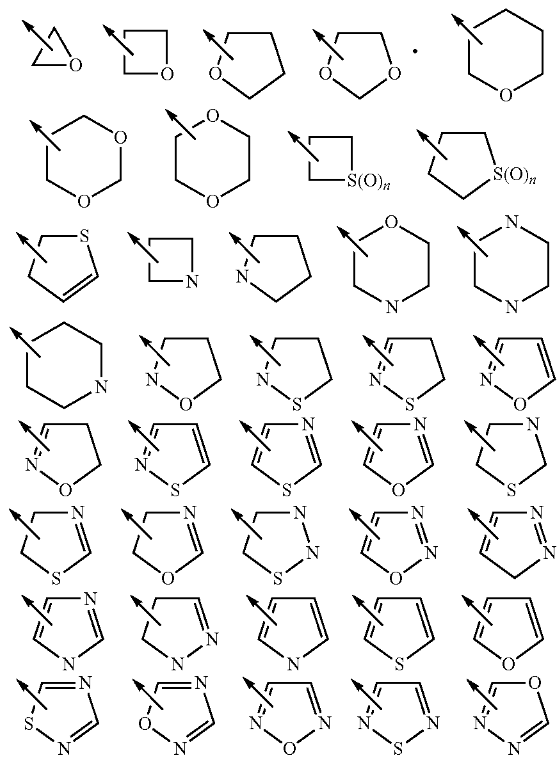

-continued

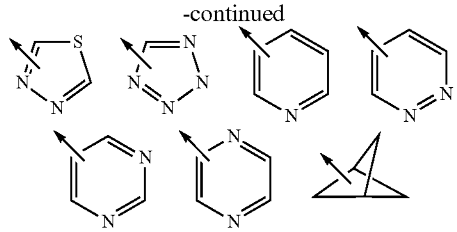

Representative examples for the four-, five- or six-membered saturated, partly unsaturated, fully unsaturated or aromatic rings mentioned above, are the following structures:

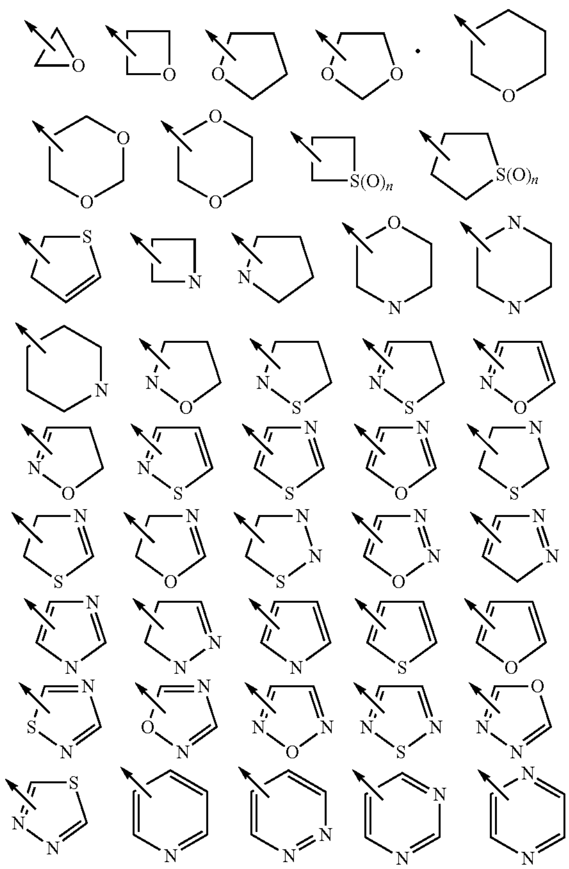

Also preferred compounds according to the invention are compounds of formula (I), wherein Z is selected from the group consisting of four- or five-membered saturated or partly unsaturated rings, which are formed from r carbon atoms and n oxygen atoms, each substituted by m radicals from the group consisting of $CO_2R^e$, $CONR^bR^h$, $CONR^eSO_2R^a$, $R^b$, $R^c$, $R^e$ and $R^f$. Also preferred compounds according to the invention are compounds of formula (I), wherein Z is selected from the group consisting of four- or five-membered saturated or partly unsaturated rings, which are formed from r carbon atoms and n oxygen atoms, each substituted by m radicals from the group consisting of $CO_2R^e$, $CONR^bR^h$, $R^b$, $R^c$, $R^e$ and $R^f$.

Also preferred compounds according to the invention are compounds of formula (I), wherein Z is selected from the group consisting of five-membered saturated or partly unsaturated rings, which are formed from 4 carbon atoms and 1 oxygen atom, each substituted by m radicals from the group consisting of $CO_2R^e$, $CONR^bR^h$, $CONR^eSO_2R^a$, $R^b$, $R^c$, $R^e$ and $R^f$.

Also preferred compounds according to the invention are compounds of formula (I), wherein Z is selected from the group consisting of five-membered saturated or partly unsaturated rings, which are formed from 4 carbon atoms and 1 oxygen atom, each substituted by m radicals from the group consisting of $CO_2R^e$, $CONR^bR^h$, $R^b$, $R^c$, $R^e$ and $R^f$.

Representative examples for the five-membered saturated or partly unsaturated rings, which are formed from 4 carbon atoms and 1 oxygen atom, each substituted by m radicals from the group consisting of $CO_2R^e$, $CONR^bR^h$, $CONR^eSO_2R^a$, $R^b$, $R^c$, $R^e$ and $R^f$ mentioned above, are the following structures, the arrow indicating the bond to any of the mentioned substituents:

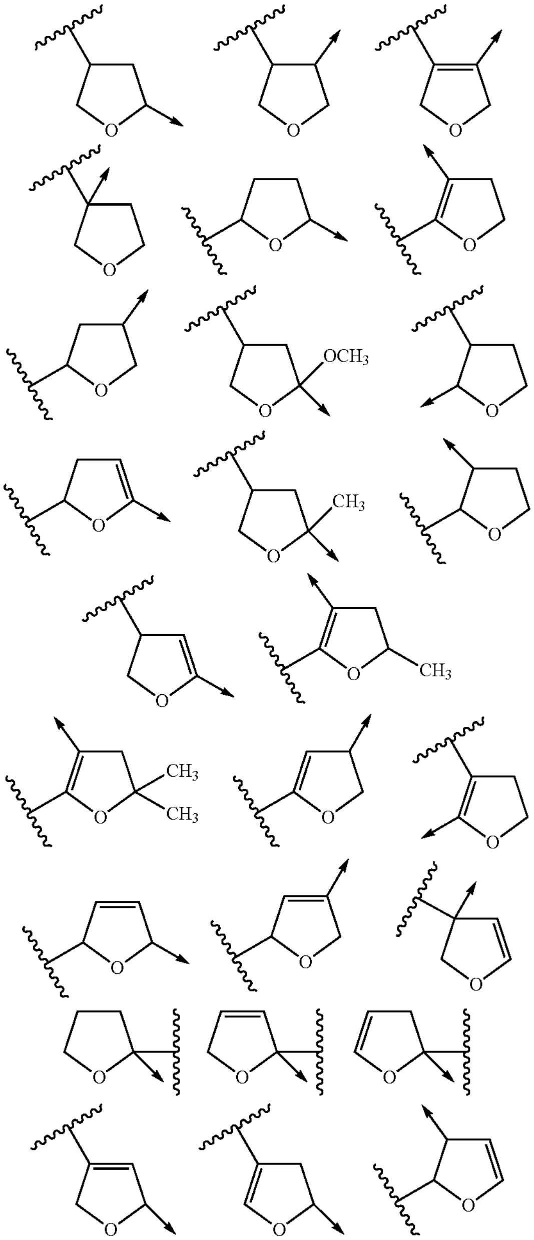

-continued

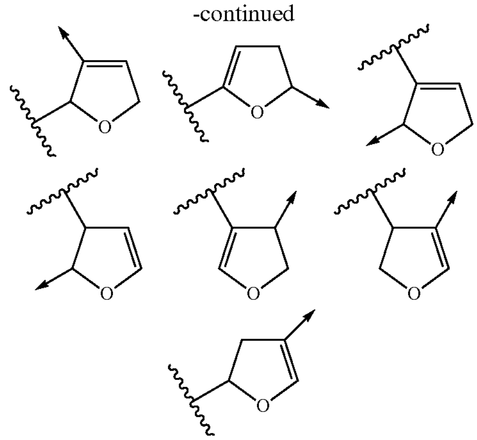

Preferred examples for the five-membered saturated or partly unsaturated rings, which are formed from 4 carbon atoms and 1 oxygen atom, each substituted by m radicals from the group consisting of $CO_2R^e$, $CONR^bR^h$, $CONR^eSO_2R^a$, $R^b$, $R^c$, $R^e$ and $R^f$ mentioned above, are the following structures, the arrow indicating the bond to any of the mentioned substituents, preferably to $CO_2R^e$:

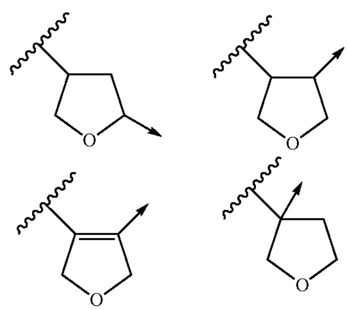

Preferred examples for the five-membered saturated or partly unsaturated rings, which are formed from 4 carbon atoms and 1 oxygen atom, each substituted by m radicals from the group consisting of $CO_2R^e$, $CONR^bR^h$, $R^b$, $R^c$, $R^e$ and $R^f$ mentioned above, are the following structures, the arrow indicating the bond to any of the mentioned substituents, preferably to $CO_2R^e$:

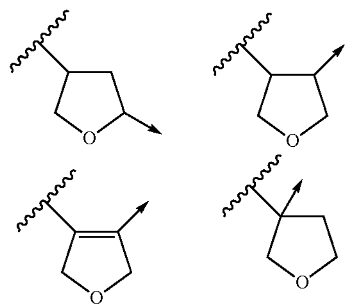

Also preferred compounds according to the invention are compounds of formula (I), wherein Z is selected from the group consisting of five-membered saturated or partly unsaturated rings, which are formed from 5 carbon atoms, each substituted by m radicals from the group consisting of $CO_2R^e$, $CONR^bR^h$, $CONR^eSO_2R^a$, $R^b$, $R^c$, $R^e$ and $R^f$.

Also preferred compounds according to the invention are compounds of formula (I), wherein Z is selected from the group consisting of five-membered saturated or partly unsaturated rings, which are formed from 5 carbon atoms, each substituted by m radicals from the group consisting of $CO_2R^e$, $CONR^bR^h$, $R^b$, $R^c$, $R^e$ and $R^f$.

Representative examples for the five-membered saturated or partly unsaturated rings, which are formed from 5 carbon atoms, each substituted by m radicals from the group consisting of $CO_2R^e$, $CONR^bR^h$, $CONR^eSO_2R^a$, $R^b$, $R^c$, $R^e$ and $R^f$ mentioned above, are the following structures, the arrow indicating the bond to any of the mentioned substituents:

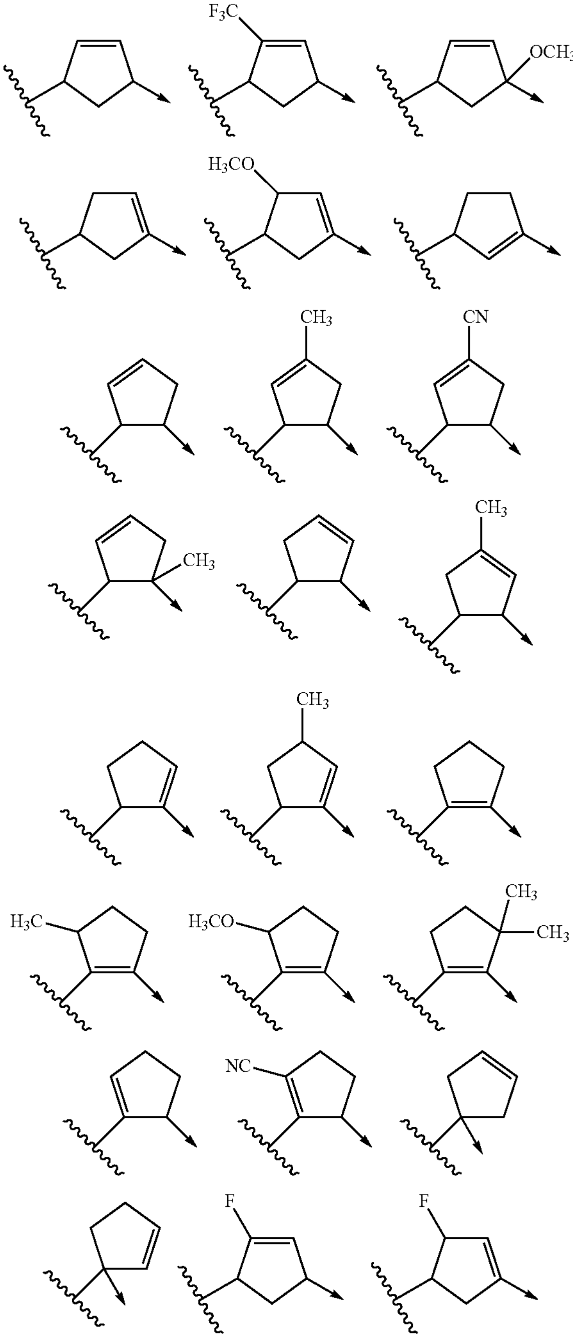

-continued

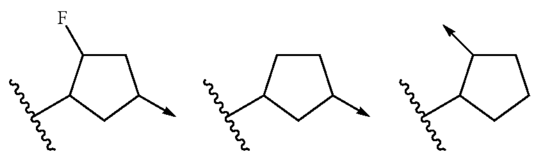

Further representative examples for the five-membered saturated or partly unsaturated rings, which are formed from 5 carbon atoms, each substituted by m radicals from the group consisting of $CO_2R^e$, $CONR^bR^h$, $CONR^eSO_2R^a$, $R^b$, $R^c$, $R^e$ and $R^f$ mentioned above, are the following structures, the arrow indicating the bond to any of the mentioned substituents:

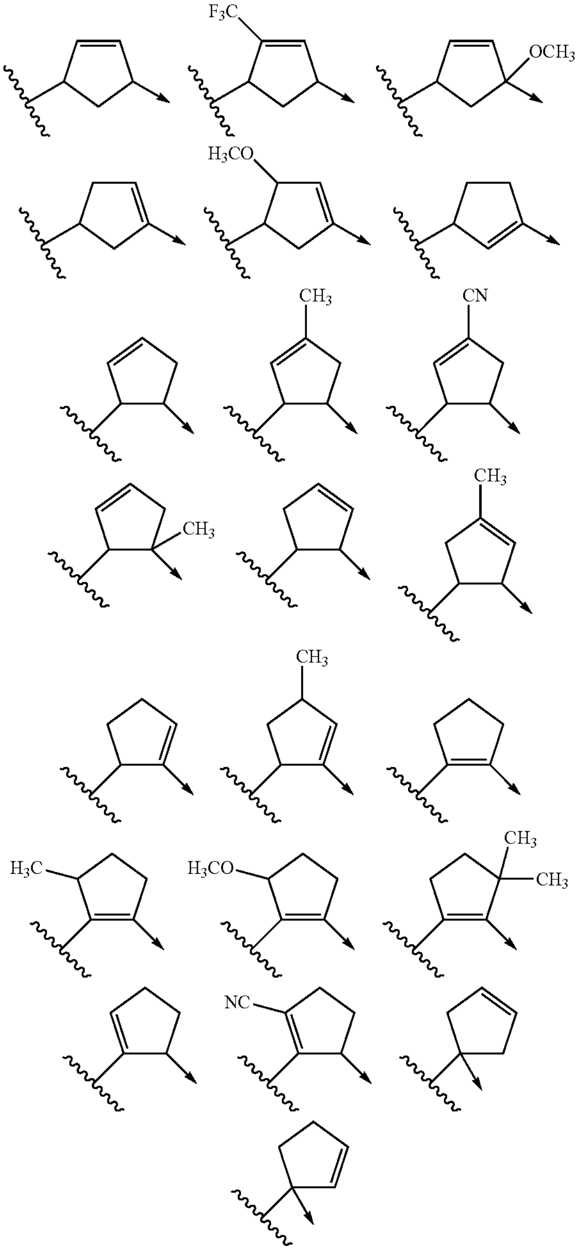

Preferred examples for the five-membered saturated or partly unsaturated rings, which are formed from 5 carbon atoms, each substituted by m radicals from the group consisting of $CO_2R^e$, $CONR^bR^h$, $CONR^eSO_2R^a$, $R^b$, $R^c$, $R^e$ and $R^f$ mentioned above, are the following structures, the arrow indicating the bond to any of the mentioned substituents, preferably to $CO_2R^e$:

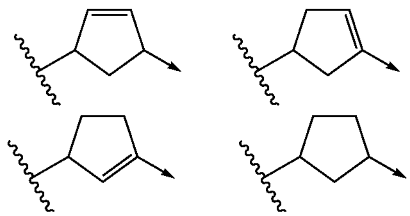

Preferred examples for the five-membered saturated or partly unsaturated rings, which are formed from 5 carbon atoms, each substituted by m radicals from the group consisting of $CO_2R^e$, $CONR^bR^h$, $R^b$, $R^c$, $R^e$ and $R^f$ mentioned above, are the following structures, the arrow indicating the bond to any of the mentioned substituents, preferably to $CO_2R^e$:

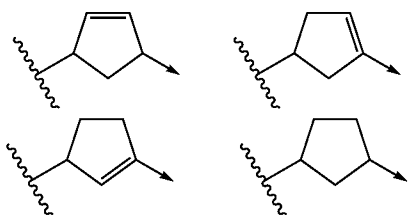

In particular, Z is selected from the group consisting of cyclobutyl, cyclopentyl, cyclopentenyl, and tetrahydrofuranyl, each substituted by m radicals from the group consisting of $CO_2R^e$, $CONR^bR^h$, $CONR^eSO_2R^a$, $R^b$, $R^c$, $R^e$ and $R^f$.

Very particular, Z is selected from the group consisting of cyclobutyl, cyclopentyl, cyclopentenyl, and tetrahydrofuranyl, each substituted by m radicals from the group consisting of $CO_2R^e$, $CONR^bR^h$, $R^b$, $R^c$, $R^e$ and $R^f$.

Preferred examples Z.1 to Z.5, each substituted by m radicals from the group consisting of $CO_2R^e$, $CONR^bR^h$, $CONR^eSO_2R^a$, $R^b$, $R^c$, $R^e$ and $R^f$ mentioned above, are the following structures, arrow (1), representing the binding site to X, arrows (2) and (3) indicating the bond to any of the mentioned substituents, in particular to $CO_2R^e$, $CONR^bR^h$, $R^b$, $R^c$, $R^e$ and $R^f$:

Z.1

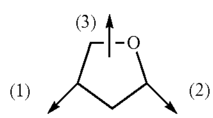

Z.2

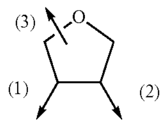

-continued

Z.3

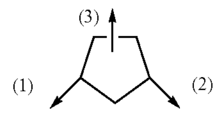

Z.4

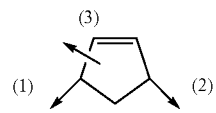

Z.5

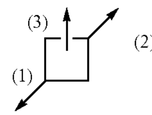

Preferred compounds of the present invention are compounds of formula (I), wherein the substituents have the following meanings:

$R^1$ hydrogen, $(C_1-C_3)$-alkyl, $(C_3-C_4)$-cycloalkyl, $(C_1-C_3)$-haloalkyl, $(C_2-C_3)$-alkenyl, $(C_2-C_3)$-haloalkenyl, $(C_2-C_3)$-alkynyl, $(C_2-C_3)$-haloalkynyl, $(C_1-C_3)$-alkoxy-$(C_1-C_3)$-alkyl, $(C_1-C_3)$-alkoxy, $(C_1-C_3)$-haloalkoxy;

$R^2$ hydrogen, halogen, $(C_1-C_3)$-alkyl, $(C_1-C_3)$-haloalkyl, $(C_1-C_3)$-alkoxy, $(C_1-C_3)$-haloalkoxy;

$R^3$ hydrogen, halogen, nitro, hydroxyl, cyano, $(C_1-C_3)$-alkyl, $(C_1-C_3)$-haloalkyl, hydroxy-$(C_1-C_3)$-alkyl, $(C_3-C_5)$-cycloalkyl, $(C_3-C_5)$-halocycloalkyl, hydroxy-$(C_3-C_5)$-cycloalkyl, $(C_1-C_3)$-alkoxy, $(C_1-C_3)$-haloalkoxy, $(C_1-C_3)$-alkoxycarbonyl, $(C_2-C_3)$-haloalkenyl, $(C_2-C_3)$-haloalkynyl, $(C_1-C_3)$-alkylthio, $(C_1-C_3)$-alkylsulfinyl, $(C_1-C_3)$-alkylsulfonyl;

$R^4$ hydrogen, halogen, hydroxyl, cyano, $(C_1-C_3)$-alkyl, $(C_1-C_3)$-haloalkyl, $(C_3-C_4)$-halocycloalkyl, $(C_1-C_3)$-haloalkoxy, $(C_2-C_3)$-haloalkenyl, $(C_2-C_3)$-haloalkynyl;

$R^5$ hydrogen, halogen, nitro, hydroxyl, cyano, $(C_1-C_3)$-alkyl, $(C_1-C_3)$-haloalkyl, hydroxy-$(C_1-C_3)$-alkyl, $(C_3-C_5)$-cycloalkyl, $(C_3-C_5)$-halocycloalkyl, hydroxy-$(C_3-C_5)$-cycloalkyl, $(C_1-C_3)$-alkoxy, $(C_1-C_3)$-haloalkoxy, $(C_1-C_3)$-alkoxycarbonyl, $(C_2-C_3)$-haloalkenyl, $(C_2-C_3)$-haloalkynyl, $(C_1-C_3)$-alkylthio, $(C_1-C_3)$-alkylsulfinyl, $(C_1-C_3)$-alkylsulfonyl;

$R^6$ hydrogen, halogen, $(C_1-C_3)$-alkyl, $(C_1-C_3)$-haloalkyl, $(C_1-C_3)$-alkoxy, $(C_1-C_3)$-haloalkoxy;

$R^7$ fluorine, cyano, or $(C_1-C_6)$-alkyl, $(C_3-C_6)$-cycloalkyl, $(C_2-C_6)$-alkenyl, $(C_2-C_6)$-alkynyl, $(C_1-C_6)$-alkoxy, each substituted by m radicals from the group consisting of fluorine, chlorine, bromine, iodine, hydroxyl, cyano and $(C_1-C_6)$-alkoxy;

X a bond $(X^0)$ or a divalent unit from the group consisting of $(X^1)$, $(X^2)$, $(X^3)$, $(X^4)$, $(X^5)$, and $(X^6)$:

$(X^1)$

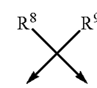

$(X^2)$

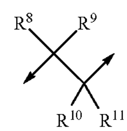

-continued (X³)

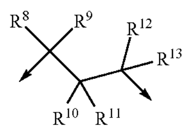

(X⁴)

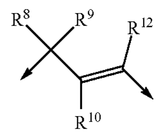

(X⁵)

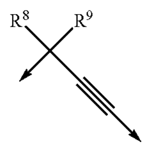

(X⁶)

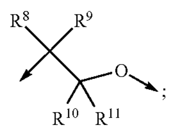

$R^8$-$R^{13}$ each independently hydrogen, fluorine, chlorine, bromine, iodine, hydroxyl, cyano, $CO_2R^e$, $CONR^bR^d$, $R^a$, or $(C_1-C_6)$-alkyl, $(C_3-C_5)$-cycloalkyl, $(C_2-C_6)$-alkenyl, $(C_2-C_6)$-alkynyl, each substituted by m radicals from the group consisting of fluorine, chlorine, bromine, iodine, hydroxyl and cyano, or $(C_1-C_6)$-alkoxy, $(C_3-C_6)$-cycloalkoxy, $(C_3-C_6)$-alkenyloxy or $(C_3-C_6)$-alkynyloxy, each substituted by m radicals from the group consisting of fluorine, chlorine, bromine, iodine, cyano and $(C_1-C_2)$-alkoxy;

Y hydrogen, cyano, hydroxyl, Z, or $(C_1-C_{12})$-alkyl, $(C_3-C_8)$-cycloalkyl, $(C_2-C_{12})$-alkenyl or $(C_2-C_{12})$-alkynyl, each substituted by m radicals from the group consisting of fluorine, chlorine, bromine, iodine, cyano, hydroxyl, $OR^d$, Z, OZ, NHZ, $S(O)_nR^a$, $SO_2NR^bR^d$, $SO_2NR^bCOR^e$, $CO_2R^e$, $CONR^bR^h$, $COR^b$, $CONR^eSO_2R^a$, $NR^bR^e$, $NR^bCOR^e$, $NR^bCONR^eR^e$, $NR^bCO_2R^e$, $NR^bSO_2R^e$, $NR^bSO_2NR^bR^e$, $OCONR^bR^e$, $OCSNR^bR^e$, $POR^fR^f$ and $C(R^b)$=$NOR^e$;

Z a three-, four-, five- or six-membered saturated, partly unsaturated, fully unsaturated or aromatic ring, except phenyl, which is formed from r carbon atoms, n nitrogen atoms, n sulfur atoms and n oxygen atoms, and which is substituted by m radicals from the group consisting of $CO_2R^e$, $CONR^bR^h$, $R^b$, $R^c$, $R^e$ and $R^f$, and where the sulfur atoms and carbon atoms bear n oxo groups;

$R^a$ $(C_1-C_6)$-alkyl or $(C_3-C_6)$-cycloalkyl, each of which is substituted by m radicals selected from the group consisting of fluorine, chlorine, bromine, iodine, cyano and hydroxy;

$R^b$ hydrogen or $R^a$;

$R^c$ fluorine, chlorine, bromine, iodine, cyano, hydroxyl, $S(O)_nR^a$ or $(C_1-C_6)$-alkoxy, $(C_3-C_6)$-alkenyloxy or $(C_3-C_6)$-alkynyloxy, each of which is substituted by m radicals selected from the group consisting of fluorine, chlorine, bromine, cyano and $(C_1-C_2)$-alkoxy;

$R^d$ hydrogen or $(C_1-C_6)$-alkyl, $(C_3-C_6)$-cycloalkyl, $(C_2-C_4)$-alkenyl, phenyl-$(C_1-C_3)$-alkyl or $(C_2-C_4)$-alkynyl, each of which is substituted by m radicals selected from the group consisting of fluorine, chlorine, bromine, cyano and $(C_1-C_2)$-alkoxy;

$R^e$ $R^d$ $R^f$ $(C_1-C_3)$-alkyl or $(C_1-C_3)$-alkoxy;

$R^h$ hydrogen or $(C_1-C_6)$-alkyl, $(C_3-C_6)$-cycloalkyl, $(C_2-C_4)$-alkenyl, $(C_1-C_6)$-alkoxycarbonyl-$(C_1-C_6)$-alkyl, or $(C_2-C_4)$-alkynyl each of which is substituted by m radicals selected from the group consisting of fluorine, chlorine, bromine, cyano and $(C_1-C_2)$-alkoxy;

m 0, 1, 2, 3, 4 or 5;

n 0, 1 or 2;

r 1, 2, 3, 4, 5 or 6;

including their agriculturally acceptable salts, amides, esters or thioesters, provided the compounds of formula (I) have a carboxyl group; with the exception of 5-methyl-3-phenyl-1,4,2-dioxazole-5-carboxamide.

Preferred compounds of the present invention are compounds of formula (I), wherein the substituents have the following meanings:

$R^1$ hydrogen, $(C_1-C_3)$-alkyl, $(C_3-C_4)$-cycloalkyl, $(C_1-C_3)$-haloalkyl, $(C_2-C_3)$-alkenyl, $(C_2-C_3)$-alkynyl, $(C_1-C_3)$-alkoxy-$(C_1-C_3)$-alkyl, $(C_1-C_3)$-alkoxy, preferably hydrogen, $(C_1-C_3)$-alkyl, or $(C_3-C_4)$-cycloalkyl, more preferably hydrogen;

$R^2$ hydrogen;

$R^3$ halogen, cyano, $(C_1-C_3)$-alkyl, preferably fluorine or chlorine;

$R^4$ hydrogen or fluorine, preferably hydrogen;

$R^5$ halogen, cyano, $(C_1-C_3)$-alkyl, preferably fluorine, or chlorine;

$R^6$ hydrogen;

$R^7$ fluorine, cyano, or $(C_1-C_6)$-alkyl, $(C_3-C_6)$-cycloalkyl, $(C_2-C_6)$-alkenyl, $(C_2-C_6)$-alkynyl, $(C_1-C_6)$-alkoxy, each substituted by m radicals from the group consisting of fluorine, chlorine, bromine, iodine, hydroxyl, cyano and $(C_1-C_6)$-alkoxy;

X a bond;

Y Z:

Z a three-, four-, five- or six-membered saturated, partly unsaturated, fully unsaturated or aromatic ring, except phenyl, which is formed from r carbon atoms, n nitrogen atoms, n sulfur atoms and n oxygen atoms, and which is substituted by m radicals from the group consisting of $CO_2R^e$, $CONR^bR^h$, $R^b$, $R^c$, $R^e$ and $R^f$, and where the sulfur atoms and carbon atoms bear n oxo groups;

$R^a$ $(C_1-C_6)$-alkyl or $(C_3-C_6)$-cycloalkyl, each of which is substituted by m radicals selected from the group consisting of fluorine, chlorine, bromine, iodine, cyano and hydroxy;

$R^b$ hydrogen, $(C_1-C_6)$-alkyl or $(C_3-C_6)$-cycloalkyl, each of which is substituted by m radicals selected from the group consisting of fluorine, chlorine, bromine, iodine, cyano and hydroxy;

$R^c$ fluorine, chlorine, bromine, iodine, cyano, hydroxyl, $S(O)_nR^a$ or $(C_1-C_6)$-alkoxy, $(C_3-C_6)$-alkenyloxy or $(C_3-C_6)$-alkynyloxy, each of which is substituted by m radicals selected from the group consisting of fluorine, chlorine, bromine, cyano and $(C_1-C_2)$-alkoxy;

$R^e$ hydrogen or $(C_1-C_6)$-alkyl, $(C_3-C_6)$-cycloalkyl, $(C_2-C_4)$-alkenyl, phenyl-$(C_1-C_3)$-alkyl or $(C_2-C_4)$-alkynyl, each of which is substituted by m radicals selected from the group consisting of fluorine, chlorine, bromine, cyano and $(C_1-C_2)$-alkoxy;

$R^f$ $(C_1-C_3)$-alkyl or $(C_1-C_3)$-alkoxy;

$R^h$ hydrogen or ($C_1$-$C_6$)-alkyl, ($C_3$-$C_6$)-cycloalkyl, ($C_2$-$C_4$)-alkenyl, ($C_1$-$C_6$)-alkoxycarbonyl-($C_1$-$C_6$)-alkyl, or ($C_2$-$C_4$)-alkynyl each of which is substituted by m radicals selected from the group consisting of fluorine, chlorine, bromine, cyano and ($C_1$-$C_2$)-alkoxy;

r 1, 2, 3, 4, 5 or 6;

n 0, 1 or 2;

m 0, 1, 2, 3, 4 or 5.

Further preferred compounds of the present invention are compounds of formula (I), wherein the substituents have the following meanings:

$R^1$ hydrogen, ($C_1$-$C_3$)-alkyl, ($C_3$-$C_4$)-cycloalkyl, ($C_1$-$C_3$)-haloalkyl, ($C_2$-$C_3$)-alkenyl, ($C_2$-$C_3$)-alkynyl, ($C_1$-$C_3$)-alkoxy-($C_1$-$C_3$)-alkyl, ($C_1$-$C_3$)-alkoxy, preferably hydrogen, ($C_1$-$C_3$)-alkyl, or ($C_3$-$C_4$)-cycloalkyl, more preferably hydrogen;

$R^2$ hydrogen;

$R^3$ halogen, cyano, ($C_1$-$C_3$)-alkyl, preferably fluorine or chlorine;

$R^4$ hydrogen or fluorine, preferably hydrogen;

$R^5$ halogen, cyano, ($C_1$-$C_3$)-alkyl, preferably fluorine, or chlorine;

$R^6$ hydrogen;

$R^7$ fluorine, cyano, or ($C_1$-$C_6$)-alkyl, ($C_3$-$C_6$)-cycloalkyl, ($C_2$-$C_6$)-alkenyl, ($C_2$-$C_6$)-alkynyl, ($C_1$-$C_6$)-alkoxy, each substituted by m radicals from the group consisting of fluorine, chlorine, bromine, iodine, hydroxyl, cyano and ($C_1$-$C_6$)-alkoxy;

X a bond;

Y Z;

Z a three-, four-, five- or six-membered saturated, partly unsaturated, fully unsaturated or aromatic ring, except phenyl, which is formed from r carbon atoms, n nitrogen atoms, n sulfur atoms and n oxygen atoms, and which is substituted by m radicals from the group consisting of $CO_2R^e$, and where the sulfur atoms and carbon atoms bear n oxo groups;

$R^e$ hydrogen or ($C_1$-$C_6$)-alkyl, ($C_3$-$C_6$)-cycloalkyl, ($C_3$-$C_4$)-alkenyl, phenyl-($C_1$-$C_3$)-alkyl or ($C_3$-$C_4$)-alkynyl, each of which is substituted by m radicals selected from the group consisting of fluorine, chlorine, bromine, cyano and ($C_1$-$C_2$)-alkoxy;

r 1, 2, 3, 4, 5 or 6;

n 0, 1 or 2;

m 0, 1, 2, 3, 4 or 5.

Further preferred compounds of the present invention are compounds of formula (I), wherein the substituents have the following meanings:

$R^1$ hydrogen, ($C_1$-$C_3$)-alkyl, ($C_3$-$C_4$)-cycloalkyl, ($C_1$-$C_3$)-haloalkyl, ($C_2$-$C_3$)-alkenyl, ($C_2$-$C_3$)-alkynyl, ($C_1$-$C_3$)-alkoxy-($C_1$-$C_3$)-alkyl, ($C_1$-$C_3$)-alkoxy, preferably hydrogen, ($C_1$-$C_3$)-alkyl, or ($C_3$-$C_4$)-cycloalkyl, more preferably hydrogen;

$R^2$ hydrogen;

$R^3$ halogen, cyano, ($C_1$-$C_3$)-alkyl, preferably fluorine or chlorine;

$R^4$ hydrogen or fluorine, preferably hydrogen;

$R^5$ halogen, cyano, ($C_1$-$C_3$)-alkyl, preferably fluorine, or chlorine;

$R^6$ hydrogen;

$R^7$ fluorine, cyano, or ($C_1$-$C_6$)-alkyl, ($C_3$-$C_6$)-cycloalkyl, ($C_2$-$C_6$)-alkenyl, ($C_2$-$C_6$)-alkynyl, ($C_1$-$C_6$)-alkoxy, each substituted by m radicals from the group consisting of fluorine, chlorine, bromine, iodine, hydroxyl, cyano and ($C_1$-$C_6$)-alkoxy;

X a bond;

Y Z;

Z five-membered saturated, partly unsaturated, or fully unsaturated carbocycle, which is substituted by m radicals from the group consisting of $CO_2R^e$, $CONR^bR^h$, $R^b$, $R^c$, $R^e$ and $R^f$;

$R^a$ ($C_1$-$C_6$)-alkyl or ($C_3$-$C_6$)-cycloalkyl, each of which is substituted by m radicals selected from the group consisting of fluorine, chlorine, bromine, iodine, cyano and hydroxy;

$R^b$ hydrogen, ($C_1$-$C_6$)-alkyl or ($C_3$-$C_6$)-cycloalkyl, each of which is substituted by m radicals selected from the group consisting of fluorine, chlorine, bromine, iodine, cyano and hydroxy;

$R^c$ fluorine, chlorine, bromine, iodine, cyano, hydroxyl, $S(O)_nR^a$ or ($C_1$-$C_6$)-alkoxy, ($C_3$-$C_6$)-alkenyloxy or ($C_3$-$C_6$)-alkynyloxy, each of which is substituted by m radicals selected from the group consisting of fluorine, chlorine, bromine, cyano and ($C_1$-$C_2$)-alkoxy;

$R^e$ hydrogen or ($C_1$-$C_6$)-alkyl, ($C_3$-$C_6$)-cycloalkyl, ($C_2$-$C_4$)-alkenyl, phenyl-($C_1$-$C_3$)-alkyl or ($C_2$-$C_4$)-alkynyl, each of which is substituted by m radicals selected from the group consisting of fluorine, chlorine, bromine, cyano and ($C_1$-$C_2$)-alkoxy;

$R^f$ ($C_1$-$C_3$)-alkyl or ($C_1$-$C_3$)-alkoxy;

$R^h$ hydrogen or ($C_1$-$C_6$)-alkyl, ($C_3$-$C_6$)-cycloalkyl, ($C_2$-$C_4$)-alkenyl, ($C_1$-$C_6$)-alkoxycarbonyl-($C_1$-$C_6$)-alkyl, or ($C_2$-$C_4$)-alkynyl each of which is substituted by m radicals selected from the group consisting of fluorine, chlorine, bromine, cyano and ($C_1$-$C_2$)-alkoxy;

m 0, 1, 2 or 3.

Further preferred compounds of the present invention are compounds of formula (I), wherein the substituents have the following meanings:

$R^1$ hydrogen, ($C_1$-$C_3$)-alkyl, ($C_3$-$C_4$)-cycloalkyl, ($C_1$-$C_3$)-haloalkyl, ($C_2$-$C_3$)-alkenyl, ($C_2$-$C_3$)-alkynyl, ($C_1$-$C_3$)-alkoxy-($C_1$-$C_3$)-alkyl, ($C_1$-$C_3$)-alkoxy, preferably hydrogen, ($C_1$-$C_3$)-alkyl, or ($C_3$-$C_4$)-cycloalkyl, more preferably hydrogen;

$R^2$ hydrogen;

$R^3$ halogen, cyano, ($C_1$-$C_3$)-alkyl, preferably fluorine or chlorine;

$R^4$ hydrogen or fluorine, preferably hydrogen;

$R^5$ halogen, cyano, ($C_1$-$C_3$)-alkyl, preferably fluorine, or chlorine;

$R^6$ hydrogen;

$R^7$ fluorine, cyano, or ($C_1$-$C_6$)-alkyl, ($C_3$-$C_6$)-cycloalkyl, ($C_2$-$C_6$)-alkenyl, ($C_2$-$C_6$)-alkynyl, ($C_1$-$C_6$)-alkoxy, each substituted by m radicals from the group consisting of fluorine, chlorine, bromine, iodine, hydroxyl, cyano and ($C_1$-$C_6$)-alkoxy;

X a bond;

Y Z;

Z five-membered saturated, partly unsaturated, or fully unsaturated carbocycle, which is substituted by m radicals from the group consisting of $CO_2R^e$ and $R^b$;

$R^b$ hydrogen or ($C_1$-$C_6$)-alkyl or ($C_3$-$C_6$)-cycloalkyl, each of which is substituted by m radicals selected from the group consisting of fluorine, chlorine, bromine, iodine, cyano and hydroxy;

$R^e$ hydrogen or ($C_1$-$C_6$)-alkyl, ($C_3$-$C_6$)-cycloalkyl, ($C_3$-$C_4$)-alkenyl, phenyl-($C_1$-$C_3$)-alkyl or ($C_3$-$C_4$)-alkynyl, each of which is substituted by m radicals selected from the group consisting of fluorine, chlorine, bromine, cyano and ($C_1$-$C_2$)-alkoxy;

m 0, 1, 2 or 3.

Further preferred compounds of the present invention are compounds of formula (I), wherein the substituents have the following meanings:

$R^1$ hydrogen, $(C_1-C_3)$-alkyl, $(C_3-C_4)$-cycloalkyl, $(C_1-C_3)$-haloalkyl, $(C_2-C_3)$-alkenyl, $(C_2-C_3)$-alkynyl, $(C_1-C_3)$-alkoxy-$(C_1-C_3)$-alkyl, $(C_1-C_3)$-alkoxy, preferably hydrogen, $(C_1-C_3)$-alkyl, or $(C_3-C_4)$-cycloalkyl, more preferably hydrogen;

$R^2$ hydrogen;

$R^3$ halogen, cyano, $(C_1-C_3)$-alkyl, preferably fluorine or chlorine;

$R^4$ hydrogen or fluorine, preferably hydrogen;

$R^5$ halogen, cyano, $(C_1-C_3)$-alkyl, preferably fluorine, or chlorine;

$R^6$ hydrogen;

$R^7$ fluorine, cyano, or $(C_1-C_6)$-alkyl, $(C_3-C_6)$-cycloalkyl, $(C_2-C_6)$-alkenyl, $(C_2-C_6)$-alkynyl, $(C_1-C_6)$-alkoxy, each substituted by m radicals from the group consisting of fluorine, chlorine, bromine, iodine, hydroxyl, cyano and $(C_1-C_6)$-alkoxy;

X a bond;

Y $(C_1-C_3)$-alkyl, $(C_3-C_8)$-cycloalkyl, $(C_2-C_8)$-alkenyl or $(C_2-C_8)$-alkynyl, each substituted by m radicals from the group consisting of fluorine and $CO_2R^e$;

$R^e$ hydrogen or $(C_1-C_6)$-alkyl, $(C_3-C_6)$-cycloalkyl, $(C_2-C_4)$-alkenyl, phenyl-$(C_1-C_3)$-alkyl or $(C_2-C_4)$-alkynyl, each of which is substituted by m radicals selected from the group consisting of fluorine, chlorine, bromine, cyano and $(C_1-C_2)$-alkoxy;

m 0, 1, 2, or 3.

Further preferred compounds of the present invention are compounds of formula (I), wherein the substituents have the following meanings:

$R^1$ hydrogen, $(C_1-C_3)$-alkyl, $(C_3-C_4)$-cycloalkyl, $(C_1-C_3)$-haloalkyl, $(C_2-C_3)$-alkenyl, $(C_2-C_3)$-alkynyl, $(C_1-C_3)$-alkoxy-$(C_1-C_3)$-alkyl, $(C_1-C_3)$-alkoxy, preferably hydrogen, $(C_1-C_3)$-alkyl, or $(C_3-C_4)$-cycloalkyl, more preferably hydrogen;

$R^2$ hydrogen;

$R^3$ halogen, cyano, $(C_1-C_3)$-alkyl, preferably fluorine or chlorine;

$R^4$ hydrogen or fluorine, preferably hydrogen;

$R^5$ halogen, cyano, $(C_1-C_3)$-alkyl, preferably fluorine, or chlorine;

$R^6$ hydrogen;

$R^7$ fluorine, cyano, or $(C_1-C_6)$-alkyl, $(C_3-C_6)$-cycloalkyl, $(C_2-C_6)$-alkenyl, $(C_2-C_6)$-alkynyl, $(C_1-C_6)$-alkoxy, each substituted by m radicals from the group consisting of fluorine, chlorine, bromine, iodine, hydroxyl, cyano and $(C_1-C_6)$-alkoxy;

X a bond;

Y $(C_1-C_3)$-alkyl, $(C_3-C_8)$-cycloalkyl, $(C_2-C_8)$-alkenyl or $(C_2-C_8)$-alkynyl, each substituted by m radicals from the group consisting of fluorine, chlorine, bromine, iodine, cyano, hydroxyl, $OR^d$, Z, OZ, NHZ, $S(O)_nR^a$, $SO_2NR^bR^d$, $SO_2NR^bCOR^e$, $CO_2R^e$, $CONR^bR^h$, $COR^b$, CON—$R^eSO_2R^a$, $NR^bR^e$, $NR^bCOR^e$, $NR^bCONR^eR^e$, $NR^bCO_2R^e$, $NR^bSO_2R^e$ $NR^bSO_2NR^bR^e$, $OCONR^bR^e$, $OCSNR^bR^e$, $POR^fR^f$ and $C(R^b)$═$NOR^e$;

Z a three-, four-, five- or six-membered saturated, partly unsaturated, fully unsaturated or aromatic ring, except phenyl, which is formed from r carbon atoms, n nitrogen atoms, n sulfur atoms and n oxygen atoms, and which is substituted by m radicals from the group consisting of $CO_2R^e$, $CONR^bR^h$, $R^b$, $R^c$, $R^e$ and $R^f$, and where the sulfur atoms and carbon atoms bear n oxo groups;

$R^a$ $(C_1-C_6)$-alkyl or $(C_3-C_6)$-cycloalkyl, each of which is substituted by m radicals selected from the group consisting of fluorine, chlorine, bromine, iodine, cyano and hydroxy;

$R^b$ hydrogen, $(C_1-C_6)$-alkyl or $(C_3-C_6)$-cycloalkyl, each of which is substituted by m radicals selected from the group consisting of fluorine, chlorine, bromine, iodine, cyano and hydroxy;

$R^c$ fluorine, chlorine, bromine, iodine, cyano, hydroxyl, $S(O)_nR^a$ or $(C_1-C_6)$-alkoxy, $(C_3-C_6)$-alkenyloxy or $(C_3-C_6)$-alkynyloxy, each of which is substituted by m radicals selected from the group consisting of fluorine, chlorine, bromine, cyano and $(C_1-C_2)$-alkoxy;

$R^d$ hydrogen or $(C_1-C_6)$-alkyl, $(C_3-C_6)$-cycloalkyl, $(C_2-C_4)$-alkenyl, phenyl-$(C_1-C_3)$-alkyl or $(C_2-C_4)$-alkynyl, each of which is substituted by m radicals selected from the group consisting of fluorine, chlorine, bromine, cyano and $(C_1-C_2)$-alkoxy;

$R^e$ hydrogen or $(C_1-C_6)$-alkyl, $(C_3-C_6)$-cycloalkyl, $(C_2-C_4)$-alkenyl, phenyl-$(C_1-C_3)$-alkyl or $(C_2-C_4)$-alkynyl, each of which is substituted by m radicals selected from the group consisting of fluorine, chlorine, bromine, cyano and $(C_1-C_2)$-alkoxy;

$R^f$ $(C_1-C_3)$-alkyl or $(C_1-C_3)$-alkoxy;

$R^h$ hydrogen or $(C_1-C_6)$-alkyl, $(C_3-C_6)$-cycloalkyl, $(C_2-C_4)$-alkenyl, $(C_1-C_6)$-alkoxycarbonyl-$(C_1-C_6)$-alkyl, or $(C_2-C_4)$-alkynyl each of which is substituted by m radicals selected from the group consisting of fluorine, chlorine, bromine, cyano and $(C_1-C_2)$-alkoxy;

r 1, 2, 3, 4, 5 or 6;

m 0, 1, 2 or 3;

n 0, 1 or 2.

Further preferred compounds of the present invention are compounds of formula (I), wherein the substituents have the following meanings:

$R^1$ hydrogen, $(C_1-C_3)$-alkyl, $(C_3-C_4)$-cycloalkyl, $(C_1-C_3)$-haloalkyl, $(C_2-C_3)$-alkenyl, $(C_2-C_3)$-haloalkenyl, $(C_2-C_3)$-alkynyl, $(C_2-C_3)$-haloalkynyl, $(C_1-C_3)$-alkoxy-$(C_1-C_3)$-alkyl, $(C_1-C_3)$-alkoxy, $(C_1-C_3)$-haloalkoxy;

$R^2$ hydrogen, halogen, $(C_1-C_3)$-alkyl, $(C_1-C_3)$-haloalkyl, $(C_1-C_3)$-alkoxy, $(C_1-C_3)$-haloalkoxy;

$R^3$ hydrogen, halogen, hydroxyl, cyano, $(C_1-C_3)$-alkyl, $(C_1-C_3)$-haloalkyl, $(C_3-C_5)$-halocycloalkyl, $(C_1-C_3)$-haloalkoxy, $(C_2-C_3)$-haloalkenyl, $(C_2-C_3)$-haloalkynyl;

$R^4$ hydrogen, halogen, hydroxyl, cyano, $(C_1-C_3)$-alkyl, $(C_1-C_3)$-haloalkyl, $(C_3-C_4)$-halocycloalkyl, $(C_1-C_3)$-haloalkoxy, $(C_2-C_3)$-haloalkenyl, $(C_2-C_3)$-haloalkynyl;

$R^5$ hydrogen, halogen, hydroxyl, cyano, $(C_1-C_3)$-alkyl, $(C_1-C_3)$-haloalkyl, $(C_3-C_5)$-halocycloalkyl, $(C_1-C_3)$-haloalkoxy, $(C_2-C_3)$-haloalkenyl, $(C_2-C_3)$-haloalkynyl;

$R^6$ hydrogen, halogen, $(C_1-C_3)$-alkyl, $(C_1-C_3)$-haloalkyl, $(C_1-C_3)$-alkoxy, $(C_1-C_3)$-haloalkoxy;

$R^7$ $(C_1-C_2)$-alkyl, cyclopropyl, $(C_1-C_2)$-haloalkyl, $(C_2-C_3)$-alkenyl, $(C_1-C_2)$-alkoxy;

X a bond ($X^0$) or a divalent unit from the group consisting of ($X^1$), ($X^2$), ($X^3$), ($X^4$), ($X^5$), and ($X^6$):

($X^1$)

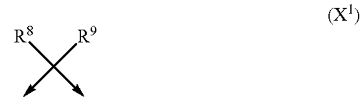

($X^2$)

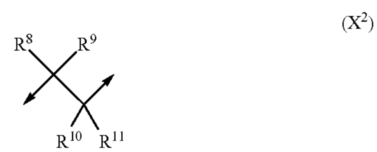

-continued (X³)

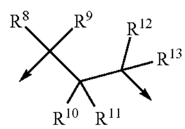

(X⁴)

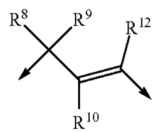

(X⁵)

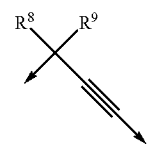

(X⁶)

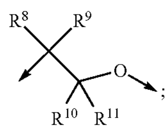

;

$R^8$-$R^{13}$ each independently hydrogen, fluorine, chlorine, bromine, iodine, hydroxyl, cyano, $CO_2R^e$, $CONR^bR^d$, $R^a$, or ($C_1$-$C_6$)-alkyl, ($C_3$-$C_5$)-cycloalkyl, ($C_2$-$C_6$)-alkenyl, ($C_2$-$C_6$)-alkynyl each substituted by m radicals from the group consisting of fluorine, chlorine, bromine, iodine, hydroxyl and cyano, or ($C_1$-$C_6$)-alkoxy, ($C_3$-$C_6$)-cycloalkoxy, ($C_3$-$C_6$)-alkenyloxy or ($C_3$-$C_6$)-alkynyloxy each substituted by m radicals from the group consisting of fluorine, chlorine, bromine, iodine, cyano and ($C_1$-$C_2$)-alkoxy;

Y cyano, hydroxyl, Z, or ($C_1$-$C_{12}$)-alkyl, ($C_3$-$C_8$)-cycloalkyl, ($C_2$-$C_{12}$)-alkenyl or ($C_2$-$C_{12}$)-alkynyl each substituted by m radicals from the group consisting of fluorine, chlorine, bromine, iodine, cyano, hydroxyl, $OR^d$, Z, OZ, NHZ, $S(O)_nR^a$, $SO_2NR^bR^d$, $SO_2NR^bCOR^e$, $CO_2R^e$, $CONR^bR^h$, $COR^b$, $CONR^eSO_2R^a$, $NR^bR^e$, $NR^b$-$COR^e$, $NR^bCONR^eR^e$, $NR^bCO_2R^e$, $NR^bSO_2R^e$ $NR^bSO_2NR^bR^e$, $OCONR^bR^e$, $OCSNR^bR^e$, $POR^fR^f$ and $C(R^b)$═$NOR^e$;

Z a three-, four-, five- or six-membered saturated, partly unsaturated, fully unsaturated or aromatic ring, except phenyl, which is formed from r carbon atoms, n nitrogen atoms, n sulfur atoms and n oxygen atoms, and which is substituted by m radicals from the group consisting of $CO_2R^e$, $CONR^bR^h$, $R^b$, $R^c$, $R^e$ and $R^f$, and where the sulfur atoms and carbon atoms bear n oxo groups;

$R^a$ ($C_1$-$C_6$)-alkyl or ($C_3$-$C_6$)-cycloalkyl, each of which is substituted by m radicals selected from the group consisting of fluorine, chlorine, bromine, iodine, cyano and hydroxy;

$R^b$ hydrogen or $R^a$;

$R^c$ fluorine, chlorine, bromine, iodine, cyano, hydroxyl, $S(O)_nR^a$ or ($C_1$-$C_6$)-alkoxy, ($C_3$-$C_6$)-alkenyloxy or ($C_3$-$C_6$)-alkynyloxy, each of which is substituted by m radicals selected from the group consisting of fluorine, chlorine, bromine, cyano and ($C_1$-$C_2$)-alkoxy;

$R^d$ hydrogen or ($C_1$-$C_6$)-alkyl, ($C_3$-$C_6$)-cycloalkyl, ($C_2$-$C_4$)-alkenyl, phenyl-($C_1$-$C_3$)-alkyl or ($C_2$-$C_4$)-alkynyl, each of which is substituted by m radicals selected from the group consisting of fluorine, chlorine, bromine, cyano and ($C_1$-$C_2$)-alkoxy;

$R^e$ $R^d$;

$R^f$ ($C_1$-$C_3$)-alkyl or ($C_1$-$C_3$)-alkoxy;

$R^h$ hydrogen or ($C_1$-$C_6$)-alkyl, ($C_3$-$C_6$)-cycloalkyl, ($C_2$-$C_4$)-alkenyl, ($C_1$-$C_6$)-alkoxycarbonyl-($C_1$-$C_6$)-alkyl, or ($C_2$-$C_4$)-alkynyl each of which is substituted by m radicals selected from the group consisting of fluorine, chlorine, bromine, cyano and ($C_1$-$C_2$)-alkoxy;

m 0, 1, 2, 3, 4 or 5;

n 0, 1 or 2;

r 1, 2, 3, 4, 5 or 6;

Further preferred compounds of the present invention are compounds of formula (I), wherein the substituents have the following meanings:

$R^1$ hydrogen, ($C_1$-$C_3$)-alkyl, ($C_3$-$C_4$)-cycloalkyl, ($C_1$-$C_3$)-haloalkyl, ($C_2$-$C_3$)-alkenyl, ($C_2$-$C_3$)-haloalkenyl, ($C_2$-$C_3$)-alkynyl, ($C_2$-$C_3$)-haloalkynyl, ($C_1$-$C_3$)-alkoxy-($C_1$-$C_3$)-alkyl, ($C_1$-$C_3$)-alkoxy, ($C_1$-$C_3$)-haloalkoxy;

$R^2$ hydrogen, halogen, ($C_1$-$C_3$)-alkyl, ($C_1$-$C_3$)-haloalkyl, ($C_1$-$C_3$)-alkoxy, ($C_1$-$C_3$)-haloalkoxy;

$R^3$ hydrogen, halogen, hydroxyl, cyano, ($C_1$-$C_3$)-alkyl, ($C_1$-$C_3$)-haloalkyl, ($C_3$-$C_5$)-halocycloalkyl, ($C_1$-$C_3$)-haloalkoxy, ($C_2$-$C_3$)-haloalkenyl, ($C_2$-$C_3$)-haloalkynyl;

$R^4$ hydrogen, halogen, hydroxyl, cyano, ($C_1$-$C_3$)-alkyl, ($C_1$-$C_3$)-haloalkyl, ($C_3$-$C_4$)-halocycloalkyl, ($C_1$-$C_3$)-haloalkoxy, ($C_2$-$C_3$)-haloalkenyl, ($C_2$-$C_3$)-haloalkynyl;

$R^5$ hydrogen, halogen, hydroxyl, cyano, ($C_1$-$C_3$)-alkyl, ($C_1$-$C_3$)-haloalkyl, ($C_3$-$C_5$)-halocycloalkyl, ($C_1$-$C_3$)-haloalkoxy, ($C_2$-$C_3$)-haloalkenyl, ($C_2$-$C_3$)-haloalkynyl;

$R^6$ hydrogen, halogen, ($C_1$-$C_3$)-alkyl, ($C_1$-$C_3$)-haloalkyl, ($C_1$-$C_3$)-alkoxy, ($C_1$-$C_3$)-haloalkoxy;

$R^7$ ($C_1$-$C_2$)-alkyl, cyclopropyl, ($C_1$-$C_2$)-haloalkyl, ($C_2$-$C_3$)-alkenyl, ($C_1$-$C_2$)-alkoxy;

X a bond;

Y Z, or ($C_1$-$C_3$)-alkyl, ($C_3$-$C_8$)-cycloalkyl, ($C_2$-$C_8$)-alkenyl or ($C_2$-$C_8$)-alkynyl, each substituted by m radicals from the group consisting of fluorine, $CO_2R^e$ and $CONR^eSO_2R^a$;

Z four to five-membered saturated or partly unsaturated ring which is formed from r carbon atoms, n oxygen atoms, and which is substituted by m radicals from the group consisting of $CO_2R^e$, $CONR^bR^h$, $CONR^eSO_2R^a$, $R^b$, $R^c$, $R^e$ and $R^f$;

$R^a$ ($C_1$-$C_6$)-alkyl or ($C_3$-$C_6$)-cycloalkyl, each of which is substituted by m radicals selected from the group consisting of fluorine, chlorine, bromine, iodine, cyano and hydroxy;

$R^b$ hydrogen, or ($C_1$-$C_6$)-alkyl or ($C_3$-$C_6$)-cycloalkyl, each of which is substituted by m radicals selected from the group consisting of fluorine, chlorine, bromine, iodine, cyano and hydroxy;

$R^c$ fluorine, chlorine, bromine, iodine, cyano, hydroxyl, $S(O)_nR^a$ or ($C_1$-$C_6$)-alkoxy, ($C_3$-$C_6$)-alkenyloxy or ($C_3$-$C_6$)-alkynyloxy, each of which is substituted by m radicals selected from the group consisting of fluorine, chlorine, bromine, cyano and ($C_1$-$C_2$)-alkoxy;

$R^e$ hydrogen or ($C_1$-$C_6$)-alkyl, ($C_3$-$C_6$)-cycloalkyl, ($C_2$-$C_4$)-alkenyl, phenyl-($C_1$-$C_3$)-alkyl or ($C_2$-$C_4$)-alkynyl, each of which is substituted by m radicals selected from the group consisting of fluorine, chlorine, bromine, cyano and ($C_1$-$C_2$)-alkoxy;

$R^f$ ($C_1$-$C_3$)-alkyl or ($C_1$-$C_3$)-alkoxy;

$R^h$ hydrogen or ($C_1$-$C_6$)-alkyl, ($C_3$-$C_6$)-cycloalkyl, ($C_2$-$C_4$)-alkenyl, ($C_1$-$C_6$)-alkoxycarbonyl-($C_1$-$C_6$)-alkyl, or ($C_2$-$C_4$)-alkynyl each of which is substituted by m radicals selected from the group consisting of fluorine, chlorine, bromine, cyano and $(C_1-C_2)$-alkoxy;

m 0, 1, 2, 3, 4 or 5;

n 0, 1 or 2;

r 1, 2, 3, 4, or 5.

Further preferred compounds of the present invention are compounds of formula (I), wherein the substituents have the following meanings:

$R^1$ hydrogen, $(C_1-C_3)$-alkyl, $(C_3-C_4)$-cycloalkyl, $(C_1-C_3)$-haloalkyl, $(C_2-C_3)$-alkenyl, $(C_2-C_3)$-haloalkenyl, $(C_2-C_3)$-alkynyl, $(C_2-C_3)$-haloalkynyl, $(C_1-C_3)$-alkoxy-$(C_1-C_3)$-alkyl, $(C_1-C_3)$-alkoxy, $(C_1-C_3)$-haloalkoxy;

$R^2$ hydrogen, halogen, $(C_1-C_3)$-alkyl, $(C_1-C_3)$-haloalkyl, $(C_1-C_3)$-alkoxy, $(C_1-C_3)$-haloalkoxy;

$R^3$ hydrogen, halogen, hydroxyl, cyano, $(C_1-C_3)$-alkyl, $(C_1-C_3)$-haloalkyl, $(C_3-C_5)$-halocycloalkyl, $(C_1-C_3)$-haloalkoxy, $(C_2-C_3)$-haloalkenyl, $(C_2-C_3)$-haloalkynyl;

$R^4$ hydrogen, halogen, hydroxyl, cyano, $(C_1-C_3)$-alkyl, $(C_1-C_3)$-haloalkyl, $(C_3-C_4)$-halocycloalkyl, $(C_1-C_3)$-haloalkoxy, $(C_2-C_3)$-haloalkenyl, $(C_2-C_3)$-haloalkynyl;

$R^5$ hydrogen, halogen, hydroxyl, cyano, $(C_1-C_3)$-alkyl, $(C_1-C_3)$-haloalkyl, $(C_3-C_5)$-halocycloalkyl, $(C_1-C_3)$-haloalkoxy, $(C_2-C_3)$-haloalkenyl, $(C_2-C_3)$-haloalkynyl;

$R^6$ hydrogen, halogen, $(C_1-C_3)$-alkyl, $(C_1-C_3)$-haloalkyl, $(C_1-C_3)$-alkoxy, $(C_1-C_3)$-haloalkoxy;

$R^7$ $(C_1-C_2)$-alkyl, cyclopropyl, $(C_1-C_2)$-haloalkyl, $(C_2-C_3)$-alkenyl, $(C_1-C_2)$-alkoxy;

X a bond;

Y Z, or $(C_1-C_3)$-alkyl, $(C_3-C_8)$-cycloalkyl, $(C_2-C_8)$-alkenyl or $(C_2-C_8)$-alkynyl, each substituted by m radicals from the group consisting of fluorine and $CO_2R^e$;

Z four to five-membered saturated or partly unsaturated ring which is formed from r carbon atoms, n oxygen atoms, and which is substituted by m radicals from the group consisting of $CO_2R^e$, $CONR^bR^h$, $R^b$, $R^c$, $R^e$ and $R^f$;

$R^a$ $(C_1-C_6)$-alkyl or $(C_3-C_6)$-cycloalkyl, each of which is substituted by m radicals selected from the group consisting of fluorine, chlorine, bromine, iodine, cyano and hydroxy;

$R^b$ hydrogen, or $(C_1-C_6)$-alkyl or $(C_3-C_6)$-cycloalkyl, each of which is substituted by m radicals selected from the group consisting of fluorine, chlorine, bromine, iodine, cyano and hydroxy;

$R^c$ fluorine, chlorine, bromine, iodine, cyano, hydroxyl, $S(O)_nR^a$ or $(C_1-C_6)$-alkoxy, $(C_3-C_6)$-alkenyloxy or $(C_3-C_6)$-alkynyloxy, each of which is substituted by m radicals selected from the group consisting of fluorine, chlorine, bromine, cyano and $(C_1-C_2)$-alkoxy;

$R^e$ hydrogen or $(C_1-C_6)$-alkyl, $(C_3-C_6)$-cycloalkyl, $(C_2-C_4)$-alkenyl, phenyl-$(C_1-C_3)$-alkyl or $(C_2-C_4)$-alkynyl, each of which is substituted by m radicals selected from the group consisting of fluorine, chlorine, bromine, cyano and $(C_1-C_2)$-alkoxy;

$R^f$ $(C_1-C_3)$-alkyl or $(C_1-C_3)$-alkoxy;

$R^h$ hydrogen or $(C_1-C_6)$-alkyl, $(C_3-C_6)$-cycloalkyl, $(C_2-C_4)$-alkenyl, $(C_1-C_6)$-alkoxycarbonyl-$(C_1-C_6)$-alkyl, or $(C_2-C_4)$-alkynyl each of which is substituted by m radicals selected from the group consisting of fluorine, chlorine, bromine, cyano and $(C_1-C_2)$-alkoxy;

m 0, 1, 2, 3, 4 or 5;

n 0, 1 or 2;

r 1, 2, 3, 4, or 5.

Further preferred compounds of the present invention are compounds of formula (I), wherein the substituents have the following meanings:

$R^1$ hydrogen, $(C_1-C_3)$-alkyl, $(C_3-C_4)$-cycloalkyl, $(C_1-C_3)$-haloalkyl, $(C_2-C_3)$-alkenyl, $(C_2-C_3)$-haloalkenyl, $(C_2-C_3)$-alkynyl, $(C_2-C_3)$-haloalkynyl, $(C_1-C_3)$-alkoxy-$(C_1-C_3)$-alkyl, $(C_1-C_3)$-alkoxy, $(C_1-C_3)$-haloalkoxy;

$R^2$ hydrogen, halogen, $(C_1-C_3)$-alkyl, $(C_1-C_3)$-haloalkyl, $(C_1-C_3)$-alkoxy, $(C_1-C_3)$-haloalkoxy;

$R^3$ hydrogen, halogen, hydroxyl, cyano, $(C_1-C_3)$-alkyl, $(C_1-C_3)$-haloalkyl, $(C_3-C_5)$-halocycloalkyl, $(C_1-C_3)$-haloalkoxy, $(C_2-C_3)$-haloalkenyl, $(C_2-C_3)$-haloalkynyl;

$R^4$ hydrogen, halogen, hydroxyl, cyano, $(C_1-C_3)$-alkyl, $(C_1-C_3)$-haloalkyl, $(C_3-C_4)$-halocycloalkyl, $(C_1-C_3)$-haloalkoxy, $(C_2-C_3)$-haloalkenyl, $(C_2-C_3)$-haloalkynyl;

$R^5$ hydrogen, halogen, hydroxyl, cyano, $(C_1-C_3)$-alkyl, $(C_1-C_3)$-haloalkyl, $(C_3-C_5)$-halocycloalkyl, $(C_1-C_3)$-haloalkoxy, $(C_2-C_3)$-haloalkenyl, $(C_2-C_3)$-haloalkynyl;

$R^6$ hydrogen, halogen, $(C_1-C_3)$-alkyl, $(C_1-C_3)$-haloalkyl, $(C_1-C_3)$-alkoxy, $(C_1-C_3)$-haloalkoxy;

$R^7$ fluorine, cyano, or $(C_1-C_6)$-alkyl, $(C_3-C_6)$-cycloalkyl, $(C_2-C_6)$-alkenyl, $(C_2-C_6)$-alkynyl, $(C_1-C_6)$-alkoxy, each substituted by m radicals from the group consisting of fluorine, chlorine, bromine, iodine, hydroxyl, cyano and $(C_1-C_6)$-alkoxy;

X a bond;

Y Z;

Z four to five-membered saturated or partly unsaturated ring which is formed from r carbon atoms, n oxygen atoms, and which is substituted by m radicals from the group consisting of $CO_2R^e$, $CONR^bR^h$, $R^b$, $R^c$, $R^e$ and $R^f$;

$R^a$ $(C_1-C_6)$-alkyl or $(C_3-C_6)$-cycloalkyl, each of which is substituted by m radicals selected from the group consisting of fluorine, chlorine, bromine, iodine, cyano and hydroxy;

$R^b$ hydrogen, or $(C_1-C_6)$-alkyl or $(C_3-C_6)$-cycloalkyl, each of which is substituted by m radicals selected from the group consisting of fluorine, chlorine, bromine, iodine, cyano and hydroxy;

$R^c$ fluorine, chlorine, bromine, iodine, cyano, hydroxyl, $S(O)_nR^a$ or $(C_1-C_6)$-alkoxy, $(C_3-C_6)$-alkenyloxy or $(C_3-C_6)$-alkynyloxy, each of which is substituted by m radicals selected from the group consisting of fluorine, chlorine, bromine, cyano and $(C_1-C_2)$-alkoxy;

$R^e$ hydrogen or $(C_1-C_6)$-alkyl, $(C_3-C_6)$-cycloalkyl, $(C_2-C_4)$-alkenyl, phenyl-$(C_1-C_3)$-alkyl or $(C_2-C_4)$-alkynyl, each of which is substituted by m radicals selected from the group consisting of fluorine, chlorine, bromine, cyano and $(C_1-C_2)$-alkoxy;

$R^f$ $(C_1-C_3)$-alkyl or $(C_1-C_3)$-alkoxy;

$R^h$ hydrogen or $(C_1-C_6)$-alkyl, $(C_3-C_6)$-cycloalkyl, $(C_2-C_4)$-alkenyl, $(C_1-C_6)$-alkoxycarbonyl-$(C_1-C_6)$-alkyl, or $(C_2-C_4)$-alkynyl each of which is substituted by m radicals selected from the group consisting of fluorine, chlorine, bromine, cyano and $(C_1-C_2)$-alkoxy;

m 0, 1, 2, 3, 4 or 5;

n 0, 1 or 2;

r 1, 2, 3, 4, or 5.

Further preferred compounds of the present invention are compounds of formula (I), wherein the substituents have the following meanings:

$R^1$ hydrogen, $(C_1-C_3)$-alkyl, $(C_3-C_4)$-cycloalkyl, $(C_1-C_3)$-haloalkyl, $(C_2-C_3)$-alkenyl, $(C_2-C_3)$-haloalkenyl, $(C_2-C_3)$-alkynyl, $(C_2-C_3)$-haloalkynyl, $(C_1-C_3)$-alkoxy-$(C_1-C_3)$-alkyl, $(C_1-C_3)$-alkoxy, $(C_1-C_3)$-haloalkoxy;

$R^2$ hydrogen, halogen, $(C_1-C_3)$-alkyl, $(C_1-C_3)$-haloalkyl, $(C_1-C_3)$-alkoxy, $(C_1-C_3)$-haloalkoxy;

$R^3$ hydrogen, halogen, hydroxyl, cyano, $(C_1-C_3)$-alkyl, $(C_1-C_3)$-haloalkyl, $(C_3-C_5)$-halocycloalkyl, $(C_1-C_3)$-haloalkoxy, $(C_2-C_3)$-haloalkenyl, $(C_2-C_3)$-haloalkynyl;

$R^4$ hydrogen, halogen, hydroxyl, cyano, $(C_1-C_3)$-alkyl, $(C_1-C_3)$-haloalkyl, $(C_3-C_4)$-halocycloalkyl, $(C_1-C_3)$-haloalkoxy, $(C_2-C_3)$-haloalkenyl, $(C_2-C_3)$-haloalkynyl;

$R^5$ hydrogen, halogen, hydroxyl, cyano, $(C_1-C_3)$-alkyl, $(C_1-C_3)$-haloalkyl, $(C_3-C_4)$-halocycloalkyl, $(C_1-C_3)$-haloalkoxy, $(C_2-C_3)$-haloalkenyl, $(C_2-C_3)$-haloalkynyl;

$R^6$ hydrogen, halogen, $(C_1-C_3)$-alkyl, $(C_1-C_3)$-haloalkyl, $(C_1-C_3)$-alkoxy, $(C_1-C_3)$-haloalkoxy;

$R^7$ fluorine, cyano, or $(C_1-C_6)$-alkyl, $(C_3-C_6)$-cycloalkyl, $(C_2-C_6)$-alkenyl, $(C_2-C_6)$-alkynyl, $(C_1-C_6)$-alkoxy, each substituted by m radicals from the group consisting of fluorine, chlorine, bromine, iodine, hydroxyl, cyano and $(C_1-C_6)$-alkoxy;

X a bond;

Y $(C_1-C_{12})$-alkyl, $(C_3-C_8)$-cycloalkyl, $(C_2-C_{12})$-alkenyl or $(C_2-C_{12})$-alkynyl each substituted by m radicals from the group consisting of fluorine, chlorine, bromine, iodine, cyano, hydroxyl, $OR^d$, Z, OZ, NHZ, $S(O)_nR^a$, $SO_2NR^bR^d$, $SO_2NR^bCOR^e$, $CO_2R^e$, $CONR^bR^h$, $COR^b$, $CONR^eSO_2R^a$, $NR^bR^e$, $NR^bCOR^e$, $NR^bCONR^eR^e$, $NR^bCO_2R^e$, $NR^bSO_2R^e$ $NR^bSO_2NR^bR^e$, $OCONR^bR^e$, $OCSNR^bR^e$, $POR^fR^f$ and $C(R^b){=}NOR^e$;

Z a three-, four-, five- or six-membered saturated, partly unsaturated, fully unsaturated or aromatic ring, except phenyl, which is formed from r carbon atoms, n nitrogen atoms, n sulfur atoms and n oxygen atoms, and which is substituted by m radicals from the group consisting of $CO_2R^e$, $CONR^bR^h$, $R^b$, $R^c$, $R^e$ and $R^f$, and where the sulfur atoms and carbon atoms bear n oxo groups;

$R^a$ $(C_1-C_6)$-alkyl or $(C_3-C_6)$-cycloalkyl, each of which is substituted by m radicals selected from the group consisting of fluorine, chlorine, bromine, iodine, cyano and hydroxy;

$R^b$ hydrogen or $R^a$;

$R^c$ fluorine, chlorine, bromine, iodine, cyano, hydroxyl, $S(O)_nR^a$ or $(C_1-C_6)$-alkoxy, $(C_3-C_6)$-alkenyloxy or $(C_3-C_6)$-alkynyloxy, each of which is substituted by m radicals selected from the group consisting of fluorine, chlorine, bromine, cyano and $(C_1-C_2)$-alkoxy;

$R^d$ hydrogen or $(C_1-C_6)$-alkyl, $(C_3-C_6)$-cycloalkyl, $(C_2-C_4)$-alkenyl, phenyl-$(C_1-C_3)$-alkyl or $(C_2-C_4)$-alkynyl, each of which is substituted by m radicals selected from the group consisting of fluorine, chlorine, bromine, cyano and $(C_1-C_2)$-alkoxy;

$R^e$ $R^d$ $R^f$ $(C_1-C_3)$-alkyl or $(C_1-C_3)$-alkoxy;

$R^h$ hydrogen or $(C_1-C_6)$-alkyl, $(C_3-C_6)$-cycloalkyl, $(C_2-C_4)$-alkenyl, $(C_1-C_6)$-alkoxycarbonyl-$(C_1-C_6)$-alkyl, or $(C_2-C_4)$-alkynyl each of which is substituted by m radicals selected from the group consisting of fluorine, chlorine, bromine, cyano and $(C_1-C_2)$-alkoxy;

r 1, 2, 3, 4, 5 or 6;

m 0, 1, 2, 3, 4 or 5;

n 0, 1 or 2.

Further preferred compounds of the present invention are compounds of formula (I), wherein the substituents have the following meanings:

$R^1$ hydrogen;

$R^2$ hydrogen;

$R^3$ halogen;

$R^4$ hydrogen;

$R^5$ halogen;

$R^6$ hydrogen;

$R^7$ $(C_1-C_2)$-alkyl, cyclopropyl, $(C_1-C_2)$-haloalkyl, $(C_2-C_3)$-alkenyl, $(C_1-C_2)$-alkoxy;

X a bond;

Y Z, or $(C_1-C_3)$-alkyl, $(C_3-C_8)$-cycloalkyl, $(C_2-C_8)$-alkenyl or $(C_2-C_8)$-alkynyl, each substituted by m radicals from the group consisting of fluorine and $CO_2R^e$;

Z four to five-membered saturated or partly unsaturated ring which is formed from r carbon atoms, n oxygen atoms, and which is substituted by m radicals from the group consisting of $CO_2R^e$;

$R^e$ hydrogen or $(C_1-C_6)$-alkyl, $(C_3-C_6)$-cycloalkyl, $(C_2-C_4)$-alkenyl, phenyl-$(C_1-C_3)$-alkyl or $(C_2-C_4)$-alkynyl, each of which is substituted by m radicals selected from the group consisting of fluorine, chlorine, bromine, cyano and $(C_1-C_2)$-alkoxy;

r 4, or 5;

m 0, 1, 2, 3, 4 or 5;

n 0 or 1.

Further preferred embodiments (1.1 and 1.11) of compounds of formula (I) are compounds, wherein (I.I): $R^1$ is hydrogen:

(I.I)

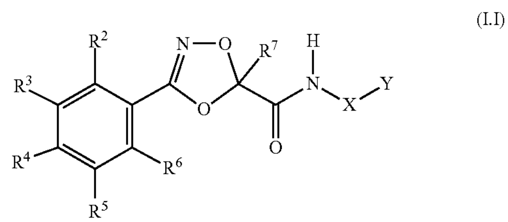

(I.II): $R^1$ is methyl:

(I.II)

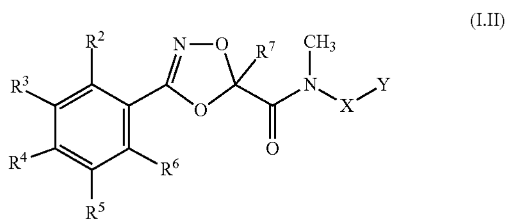

Compounds of formula (I.I.a.) wherein $R^1$, $R^2$, and $R^6$ are hydrogen are particularly preferred:

(I.I.a)

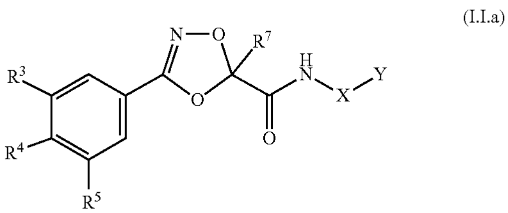

Compounds of formula (I.I.b.) wherein $R^1$, $R^2$, $R^4$, and $R^6$ are hydrogen are also particularly preferred:

(I.I.b)

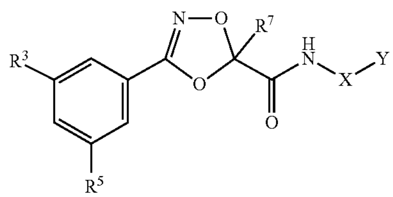

Compounds of formula (I.I.c.) wherein $R^1$, $R^2$, and $R^6$ are hydrogen, X is a bond ($X^0$), and Y is Z are particularly preferred:

(I.I.c)

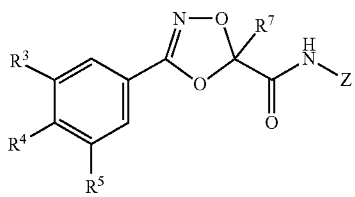

Compounds of formula (I.I.d.) wherein $R^1$, $R^2$, $R^4$, and $R^6$ are hydrogen, X is a bond ($X^0$), and Y is Z are also particularly preferred:

(I.I.d)

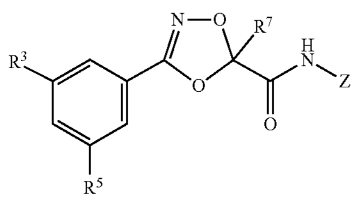

Compounds of formula (I.II.a.) wherein $R^2$ and $R^6$ are hydrogen and $R^1$ is methyl are also particularly preferred:

(I.II.a)

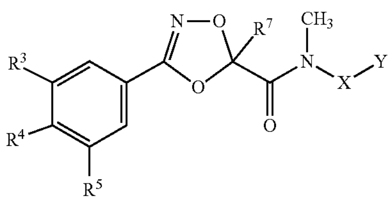

Compounds of formula (I.II.b.) wherein $R^2$, $R^4$, and $R^6$ are hydrogen and $R^1$ is methyl are also particularly preferred:

(I.II.b)

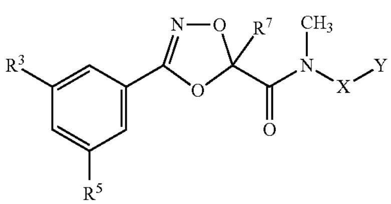

In the context of the present invention, compounds wherein $R^1$, $R^2$, and $R^6$ are hydrogen and $R^3$, $R^4$, $R^5$ and $R^7$ have the meanings as defined lines in 1 to 768 of Table 1 below, are particularly preferred.

TABLE 1

| Cpd. | $R^3$ | $R^4$ | $R^5$ | $R^7$ |
|---|---|---|---|---|
| 1. | H | H | H | $CH_3$ |
| 2. | F | H | H | $CH_3$ |
| 3. | Cl | H | H | $CH_3$ |
| 4. | Br | H | H | $CH_3$ |
| 5. | CN | H | H | $CH_3$ |
| 6. | $CH_3$ | H | H | $CH_3$ |
| 7. | $CF_3$ | H | H | $CH_3$ |
| 8. | $OCH_3$ | H | H | $CH_3$ |
| 9. | H | F | H | $CH_3$ |
| 10. | F | F | H | $CH_3$ |
| 11. | Cl | F | H | $CH_3$ |
| 12. | Br | F | H | $CH_3$ |
| 13. | CN | F | H | $CH_3$ |
| 14. | $CH_3$ | F | H | $CH_3$ |
| 15. | $CF_3$ | F | H | $CH_3$ |
| 16. | $OCH_3$ | F | H | $CH_3$ |
| 17. | H | H | F | $CH_3$ |
| 18. | F | H | F | $CH_3$ |
| 19. | Cl | H | F | $CH_3$ |
| 20. | Br | H | F | $CH_3$ |
| 21. | CN | H | F | $CH_3$ |
| 22. | $CH_3$ | H | F | $CH_3$ |
| 23. | $CF_3$ | H | F | $CH_3$ |
| 24. | $OCH_3$ | H | F | $CH_3$ |
| 25. | H | F | F | $CH_3$ |
| 26. | F | F | F | $CH_3$ |
| 27. | Cl | F | F | $CH_3$ |
| 28. | Br | F | F | $CH_3$ |
| 29. | CN | F | F | $CH_3$ |
| 30. | $CH_3$ | F | F | $CH_3$ |
| 31. | $CF_3$ | F | F | $CH_3$ |
| 32. | $OCH_3$ | F | F | $CH_3$ |
| 33. | H | H | Cl | $CH_3$ |
| 34. | F | H | Cl | $CH_3$ |
| 35. | Cl | H | Cl | $CH_3$ |
| 36. | Br | H | Cl | $CH_3$ |
| 37. | CN | H | Cl | $CH_3$ |
| 38. | $CH_3$ | H | Cl | $CH_3$ |
| 39. | $CF_3$ | H | Cl | $CH_3$ |
| 40. | $OCH_3$ | H | Cl | $CH_3$ |
| 41. | H | F | Cl | $CH_3$ |
| 42. | F | F | Cl | $CH_3$ |
| 43. | Cl | F | Cl | $CH_3$ |
| 44. | Br | F | Cl | $CH_3$ |
| 45. | CN | F | Cl | $CH_3$ |
| 46. | $CH_3$ | F | Cl | $CH_3$ |
| 47. | $CF_3$ | F | Cl | $CH_3$ |
| 48. | $OCH_3$ | F | Cl | $CH_3$ |
| 49. | H | H | Br | $CH_3$ |
| 50. | F | H | Br | $CH_3$ |
| 51. | Cl | H | Br | $CH_3$ |
| 52. | Br | H | Br | $CH_3$ |
| 53. | CN | H | Br | $CH_3$ |
| 54. | $CH_3$ | H | Br | $CH_3$ |
| 55. | $CF_3$ | H | Br | $CH_3$ |
| 56. | $OCH_3$ | H | Br | $CH_3$ |
| 57. | H | F | Br | $CH_3$ |
| 58. | F | F | Br | $CH_3$ |
| 59. | Cl | F | Br | $CH_3$ |
| 60. | Br | F | Br | $CH_3$ |
| 61. | CN | F | Br | $CH_3$ |
| 62. | $CH_3$ | F | Br | $CH_3$ |
| 63. | $CF_3$ | F | Br | $CH_3$ |
| 64. | $OCH_3$ | F | Br | $CH_3$ |
| 65. | H | H | CN | $CH_3$ |
| 66. | F | H | CN | $CH_3$ |
| 67. | Cl | H | CN | $CH_3$ |
| 68. | Br | H | CN | $CH_3$ |
| 69. | CN | H | CN | $CH_3$ |
| 70. | $CH_3$ | H | CN | $CH_3$ |
| 71. | $CF_3$ | H | CN | $CH_3$ |
| 72. | $OCH_3$ | H | CN | $CH_3$ |

TABLE 1-continued

| Cpd. | $R^3$ | $R^4$ | $R^5$ | $R^7$ |
|---|---|---|---|---|
| 73. | H | F | CN | $CH_3$ |
| 74. | F | F | CN | $CH_3$ |
| 75. | Cl | F | CN | $CH_3$ |
| 76. | Br | F | CN | $CH_3$ |
| 77. | CN | F | CN | $CH_3$ |
| 78. | $CH_3$ | F | CN | $CH_3$ |
| 79. | $CF_3$ | F | CN | $CH_3$ |
| 80. | $OCH_3$ | F | CN | $CH_3$ |
| 81. | H | H | $CH_3$ | $CH_3$ |
| 82. | F | H | $CH_3$ | $CH_3$ |
| 83. | Cl | H | $CH_3$ | $CH_3$ |
| 84. | Br | H | $CH_3$ | $CH_3$ |
| 85. | CN | H | $CH_3$ | $CH_3$ |
| 86. | $CH_3$ | H | $CH_3$ | $CH_3$ |
| 87. | $CF_3$ | H | $CH_3$ | $CH_3$ |
| 88. | $OCH_3$ | H | $CH_3$ | $CH_3$ |
| 89. | H | F | $CH_3$ | $CH_3$ |
| 90. | F | F | $CH_3$ | $CH_3$ |
| 91. | Cl | F | $CH_3$ | $CH_3$ |
| 92. | Br | F | $CH_3$ | $CH_3$ |
| 93. | CN | F | $CH_3$ | $CH_3$ |
| 94. | $CH_3$ | F | $CH_3$ | $CH_3$ |
| 95. | $CF_3$ | F | $CH_3$ | $CH_3$ |
| 96. | $OCH_3$ | F | $CH_3$ | $CH_3$ |
| 97. | H | H | $CF_3$ | $CH_3$ |
| 98. | F | H | $CF_3$ | $CH_3$ |
| 99. | Cl | H | $CF_3$ | $CH_3$ |
| 100. | Br | H | $CF_3$ | $CH_3$ |
| 101. | CN | H | $CF_3$ | $CH_3$ |
| 102. | $CH_3$ | H | $CF_3$ | $CH_3$ |
| 103. | $CF_3$ | H | $CF_3$ | $CH_3$ |
| 104. | $OCH_3$ | H | $CF_3$ | $CH_3$ |
| 105. | H | F | $CF_3$ | $CH_3$ |
| 106. | F | F | $CF_3$ | $CH_3$ |
| 107. | Cl | F | $CF_3$ | $CH_3$ |
| 108. | Br | F | $CF_3$ | $CH_3$ |
| 109. | CN | F | $CF_3$ | $CH_3$ |
| 110. | $CH_3$ | F | $CF_3$ | $CH_3$ |
| 111. | $CF_3$ | F | $CF_3$ | $CH_3$ |
| 112. | $OCH_3$ | F | $CF_3$ | $CH_3$ |
| 113. | H | H | $OCH_3$ | $CH_3$ |
| 114. | F | H | $OCH_3$ | $CH_3$ |
| 115. | Cl | H | $OCH_3$ | $CH_3$ |
| 116. | Br | H | $OCH_3$ | $CH_3$ |
| 117. | CN | H | $OCH_3$ | $CH_3$ |
| 118. | $CH_3$ | H | $OCH_3$ | $CH_3$ |
| 119. | $CF_3$ | H | $OCH_3$ | $CH_3$ |
| 120. | $OCH_3$ | H | $OCH_3$ | $CH_3$ |
| 121. | H | F | $OCH_3$ | $CH_3$ |
| 122. | F | F | $OCH_3$ | $CH_3$ |
| 123. | Cl | F | $OCH_3$ | $CH_3$ |
| 124. | Br | F | $OCH_3$ | $CH_3$ |
| 125. | CN | F | $OCH_3$ | $CH_3$ |
| 126. | $CH_3$ | F | $OCH_3$ | $CH_3$ |
| 127. | $CF_3$ | F | $OCH_3$ | $CH_3$ |
| 128. | $OCH_3$ | F | $OCH_3$ | $CH_3$ |
| 129. | H | H | H | $CHCH_2$ |
| 130. | F | H | H | $CHCH_2$ |
| 131. | Cl | H | H | $CHCH_2$ |
| 132. | Br | H | H | $CHCH_2$ |
| 133. | CN | H | H | $CHCH_2$ |
| 134. | $CH_3$ | H | H | $CHCH_2$ |
| 135. | $CF_3$ | H | H | $CHCH_2$ |
| 136. | $OCH_3$ | H | H | $CHCH_2$ |
| 137. | H | F | H | $CHCH_2$ |
| 138. | F | F | H | $CHCH_2$ |
| 139. | Cl | F | H | $CHCH_2$ |
| 140. | Br | F | H | $CHCH_2$ |
| 141. | CN | F | H | $CHCH_2$ |
| 142. | $CH_3$ | F | H | $CHCH_2$ |
| 143. | $CF_3$ | F | H | $CHCH_2$ |
| 144. | $OCH_3$ | F | H | $CHCH_2$ |
| 145. | H | H | F | $CHCH_2$ |
| 146. | F | H | F | $CHCH_2$ |
| 147. | Cl | H | F | $CHCH_2$ |
| 148. | Br | H | F | $CHCH_2$ |
| 149. | CN | H | F | $CHCH_2$ |
| 150. | $CH_3$ | H | F | $CHCH_2$ |

TABLE 1-continued

| Cpd. | $R^3$ | $R^4$ | $R^5$ | $R^7$ |
|---|---|---|---|---|
| 151. | $CF_3$ | H | F | $CHCH_2$ |
| 152. | $OCH_3$ | H | F | $CHCH_2$ |
| 153. | H | F | F | $CHCH_2$ |
| 154. | F | F | F | $CHCH_2$ |
| 155. | Cl | F | F | $CHCH_2$ |
| 156. | Br | F | F | $CHCH_2$ |
| 157. | CN | F | F | $CHCH_2$ |
| 158. | $CH_3$ | F | F | $CHCH_2$ |
| 159. | $CF_3$ | F | F | $CHCH_2$ |
| 160. | $OCH_3$ | F | F | $CHCH_2$ |
| 161. | H | H | Cl | $CHCH_2$ |
| 162. | F | H | Cl | $CHCH_2$ |
| 163. | Cl | H | Cl | $CHCH_2$ |
| 164. | Br | H | Cl | $CHCH_2$ |
| 165. | CN | H | Cl | $CHCH_2$ |
| 166. | $CH_3$ | H | Cl | $CHCH_2$ |
| 167. | $CF_3$ | H | Cl | $CHCH_2$ |
| 168. | $OCH_3$ | H | Cl | $CHCH_2$ |
| 169. | H | F | Cl | $CHCH_2$ |
| 170. | F | F | Cl | $CHCH_2$ |
| 171. | Cl | F | Cl | $CHCH_2$ |
| 172. | Br | F | Cl | $CHCH_2$ |
| 173. | CN | F | Cl | $CHCH_2$ |
| 174. | $CH_3$ | F | Cl | $CHCH_2$ |
| 175. | $CF_3$ | F | Cl | $CHCH_2$ |
| 176. | $OCH_3$ | F | Cl | $CHCH_2$ |
| 177. | H | H | Br | $CHCH_2$ |
| 178. | F | H | Br | $CHCH_2$ |
| 179. | Cl | H | Br | $CHCH_2$ |
| 180. | Br | H | Br | $CHCH_2$ |
| 181. | CN | H | Br | $CHCH_2$ |
| 182. | $CH_3$ | H | Br | $CHCH_2$ |
| 183. | $CF_3$ | H | Br | $CHCH_2$ |
| 184. | $OCH_3$ | H | Br | $CHCH_2$ |
| 185. | H | F | Br | $CHCH_2$ |
| 186. | F | F | Br | $CHCH_2$ |
| 187. | Cl | F | Br | $CHCH_2$ |
| 188. | Br | F | Br | $CHCH_2$ |
| 189. | CN | F | Br | $CHCH_2$ |
| 190. | $CH_3$ | F | Br | $CHCH_2$ |
| 191. | $CF_3$ | F | Br | $CHCH_2$ |
| 192. | $OCH_3$ | F | Br | $CHCH_2$ |
| 193. | H | H | CN | $CHCH_2$ |
| 194. | F | H | CN | $CHCH_2$ |
| 195. | Cl | H | CN | $CHCH_2$ |
| 196. | Br | H | CN | $CHCH_2$ |
| 197. | CN | H | CN | $CHCH_2$ |
| 198. | $CH_3$ | H | CN | $CHCH_2$ |
| 199. | $CF_3$ | H | CN | $CHCH_2$ |
| 200. | $OCH_3$ | H | CN | $CHCH_2$ |
| 201. | H | F | CN | $CHCH_2$ |
| 202. | F | F | CN | $CHCH_2$ |
| 203. | Cl | F | CN | $CHCH_2$ |
| 204. | Br | F | CN | $CHCH_2$ |
| 205. | CN | F | CN | $CHCH_2$ |
| 206. | $CH_3$ | F | CN | $CHCH_2$ |
| 207. | $CF_3$ | F | CN | $CHCH_2$ |
| 208. | $OCH_3$ | F | CN | $CHCH_2$ |
| 209. | H | H | $CH_3$ | $CHCH_2$ |
| 210. | F | H | $CH_3$ | $CHCH_2$ |
| 211. | Cl | H | $CH_3$ | $CHCH_2$ |
| 212. | Br | H | $CH_3$ | $CHCH_2$ |
| 213. | CN | H | $CH_3$ | $CHCH_2$ |
| 214. | $CH_3$ | H | $CH_3$ | $CHCH_2$ |
| 215. | $CF_3$ | H | $CH_3$ | $CHCH_2$ |
| 216. | $OCH_3$ | H | $CH_3$ | $CHCH_2$ |
| 217. | H | F | $CH_3$ | $CHCH_2$ |
| 218. | F | F | $CH_3$ | $CHCH_2$ |
| 219. | Cl | F | $CH_3$ | $CHCH_2$ |
| 220. | Br | F | $CH_3$ | $CHCH_2$ |
| 221. | CN | F | $CH_3$ | $CHCH_2$ |
| 222. | $CH_3$ | F | $CH_3$ | $CHCH_2$ |
| 223. | $CF_3$ | F | $CH_3$ | $CHCH_2$ |
| 224. | $OCH_3$ | F | $CH_3$ | $CHCH_2$ |
| 225. | H | H | $CF_3$ | $CHCH_2$ |
| 226. | F | H | $CF_3$ | $CHCH_2$ |
| 227. | Cl | H | $CF_3$ | $CHCH_2$ |
| 228. | Br | H | $CF_3$ | $CHCH_2$ |

TABLE 1-continued

| Cpd. | $R^3$ | $R^4$ | $R^5$ | $R^7$ |
|---|---|---|---|---|
| 229. | CN | H | $CF_3$ | $CHCH_2$ |
| 230. | $CH_3$ | H | $CF_3$ | $CHCH_2$ |
| 231. | $CF_3$ | H | $CF_3$ | $CHCH_2$ |
| 232. | $OCH_3$ | H | $CF_3$ | $CHCH_2$ |
| 233. | H | F | $CF_3$ | $CHCH_2$ |
| 234. | F | F | $CF_3$ | $CHCH_2$ |
| 235. | Cl | F | $CF_3$ | $CHCH_2$ |
| 236. | Br | F | $CF_3$ | $CHCH_2$ |
| 237. | CN | F | $CF_3$ | $CHCH_2$ |
| 238. | $CH_3$ | F | $CF_3$ | $CHCH_2$ |
| 239. | $CF_3$ | F | $CF_3$ | $CHCH_2$ |
| 240. | $OCH_3$ | F | $CF_3$ | $CHCH_2$ |
| 241. | H | H | $OCH_3$ | $CHCH_2$ |
| 242. | F | H | $OCH_3$ | $CHCH_2$ |
| 243. | Cl | H | $OCH_3$ | $CHCH_2$ |
| 244. | Br | H | $OCH_3$ | $CHCH_2$ |
| 245. | CN | H | $OCH_3$ | $CHCH_2$ |
| 246. | $CH_3$ | H | $OCH_3$ | $CHCH_2$ |
| 247. | $CF_3$ | H | $OCH_3$ | $CHCH_2$ |
| 248. | $OCH_3$ | H | $OCH_3$ | $CHCH_2$ |
| 249. | H | F | $OCH_3$ | $CHCH_2$ |
| 250. | F | F | $OCH_3$ | $CHCH_2$ |
| 251. | Cl | F | $OCH_3$ | $CHCH_2$ |
| 252. | Br | F | $OCH_3$ | $CHCH_2$ |
| 253. | CN | F | $OCH_3$ | $CHCH_2$ |
| 254. | $CH_3$ | F | $OCH_3$ | $CHCH_2$ |
| 255. | $CF_3$ | F | $OCH_3$ | $CHCH_2$ |
| 256. | $OCH_3$ | F | $OCH_3$ | $CHCH_2$ |
| 257. | H | H | H | $CH_2Cl$ |
| 258. | F | H | H | $CH_2Cl$ |
| 259. | Cl | H | H | $CH_2Cl$ |
| 260. | Br | H | H | $CH_2Cl$ |
| 261. | CN | H | H | $CH_2Cl$ |
| 262. | $CH_3$ | H | H | $CH_2Cl$ |
| 263. | $CF_3$ | H | H | $CH_2Cl$ |
| 264. | $OCH_3$ | H | H | $CH_2Cl$ |
| 265. | H | F | H | $CH_2Cl$ |
| 266. | F | F | H | $CH_2Cl$ |
| 267. | Cl | F | H | $CH_2Cl$ |
| 268. | Br | F | H | $CH_2Cl$ |
| 269. | CN | F | H | $CH_2Cl$ |
| 270. | $CH_3$ | F | H | $CH_2Cl$ |
| 271. | $CF_3$ | F | H | $CH_2Cl$ |
| 272. | $OCH_3$ | F | H | $CH_2Cl$ |
| 273. | H | H | F | $CH_2Cl$ |
| 274. | F | H | F | $CH_2Cl$ |
| 275. | Cl | H | F | $CH_2Cl$ |
| 276. | Br | H | F | $CH_2Cl$ |
| 277. | CN | H | F | $CH_2Cl$ |
| 278. | $CH_3$ | H | F | $CH_2Cl$ |
| 279. | $CF_3$ | H | F | $CH_2Cl$ |
| 280. | $OCH_3$ | H | F | $CH_2Cl$ |
| 281. | H | F | F | $CH_2Cl$ |
| 282. | F | F | F | $CH_2Cl$ |
| 283. | Cl | F | F | $CH_2Cl$ |
| 284. | Br | F | F | $CH_2Cl$ |
| 285. | CN | F | F | $CH_2Cl$ |
| 286. | $CH_3$ | F | F | $CH_2Cl$ |
| 287. | $CF_3$ | F | F | $CH_2Cl$ |
| 288. | $OCH_3$ | F | F | $CH_2Cl$ |
| 289. | H | H | Cl | $CH_2Cl$ |
| 290. | F | H | Cl | $CH_2Cl$ |
| 291. | Cl | H | Cl | $CH_2Cl$ |
| 292. | Br | H | Cl | $CH_2Cl$ |
| 293. | CN | H | Cl | $CH_2Cl$ |
| 294. | $CH_3$ | H | Cl | $CH_2Cl$ |
| 295. | $CF_3$ | H | Cl | $CH_2Cl$ |
| 296. | $OCH_3$ | H | Cl | $CH_2Cl$ |
| 297. | H | F | Cl | $CH_2Cl$ |
| 298. | F | F | Cl | $CH_2Cl$ |
| 299. | Cl | F | Cl | $CH_2Cl$ |
| 300. | Br | F | Cl | $CH_2Cl$ |
| 301. | CN | F | Cl | $CH_2Cl$ |
| 302. | $CH_3$ | F | Cl | $CH_2Cl$ |
| 303. | $CF_3$ | F | Cl | $CH_2Cl$ |
| 304. | $OCH_3$ | F | Cl | $CH_2Cl$ |
| 305. | H | H | Br | $CH_2Cl$ |
| 306. | F | H | Br | $CH_2Cl$ |

TABLE 1-continued

| Cpd. | $R^3$ | $R^4$ | $R^5$ | $R^7$ |
|---|---|---|---|---|
| 307. | Cl | H | Br | $CH_2Cl$ |
| 308. | Br | H | Br | $CH_2Cl$ |
| 309. | CN | H | Br | $CH_2Cl$ |
| 310. | $CH_3$ | H | Br | $CH_2Cl$ |
| 311. | $CF_3$ | H | Br | $CH_2Cl$ |
| 312. | $OCH_3$ | H | Br | $CH_2Cl$ |
| 313. | H | F | Br | $CH_2Cl$ |
| 314. | F | F | Br | $CH_2Cl$ |
| 315. | Cl | F | Br | $CH_2Cl$ |
| 316. | Br | F | Br | $CH_2Cl$ |
| 317. | CN | F | Br | $CH_2Cl$ |
| 318. | $CH_3$ | F | Br | $CH_2Cl$ |
| 319. | $CF_3$ | F | Br | $CH_2Cl$ |
| 320. | $OCH_3$ | F | Br | $CH_2Cl$ |
| 321. | H | H | CN | $CH_2Cl$ |
| 322. | F | H | CN | $CH_2Cl$ |
| 323. | Cl | H | CN | $CH_2Cl$ |
| 324. | Br | H | CN | $CH_2Cl$ |
| 325. | CN | H | CN | $CH_2Cl$ |
| 326. | $CH_3$ | H | CN | $CH_2Cl$ |
| 327. | $CF_3$ | H | CN | $CH_2Cl$ |
| 328. | $OCH_3$ | H | CN | $CH_2Cl$ |
| 329. | H | F | CN | $CH_2Cl$ |
| 330. | F | F | CN | $CH_2Cl$ |
| 331. | Cl | F | CN | $CH_2Cl$ |
| 332. | Br | F | CN | $CH_2Cl$ |
| 333. | CN | F | CN | $CH_2Cl$ |
| 334. | $CH_3$ | F | CN | $CH_2Cl$ |
| 335. | $CF_3$ | F | CN | $CH_2Cl$ |
| 336. | $OCH_3$ | F | CN | $CH_2Cl$ |
| 337. | H | H | $CH_3$ | $CH_2Cl$ |
| 338. | F | H | $CH_3$ | $CH_2Cl$ |
| 339. | Cl | H | $CH_3$ | $CH_2Cl$ |
| 340. | Br | H | $CH_3$ | $CH_2Cl$ |
| 341. | CN | H | $CH_3$ | $CH_2Cl$ |
| 342. | $CH_3$ | H | $CH_3$ | $CH_2Cl$ |
| 343. | $CF_3$ | H | $CH_3$ | $CH_2Cl$ |
| 344. | $OCH_3$ | H | $CH_3$ | $CH_2Cl$ |
| 345. | H | F | $CH_3$ | $CH_2Cl$ |
| 346. | F | F | $CH_3$ | $CH_2Cl$ |
| 347. | Cl | F | $CH_3$ | $CH_2Cl$ |
| 348. | Br | F | $CH_3$ | $CH_2Cl$ |
| 349. | CN | F | $CH_3$ | $CH_2Cl$ |
| 350. | $CH_3$ | F | $CH_3$ | $CH_2Cl$ |
| 351. | $CF_3$ | F | $CH_3$ | $CH_2Cl$ |
| 352. | $OCH_3$ | F | $CH_3$ | $CH_2Cl$ |
| 353. | H | H | $CF_3$ | $CH_2Cl$ |
| 354. | F | H | $CF_3$ | $CH_2Cl$ |
| 355. | Cl | H | $CF_3$ | $CH_2Cl$ |
| 356. | Br | H | $CF_3$ | $CH_2Cl$ |
| 357. | CN | H | $CF_3$ | $CH_2Cl$ |
| 358. | $CH_3$ | H | $CF_3$ | $CH_2Cl$ |
| 359. | $CF_3$ | H | $CF_3$ | $CH_2Cl$ |
| 360. | $OCH_3$ | H | $CF_3$ | $CH_2Cl$ |
| 361. | H | F | $CF_3$ | $CH_2Cl$ |
| 362. | F | F | $CF_3$ | $CH_2Cl$ |
| 363. | Cl | F | $CF_3$ | $CH_2Cl$ |
| 364. | Br | F | $CF_3$ | $CH_2Cl$ |
| 365. | CN | F | $CF_3$ | $CH_2Cl$ |
| 366. | $CH_3$ | F | $CF_3$ | $CH_2Cl$ |
| 367. | $CF_3$ | F | $CF_3$ | $CH_2Cl$ |
| 368. | $OCH_3$ | F | $CF_3$ | $CH_2Cl$ |
| 369. | H | H | $OCH_3$ | $CH_2Cl$ |
| 370. | F | H | $OCH_3$ | $CH_2Cl$ |
| 371. | Cl | H | $OCH_3$ | $CH_2Cl$ |
| 372. | Br | H | $OCH_3$ | $CH_2Cl$ |
| 373. | CN | H | $OCH_3$ | $CH_2Cl$ |
| 374. | $CH_3$ | H | $OCH_3$ | $CH_2Cl$ |
| 375. | $CF_3$ | H | $OCH_3$ | $CH_2Cl$ |
| 376. | $OCH_3$ | H | $OCH_3$ | $CH_2Cl$ |
| 377. | H | F | $OCH_3$ | $CH_2Cl$ |
| 378. | F | F | $OCH_3$ | $CH_2Cl$ |
| 379. | Cl | F | $OCH_3$ | $CH_2Cl$ |
| 380. | Br | F | $OCH_3$ | $CH_2Cl$ |
| 381. | CN | F | $OCH_3$ | $CH_2Cl$ |
| 382. | $CH_3$ | F | $OCH_3$ | $CH_2Cl$ |
| 383. | $CF_3$ | F | $OCH_3$ | $CH_2Cl$ |
| 384. | $OCH_3$ | F | $OCH_3$ | $CH_2Cl$ |

TABLE 1-continued

| Cpd. | $R^3$ | $R^4$ | $R^5$ | $R^7$ |
|---|---|---|---|---|
| 385. | H | H | H | $CF_3$ |
| 386. | F | H | H | $CF_3$ |
| 387. | Cl | H | H | $CF_3$ |
| 388. | Br | H | H | $CF_3$ |
| 389. | CN | H | H | $CF_3$ |
| 390. | $CH_3$ | H | H | $CF_3$ |
| 391. | $CF_3$ | H | H | $CF_3$ |
| 392. | $OCH_3$ | H | H | $CF_3$ |
| 393. | H | F | H | $CF_3$ |
| 394. | F | F | H | $CF_3$ |
| 395. | Cl | F | H | $CF_3$ |
| 396. | Br | F | H | $CF_3$ |
| 397. | CN | F | H | $CF_3$ |
| 398. | $CH_3$ | F | H | $CF_3$ |
| 399. | $CF_3$ | F | H | $CF_3$ |
| 400. | $OCH_3$ | F | H | $CF_3$ |
| 401. | H | H | F | $CF_3$ |
| 402. | F | H | F | $CF_3$ |
| 403. | Cl | H | F | $CF_3$ |
| 404. | Br | H | F | $CF_3$ |
| 405. | CN | H | F | $CF_3$ |
| 406. | $CH_3$ | H | F | $CF_3$ |
| 407. | $CF_3$ | H | F | $CF_3$ |
| 408. | $OCH_3$ | H | F | $CF_3$ |
| 409. | H | F | F | $CF_3$ |
| 410. | F | F | F | $CF_3$ |
| 411. | Cl | F | F | $CF_3$ |
| 412. | Br | F | F | $CF_3$ |
| 413. | CN | F | F | $CF_3$ |
| 414. | $CH_3$ | F | F | $CF_3$ |
| 415. | $CF_3$ | F | F | $CF_3$ |
| 416. | $OCH_3$ | F | F | $CF_3$ |
| 417. | H | H | Cl | $CF_3$ |
| 418. | F | H | Cl | $CF_3$ |
| 419. | Cl | H | Cl | $CF_3$ |
| 420. | Br | H | Cl | $CF_3$ |
| 421. | CN | H | Cl | $CF_3$ |
| 422. | $CH_3$ | H | Cl | $CF_3$ |
| 423. | $CF_3$ | H | Cl | $CF_3$ |
| 424. | $OCH_3$ | H | Cl | $CF_3$ |
| 425. | H | F | Cl | $CF_3$ |
| 426. | F | F | Cl | $CF_3$ |
| 427. | Cl | F | Cl | $CF_3$ |
| 428. | Br | F | Cl | $CF_3$ |
| 429. | CN | F | Cl | $CF_3$ |
| 430. | $CH_3$ | F | Cl | $CF_3$ |
| 431. | $CF_3$ | F | Cl | $CF_3$ |
| 432. | $OCH_3$ | F | Cl | $CF_3$ |
| 433. | H | H | Br | $CF_3$ |
| 434. | F | H | Br | $CF_3$ |
| 435. | Cl | H | Br | $CF_3$ |
| 436. | Br | H | Br | $CF_3$ |
| 437. | CN | H | Br | $CF_3$ |
| 438. | $CH_3$ | H | Br | $CF_3$ |
| 439. | $CF_3$ | H | Br | $CF_3$ |
| 440. | $OCH_3$ | H | Br | $CF_3$ |
| 441. | H | F | Br | $CF_3$ |
| 442. | F | F | Br | $CF_3$ |
| 443. | Cl | F | Br | $CF_3$ |
| 444. | Br | F | Br | $CF_3$ |
| 445. | CN | F | Br | $CF_3$ |
| 446. | $CH_3$ | F | Br | $CF_3$ |
| 447. | $CF_3$ | F | Br | $CF_3$ |
| 448. | $OCH_3$ | F | Br | $CF_3$ |
| 449. | H | H | CN | $CF_3$ |
| 450. | F | H | CN | $CF_3$ |
| 451. | Cl | H | CN | $CF_3$ |
| 452. | Br | H | CN | $CF_3$ |
| 453. | CN | H | CN | $CF_3$ |
| 454. | $CH_3$ | H | CN | $CF_3$ |
| 455. | $CF_3$ | H | CN | $CF_3$ |
| 456. | $OCH_3$ | H | CN | $CF_3$ |
| 457. | H | F | CN | $CF_3$ |
| 458. | F | F | CN | $CF_3$ |
| 459. | Cl | F | CN | $CF_3$ |
| 460. | Br | F | CN | $CF_3$ |
| 461. | CN | F | CN | $CF_3$ |
| 462. | $CH_3$ | F | CN | $CF_3$ |

TABLE 1-continued

| Cpd. | $R^3$ | $R^4$ | $R^5$ | $R^7$ |
|---|---|---|---|---|
| 463. | $CF_3$ | F | CN | $CF_3$ |
| 464. | $OCH_3$ | F | CN | $CF_3$ |
| 465. | H | H | $CH_3$ | $CF_3$ |
| 466. | F | H | $CH_3$ | $CF_3$ |
| 467. | Cl | H | $CH_3$ | $CF_3$ |
| 468. | Br | H | $CH_3$ | $CF_3$ |
| 469. | CN | H | $CH_3$ | $CF_3$ |
| 470. | $CH_3$ | H | $CH_3$ | $CF_3$ |
| 471. | $CF_3$ | H | $CH_3$ | $CF_3$ |
| 472. | $OCH_3$ | H | $CH_3$ | $CF_3$ |
| 473. | H | F | $CH_3$ | $CF_3$ |
| 474. | F | F | $CH_3$ | $CF_3$ |
| 475. | Cl | F | $CH_3$ | $CF_3$ |
| 476. | Br | F | $CH_3$ | $CF_3$ |
| 477. | CN | F | $CH_3$ | $CF_3$ |
| 478. | $CH_3$ | F | $CH_3$ | $CF_3$ |
| 479. | $CF_3$ | F | $CH_3$ | $CF_3$ |
| 480. | $OCH_3$ | F | $CH_3$ | $CF_3$ |
| 481. | H | H | $CF_3$ | $CF_3$ |
| 482. | F | H | $CF_3$ | $CF_3$ |
| 483. | Cl | H | $CF_3$ | $CF_3$ |
| 484. | Br | H | $CF_3$ | $CF_3$ |
| 485. | CN | H | $CF_3$ | $CF_3$ |
| 486. | $CH_3$ | H | $CF_3$ | $CF_3$ |
| 487. | $CF_3$ | H | $CF_3$ | $CF_3$ |
| 488. | $OCH_3$ | H | $CF_3$ | $CF_3$ |
| 489. | H | F | $CF_3$ | $CF_3$ |
| 490. | F | F | $CF_3$ | $CF_3$ |
| 491. | Cl | F | $CF_3$ | $CF_3$ |
| 492. | Br | F | $CF_3$ | $CF_3$ |
| 493. | CN | F | $CF_3$ | $CF_3$ |
| 494. | $CH_3$ | F | $CF_3$ | $CF_3$ |
| 495. | $CF_3$ | F | $CF_3$ | $CF_3$ |
| 496. | $OCH_3$ | F | $CF_3$ | $CF_3$ |
| 497. | H | H | $OCH_3$ | $CF_3$ |
| 498. | F | H | $OCH_3$ | $CF_3$ |
| 499. | Cl | H | $OCH_3$ | $CF_3$ |
| 500. | Br | H | $OCH_3$ | $CF_3$ |
| 501. | CN | H | $OCH_3$ | $CF_3$ |
| 502. | $CH_3$ | H | $OCH_3$ | $CF_3$ |
| 503. | $CF_3$ | H | $OCH_3$ | $CF_3$ |
| 504. | $OCH_3$ | H | $OCH_3$ | $CF_3$ |
| 505. | H | F | $OCH_3$ | $CF_3$ |
| 506. | F | F | $OCH_3$ | $CF_3$ |
| 507. | Cl | F | $OCH_3$ | $CF_3$ |
| 508. | Br | F | $OCH_3$ | $CF_3$ |
| 509. | CN | F | $OCH_3$ | $CF_3$ |
| 510. | $CH_3$ | F | $OCH_3$ | $CF_3$ |
| 511. | $CF_3$ | F | $OCH_3$ | $CF_3$ |
| 512. | $OCH_3$ | F | $OCH_3$ | $CF_3$ |
| 513. | H | H | H | $OCH_3$ |
| 514. | F | H | H | $OCH_3$ |
| 515. | Cl | H | H | $OCH_3$ |
| 516. | Br | H | H | $OCH_3$ |
| 517. | CN | H | H | $OCH_3$ |
| 518. | $CH_3$ | H | H | $OCH_3$ |
| 519. | $CF_3$ | H | H | $OCH_3$ |
| 520. | $OCH_3$ | H | H | $OCH_3$ |
| 521. | H | F | H | $OCH_3$ |
| 522. | F | F | H | $OCH_3$ |
| 523. | Cl | F | H | $OCH_3$ |
| 524. | Br | F | H | $OCH_3$ |
| 525. | CN | F | H | $OCH_3$ |
| 526. | $CH_3$ | F | H | $OCH_3$ |
| 527. | $CF_3$ | F | H | $OCH_3$ |
| 528. | $OCH_3$ | F | H | $OCH_3$ |
| 529. | H | H | F | $OCH_3$ |
| 530. | F | H | F | $OCH_3$ |
| 531. | Cl | H | F | $OCH_3$ |
| 532. | Br | H | F | $OCH_3$ |
| 533. | CN | H | F | $OCH_3$ |
| 534. | $CH_3$ | H | F | $OCH_3$ |
| 535. | $CF_3$ | H | F | $OCH_3$ |
| 536. | $OCH_3$ | H | F | $OCH_3$ |
| 537. | H | F | F | $OCH_3$ |
| 538. | F | F | F | $OCH_3$ |
| 539. | Cl | F | F | $OCH_3$ |
| 540. | Br | F | F | $OCH_3$ |

TABLE 1-continued

| Cpd. | $R^3$ | $R^4$ | $R^5$ | $R^7$ |
|---|---|---|---|---|
| 541. | CN | F | F | $OCH_3$ |
| 542. | $CH_3$ | F | F | $OCH_3$ |
| 543. | $CF_3$ | F | F | $OCH_3$ |
| 544. | $OCH_3$ | F | F | $OCH_3$ |
| 545. | H | H | Cl | $OCH_3$ |
| 546. | F | H | Cl | $OCH_3$ |
| 547. | Cl | H | Cl | $OCH_3$ |
| 548. | Br | H | Cl | $OCH_3$ |
| 549. | CN | H | Cl | $OCH_3$ |
| 550. | $CH_3$ | H | Cl | $OCH_3$ |
| 551. | $CF_3$ | H | Cl | $OCH_3$ |
| 552. | $OCH_3$ | H | Cl | $OCH_3$ |
| 553. | H | F | Cl | $OCH_3$ |
| 554. | F | F | Cl | $OCH_3$ |
| 555. | Cl | F | Cl | $OCH_3$ |
| 556. | Br | F | Cl | $OCH_3$ |
| 557. | CN | F | Cl | $OCH_3$ |
| 558. | $CH_3$ | F | Cl | $OCH_3$ |
| 559. | $CF_3$ | F | Cl | $OCH_3$ |
| 560. | $OCH_3$ | F | Cl | $OCH_3$ |
| 561. | H | H | Br | $OCH_3$ |
| 562. | F | H | Br | $OCH_3$ |
| 563. | Cl | H | Br | $OCH_3$ |
| 564. | Br | H | Br | $OCH_3$ |
| 565. | CN | H | Br | $OCH_3$ |
| 566. | $CH_3$ | H | Br | $OCH_3$ |
| 567. | $CF_3$ | H | Br | $OCH_3$ |
| 568. | $OCH_3$ | H | Br | $OCH_3$ |
| 569. | H | F | Br | $OCH_3$ |
| 570. | F | F | Br | $OCH_3$ |
| 571. | Cl | F | Br | $OCH_3$ |
| 572. | Br | F | Br | $OCH_3$ |
| 573. | CN | F | Br | $OCH_3$ |
| 574. | $CH_3$ | F | Br | $OCH_3$ |
| 575. | $CF_3$ | F | Br | $OCH_3$ |
| 576. | $OCH_3$ | F | Br | $OCH_3$ |
| 577. | H | H | CN | $OCH_3$ |
| 578. | F | H | CN | $OCH_3$ |
| 579. | Cl | H | CN | $OCH_3$ |
| 580. | Br | H | CN | $OCH_3$ |
| 581. | CN | H | CN | $OCH_3$ |
| 582. | $CH_3$ | H | CN | $OCH_3$ |
| 583. | $CF_3$ | H | CN | $OCH_3$ |
| 584. | $OCH_3$ | H | CN | $OCH_3$ |
| 585. | H | F | CN | $OCH_3$ |
| 586. | F | F | CN | $OCH_3$ |
| 587. | Cl | F | CN | $OCH_3$ |
| 588. | Br | F | CN | $OCH_3$ |
| 589. | CN | F | CN | $OCH_3$ |
| 590. | $CH_3$ | F | CN | $OCH_3$ |
| 591. | $CF_3$ | F | CN | $OCH_3$ |
| 592. | $OCH_3$ | F | CN | $OCH_3$ |
| 593. | H | H | $CH_3$ | $OCH_3$ |
| 594. | F | H | $CH_3$ | $OCH_3$ |
| 595. | Cl | H | $CH_3$ | $OCH_3$ |
| 596. | Br | H | $CH_3$ | $OCH_3$ |
| 597. | CN | H | $CH_3$ | $OCH_3$ |
| 598. | $CH_3$ | H | $CH_3$ | $OCH_3$ |
| 599. | $CF_3$ | H | $CH_3$ | $OCH_3$ |
| 600. | $OCH_3$ | H | $CH_3$ | $OCH_3$ |
| 601. | H | F | $CH_3$ | $OCH_3$ |
| 602. | F | F | $CH_3$ | $OCH_3$ |
| 603. | Cl | F | $CH_3$ | $OCH_3$ |
| 604. | Br | F | $CH_3$ | $OCH_3$ |
| 605. | CN | F | $CH_3$ | $OCH_3$ |
| 606. | $CH_3$ | F | $CH_3$ | $OCH_3$ |
| 607. | $CF_3$ | F | $CH_3$ | $OCH_3$ |
| 608. | $OCH_3$ | F | $CH_3$ | $OCH_3$ |
| 609. | H | H | $CF_3$ | OCH; |
| 610. | F | H | $CF_3$ | $OCH_3$ |
| 611. | Cl | H | $CF_3$ | $OCH_3$ |
| 612. | Br | H | $CF_3$ | $OCH_3$ |
| 613. | CN | H | $CF_3$ | $OCH_3$ |
| 614. | $CH_3$ | H | $CF_3$ | $OCH_3$ |
| 615. | $CF_3$ | H | $CF_3$ | $OCH_3$ |
| 616. | $OCH_3$ | H | $CF_3$ | $OCH_3$ |
| 617. | H | F | $CF_3$ | $OCH_3$ |
| 618. | F | F | $CF_3$ | $OCH_3$ |
| 619. | Cl | F | $CF_3$ | $OCH_3$ |
| 620. | Br | F | $CF_3$ | $OCH_3$ |
| 621. | CN | F | $CF_3$ | $OCH_3$ |
| 622. | $CH_3$ | F | $CF_3$ | $OCH_3$ |
| 623. | $CF_3$ | F | $CF_3$ | $OCH_3$ |
| 624. | $OCH_3$ | F | $CF_3$ | $OCH_3$ |
| 625. | H | H | $OCH_3$ | $OCH_3$ |
| 626. | F | H | $OCH_3$ | $OCH_3$ |
| 627. | Cl | H | $OCH_3$ | $OCH_3$ |
| 628. | Br | H | $OCH_3$ | OCH3 |
| 629. | CN | H | $OCH_3$ | $OCH_3$ |
| 630. | $CH_3$ | H | $OCH_3$ | $OCH_3$ |
| 631. | $CF_3$ | H | $OCH_3$ | $OCH_3$ |
| 632. | $OCH_3$ | H | $OCH_3$ | $OCH_3$ |
| 633. | H | F | $OCH_3$ | $OCH_3$ |
| 634. | F | F | $OCH_3$ | $OCH_3$ |
| 635. | Cl | F | $OCH_3$ | $OCH_3$ |
| 636. | Br | F | $OCH_3$ | $OCH_3$ |
| 637. | CN | F | $OCH_3$ | $OCH_3$ |
| 638. | $CH_3$ | F | $OCH_3$ | $OCH_3$ |
| 639. | $CF_3$ | F | $OCH_3$ | $OCH_3$ |
| 640. | $OCH_3$ | F | $OCH_3$ | $OCH_3$ |
| 641. | H | H | H | 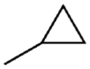 |
| 642. | F | H | H | 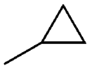 |
| 643. | Cl | H | H | 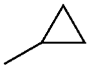 |
| 644. | Br | H | H | 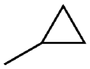 |
| 645. | CN | H | H | 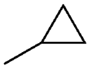 |
| 646. | $CH_3$ | H | H | 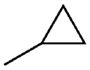 |
| 647. | $CF_3$ | H | H | 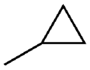 |
| 648. | $OCH_3$ | H | H | 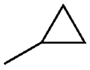 |
| 649. | H | F | H | 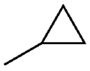 |
| 650. | F | F | H | 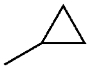 |
| 651. | Cl | F | H | 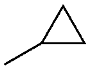 |
| 652. | Br | F | H | 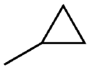 |
| 653. | CN | F | H | 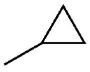 |

TABLE 1-continued
| Cpd. | $R^3$ | $R^4$ | $R^5$ | $R^7$ |
|---|---|---|---|---|
| 654. | $CH_3$ | F | H | 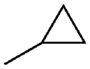 |
| 655. | $CF_3$ | F | H | 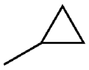 |
| 656. | $OCH_3$ | F | H | 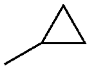 |
| 657. | H | H | F | 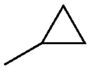 |
| 658. | F | H | F | 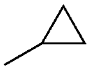 |
| 659. | Cl | H | F | 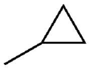 |
| 660. | Br | H | F | 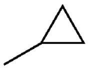 |
| 661. | CN | H | F | 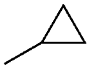 |
| 662. | $CH_3$ | H | F | 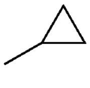 |
| 663. | $CF_3$ | H | F | 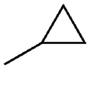 |
| 664. | $OCH_3$ | H | F | 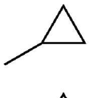 |
| 665. | H | F | F | 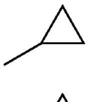 |
| 666. | F | F | F | 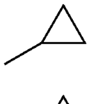 |
| 667. | Cl | F | F | 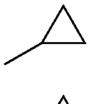 |
| 668. | Br | F | F | 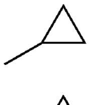 |
| 669. | CN | F | F | 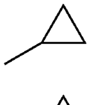 |
| 670. | $CH_3$ | F | F | 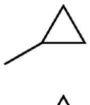 |
| 671. | $CF_3$ | F | F | 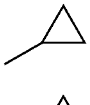 |
| 672. | $OCH_3$ | F | F | 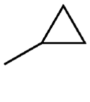 |
TABLE 1-continued
| Cpd. | $R^3$ | $R^4$ | $R^5$ | $R^7$ |
|---|---|---|---|---|
| 673. | H | H | Cl | 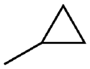 |
| 674. | F | H | Cl | 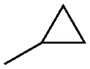 |
| 675. | Cl | H | Cl | 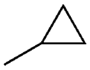 |
| 676. | Br | H | Cl | 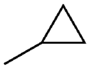 |
| 677. | CN | H | Cl | 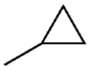 |
| 678. | $CH_3$ | H | Cl | 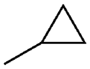 |
| 679. | $CF_3$ | H | Cl | 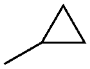 |
| 680. | $OCH_3$ | H | Cl | 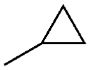 |
| 681. | H | F | Cl | 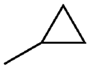 |
| 682. | F | F | Cl | 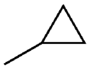 |
| 683. | Cl | F | Cl | 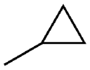 |
| 684. | Br | F | Cl | 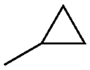 |
| 685. | CN | F | Cl | 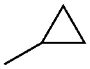 |
| 686. | $CH_3$ | F | Cl | 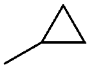 |
| 687. | $CF_3$ | F | Cl | 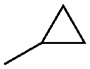 |
| 688. | $OCH_3$ | F | Cl | 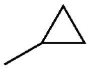 |
| 689. | H | H | Br | 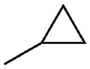 |
| 690. | F | H | Br | 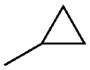 |

TABLE 1-continued
| Cpd. | $R^3$ | $R^4$ | $R^5$ | $R^7$ |
|---|---|---|---|---|
| 691. | Cl | H | Br | 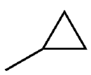 |
| 692. | Br | H | Br | 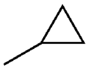 |
| 693. | CN | H | Br | 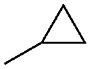 |
| 694. | $CH_3$ | H | Br | 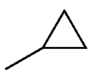 |
| 695. | $CF_3$ | H | Br | 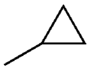 |
| 696. | $OCH_3$ | H | Br | 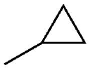 |
| 697. | H | F | Br | 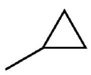 |
| 698. | F | F | Br | 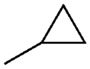 |
| 699. | Cl | F | Br | 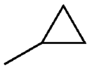 |
| 700. | Br | F | Br | 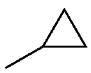 |
| 701. | CN | F | Br | 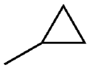 |
| 702. | $CH_3$ | F | Br | 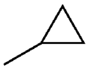 |
| 703. | $CF_3$ | F | Br | 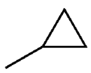 |
| 704. | $OCH_3$ | F | Br | 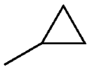 |
| 705. | H | H | CN | 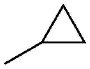 |
| 706. | F | H | CN | 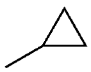 |
| 707. | Cl | H | CN | 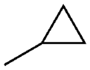 |
| 708. | Br | H | CN | 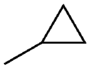 |
| 709. | CN | H | CN | 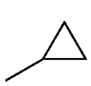 |
| 710. | $CH_3$ | H | CN | 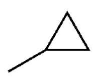 |
| 711. | $CF_3$ | H | CN | 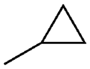 |
| 712. | $OCH_3$ | H | CN | 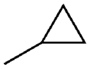 |
| 713. | H | F | CN | 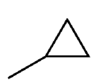 |
| 714. | F | F | CN | 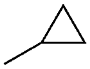 |
| 715. | Cl | F | CN | 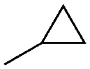 |
| 716. | Br | F | CN | 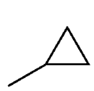 |
| 717. | CN | F | CN | 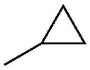 |
| 718. | $CH_3$ | F | CN | 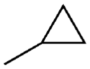 |
| 719. | $CF_3$ | F | CN | 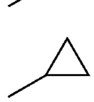 |
| 720. | $OCH_3$ | F | CN | 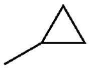 |
| 721. | H | H | $CH_3$ | 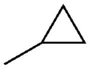 |
| 722. | F | H | $CH_3$ | 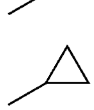 |
| 723. | Cl | H | $CH_3$ | 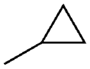 |
| 724. | Br | H | $CH_3$ | 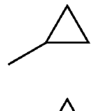 |
| 725. | CN | H | $CH_3$ | 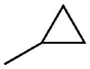 |
| 726. | $CH_3$ | H | $CH_3$ | 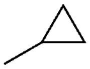 |
| 727. | $CF_3$ | H | $CH_3$ | 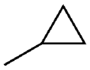 |

TABLE 1-continued

| Cpd. | $R^3$ | $R^4$ | $R^5$ | $R^7$ |
|---|---|---|---|---|
| 728. | $OCH_3$ | H | $CH_3$ | 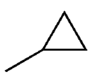 |
| 729. | H | F | $CH_3$ | 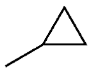 |
| 730. | F | F | $CH_3$ | 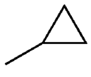 |
| 731. | Cl | F | $CH_3$ | 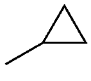 |
| 732. | Br | F | $CH_3$ | 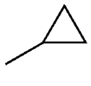 |
| 733. | CN | F | $CH_3$ | 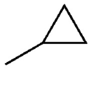 |
| 734. | $CH_3$ | F | $CH_3$ | 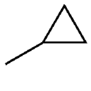 |
| 735. | $CF_3$ | F | $CH_3$ | 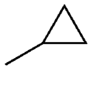 |
| 736. | $OCH_3$ | F | $CH_3$ | 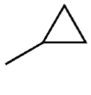 |
| 737. | H | H | $CF_3$ | 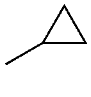 |
| 738. | F | H | $CF_3$ | 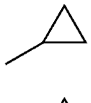 |
| 739. | Cl | H | $CF_3$ | 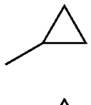 |
| 740. | Br | H | $CF_3$ | 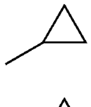 |
| 741. | CN | H | $CF_3$ | 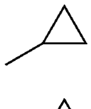 |
| 742. | $CH_3$ | H | $CF_3$ | 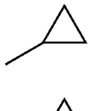 |
| 743. | $CF_3$ | H | $CF_3$ | 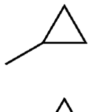 |
| 744. | $OCH_3$ | H | $CF_3$ | 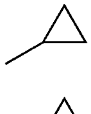 |
| 745. | H | F | $CF_3$ | 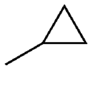 |

TABLE 1-continued

| Cpd. | $R^3$ | $R^4$ | $R^5$ | $R^7$ |
|---|---|---|---|---|
| 746. | F | F | $CF_3$ | 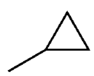 |
| 747. | Cl | F | $CF_3$ | 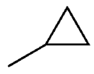 |
| 748. | Br | F | $CF_3$ | 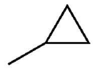 |
| 749. | CN | F | $CF_3$ | 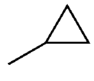 |
| 750. | $CH_3$ | F | $CF_3$ | 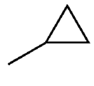 |
| 751. | $CF_3$ | F | $CF_3$ | 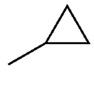 |
| 752. | $OCH_3$ | F | $CF_3$ | 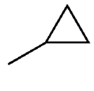 |
| 753. | H | H | $OCH_3$ | 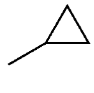 |
| 754. | F | H | $OCH_3$ | 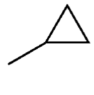 |
| 755. | Cl | H | $OCH_3$ | 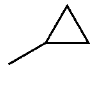 |
| 756. | Br | H | $OCH_3$ | 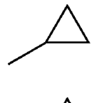 |
| 757. | CN | H | $OCH_3$ | 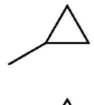 |
| 758. | $CH_3$ | H | $OCH_3$ | 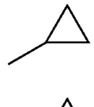 |
| 759. | $CF_3$ | H | $OCH_3$ | 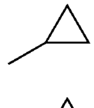 |
| 760. | $OCH_3$ | H | $OCH_3$ | 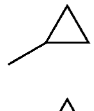 |
| 761. | H | F | $OCH_3$ | 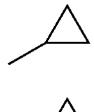 |
| 762. | F | F | $OCH_3$ | 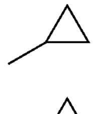 |
| 763. | Cl | F | $OCH_3$ | 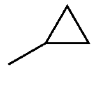 |

TABLE 1-continued

| Cpd. | $R^3$ | $R^4$ | $R^5$ | $R^7$ |
|---|---|---|---|---|
| 764. | Br | F | $OCH_3$ | 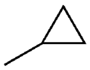 |
| 765. | CN | F | $OCH_3$ | 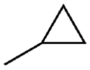 |
| 766. | $CH_3$ | F | $OCH_3$ | 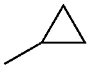 |
| 767. | $CF_3$ | F | $OCH_3$ | 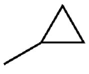 |
| 768. | $OCH_3$ | F | $OCH_3$ | 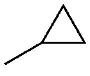 |

In Table 1,  means cyclopropyl.

Compounds of formula I.1., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.1.1-I.1.768, are particularly preferred:

(I.1.)

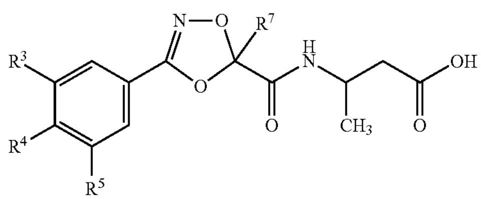

Compounds of formula I.2., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.2.1-I.2.768, are particularly preferred:

(I.2.)

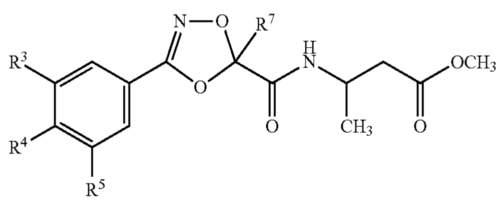

Compounds of formula I.3., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.3.1-I.3.768, are particularly preferred:

(I.3.)

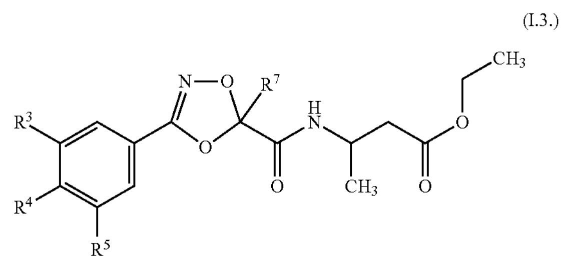

Compounds of formula I.4., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.4.1-I.4.768, are particularly preferred:

(I.4.)

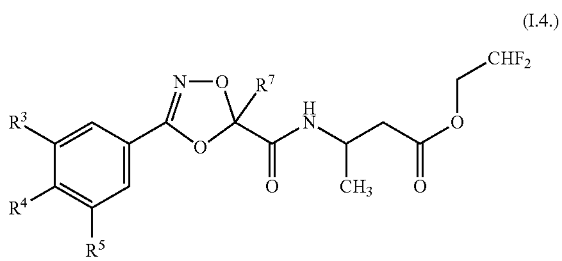

Compounds of formula I.5., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.5.1-I.5.768, are particularly preferred:

(I.5.)

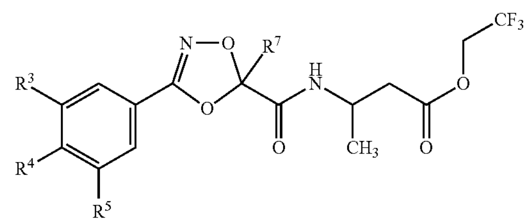

Compounds of formula I.6., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.6.1-I.6.768, are particularly preferred:

(I.6.)

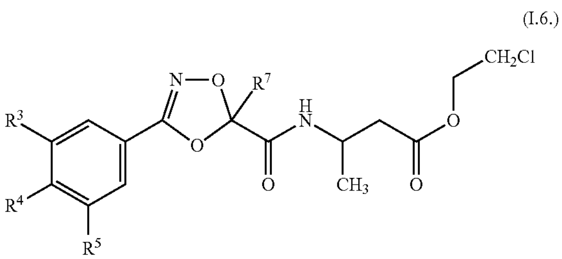

Compounds of formula I.7., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.7.1-I.7.768, are particularly preferred:

(I.7.)

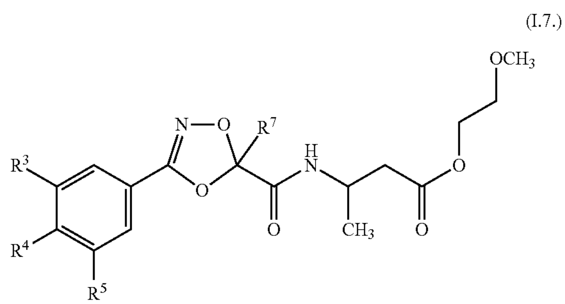

Compounds of formula I.8., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.8.1-I.8.768, are particularly preferred:

(I.8.)

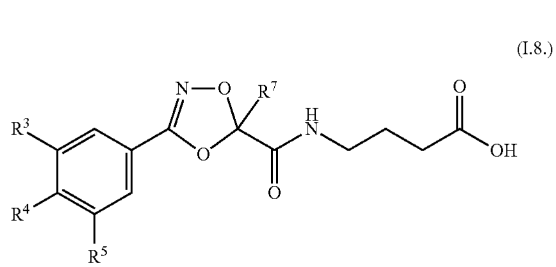

Compounds of formula I.9., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.9.1-I.9.768, are particularly preferred:

(I.9.)

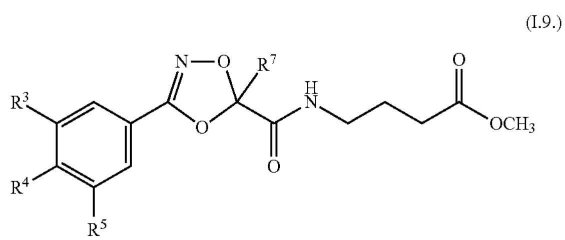

Compounds of formula I.10., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.10.1-I.10.768, are particularly preferred:

(I.10.)

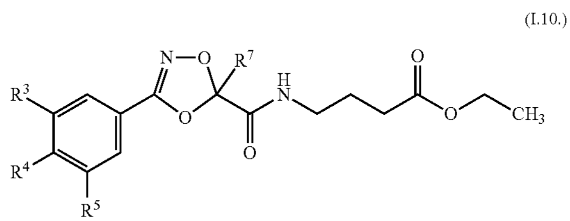

Compounds of formula I.11., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.11.1-I.11.768, are particularly preferred:

(I.11.)

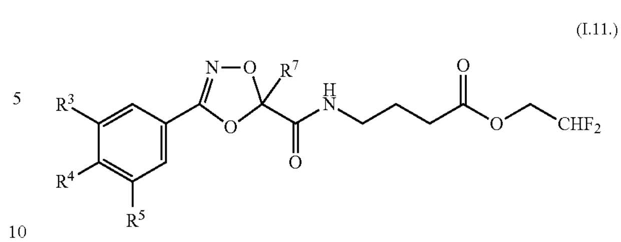

Compounds of formula I.12., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.12.1-I.12.768, are particularly preferred:

(I.12.)

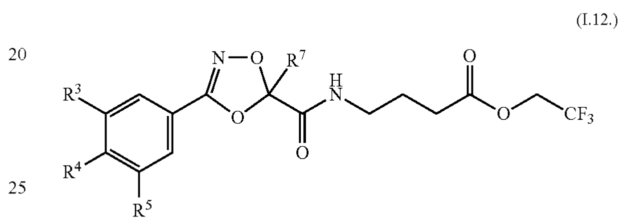

Compounds of formula I.13., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.13.1-I.13.768, are particularly preferred:

(I.13.)

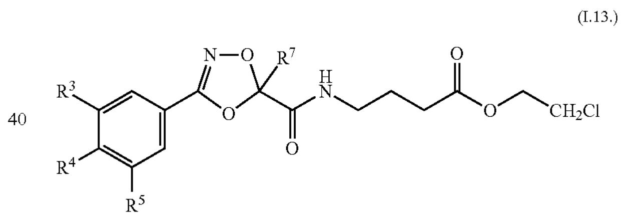

Compounds of formula I.14., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.14.1-I.14.768, are particularly preferred:

(I.14.)

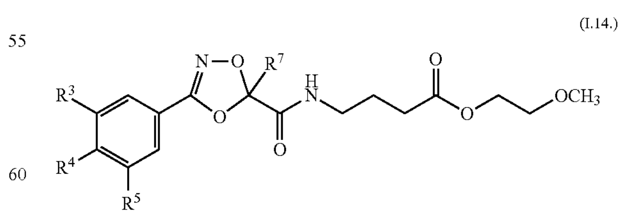

Compounds of formula I.15., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.15.1-I.15.768, are particularly preferred:

(I.15.)

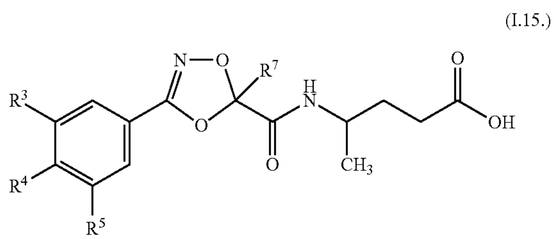

Compounds of formula I.16., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.16.1-I.16.768, are particularly preferred:

(I.16.)

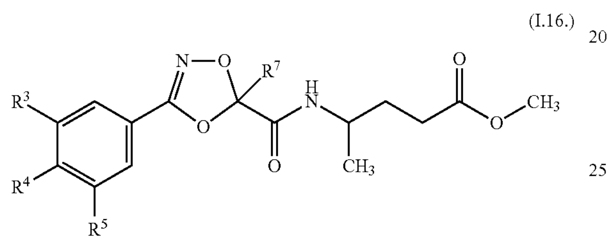

Compounds of formula I.17., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.17.1-I.17.768, are particularly preferred:

(I.17.)

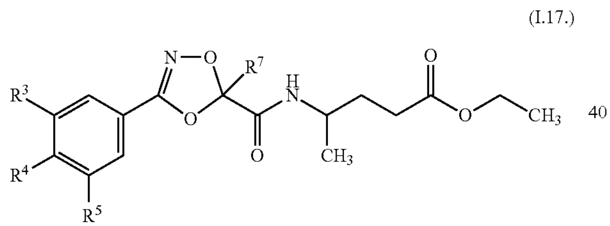

Compounds of formula I.18., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.18.1-I.18.768, are particularly preferred:

(I.18.)

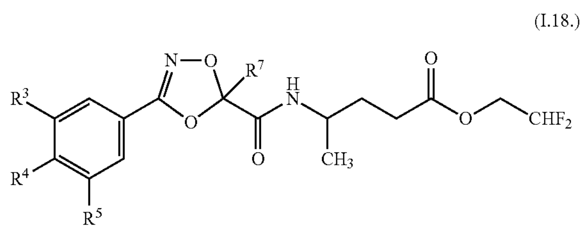

Compounds of formula I.19., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.19.1-I.19.768, are particularly preferred:

(I.19.)

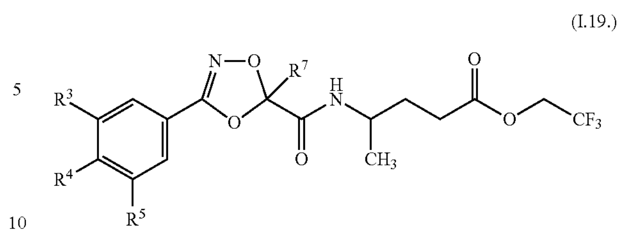

Compounds of formula I.20., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.20.1-I.20.768, are particularly preferred:

(I.20.)

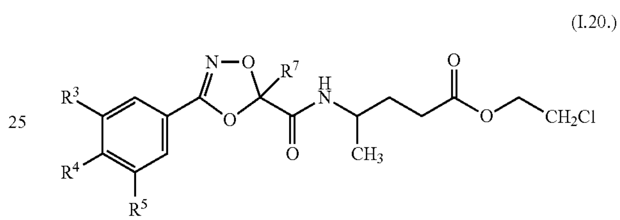

Compounds of formula I.21., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.21.1-I.21.768, are particularly preferred:

(I.21.)

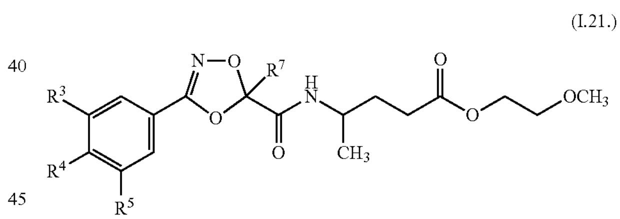

Compounds of formula I.22., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.22.1-I.22.768, are particularly preferred:

(I.22.)

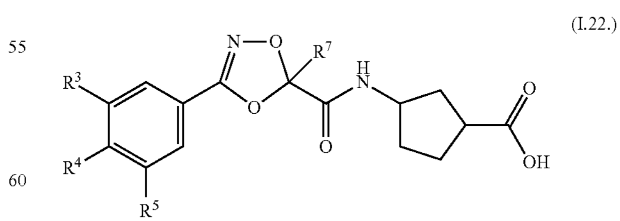

Compounds of formula I.23., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.23.1-I.23.768, are particularly preferred:

(I.23.)

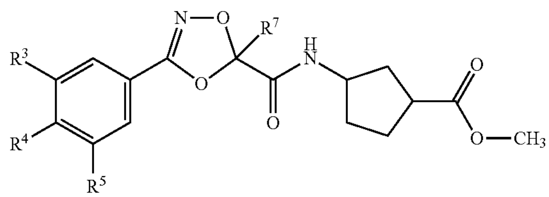

Compounds of formula I.24., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.24.1-I.24.768, are particularly preferred:

(I.24.)

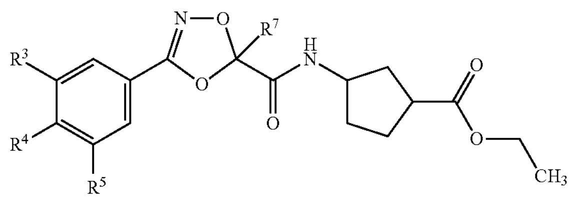

Compounds of formula I.25., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.25.1-I.25.768, are particularly preferred:

(I.25.)

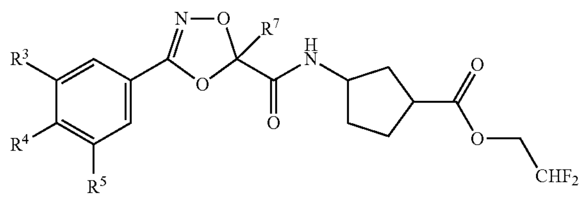

Compounds of formula I.26., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.26.1-I.26.768, are particularly preferred:

(I.26.)

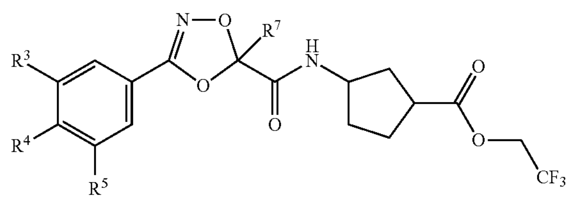

Compounds of formula I.27., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.27.1-I.27.768, are particularly preferred:

(I.27.)

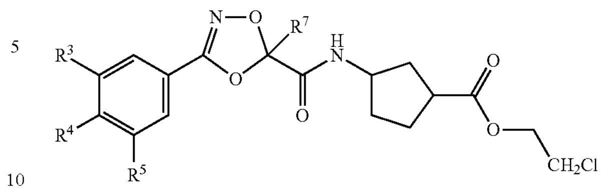

Compounds of formula I.28., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.28.1-I.28.768, are particularly preferred:

(I.28.)

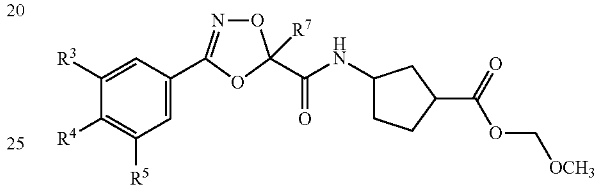

Compounds of formula I.29., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.29.1-I.29.768, are particularly preferred:

(I.29.)

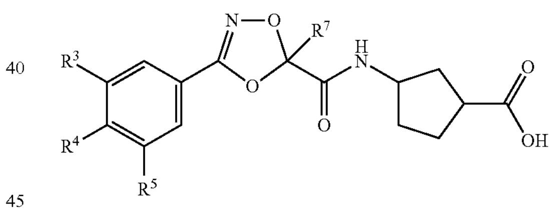

Compounds of formula I.30., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.30.1-I.30.768, are particularly preferred:

(I.30)

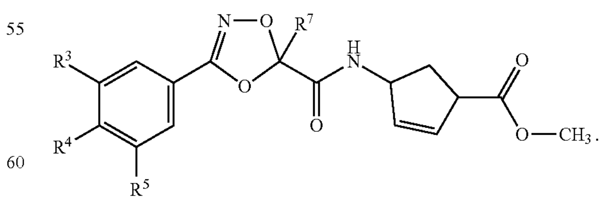

Compounds of formula I.31., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.31.1-I.31.768, are particularly preferred:

(I.31)

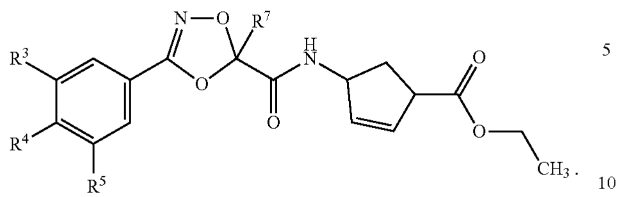

Compounds of formula I.32., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.32.1-I.32.768, are particularly preferred:

(I.32)

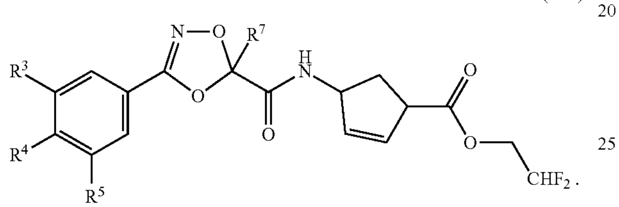

Compounds of formula I.33., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.33.1-I.33.768, are particularly preferred:

(I.33)

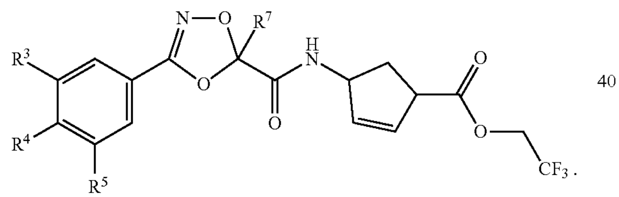

Compounds of formula I.34., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.34.1-I.34.768, are particularly preferred:

(I.34)

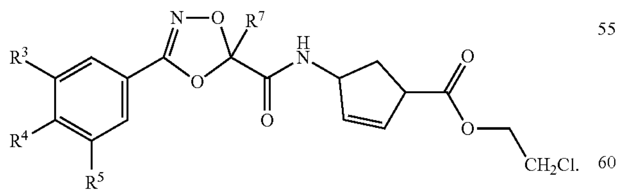

Compounds of formula I.35., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.35.1-I.35.768, are particularly preferred:

(I.35)

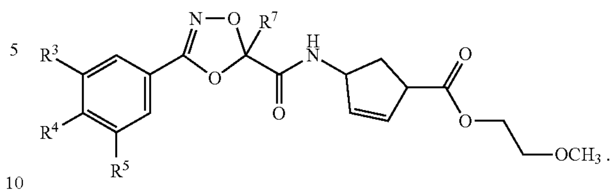

Compounds of formula I.36., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.36.1-I.36.768, are particularly preferred:

(I.36)

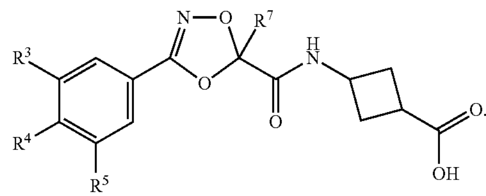

Compounds of formula I.37., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.37.1-I.37.768, are particularly preferred:

(I.37)

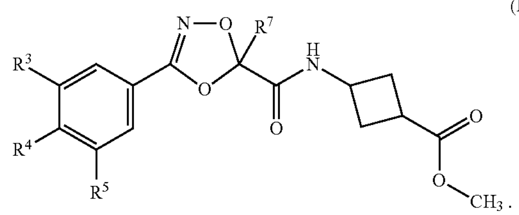

Compounds of formula I.38., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.38.1-I.38.768, are particularly preferred:

(I.38)

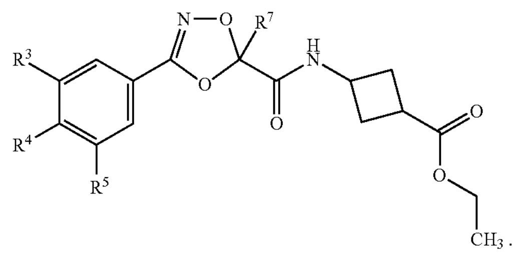

Compounds of formula I.39., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.39.1-I.39.768, are particularly preferred:

(I.39)

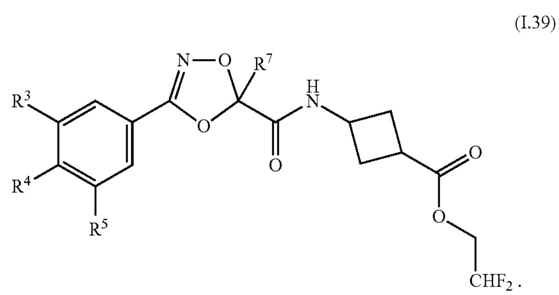

Compounds of formula I.40., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.40.1-I.40.768, are particularly preferred:

(I.40)

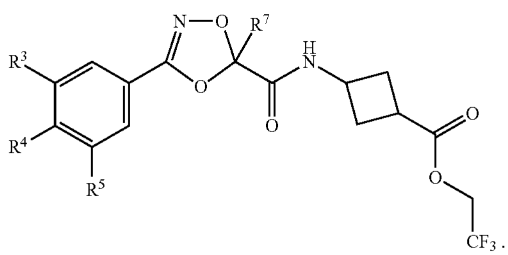

Compounds of formula I.41., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.41.1-I.41.768, are particularly preferred:

(I.41)

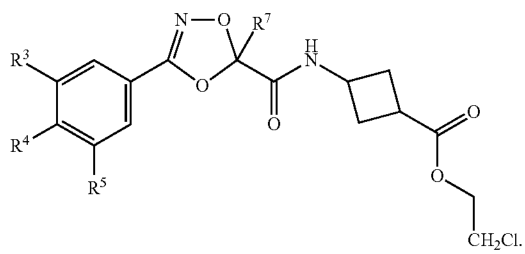

Compounds of formula I.42., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.42.1-I.42.768, are particularly preferred:

(I.42)

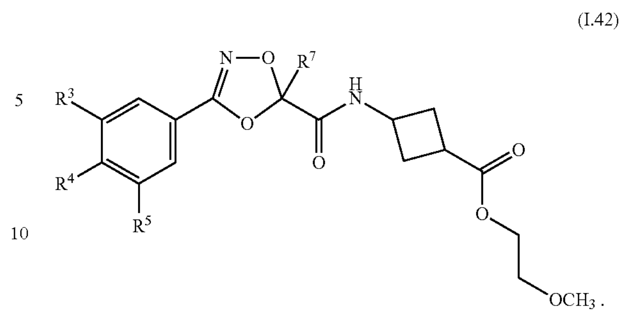

Compounds of formula I.43., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.43.1-I.43.768, are particularly preferred:

(I.43)

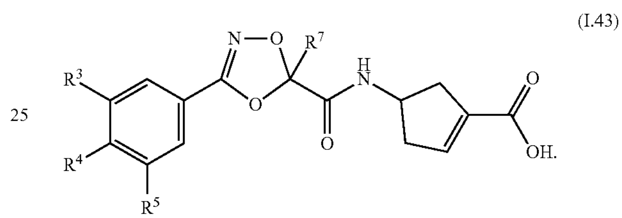

Compounds of formula I.44., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.44.1-I.44.768, are particularly preferred:

(I.44)

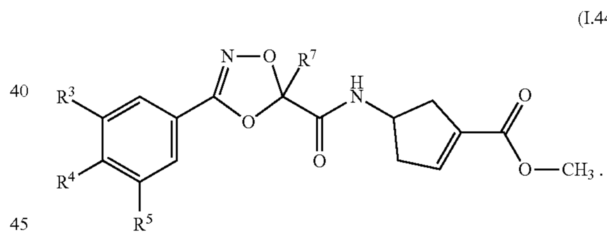

Compounds of formula I.45., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.45.1-I.45.768, are particularly preferred:

(I.45.)

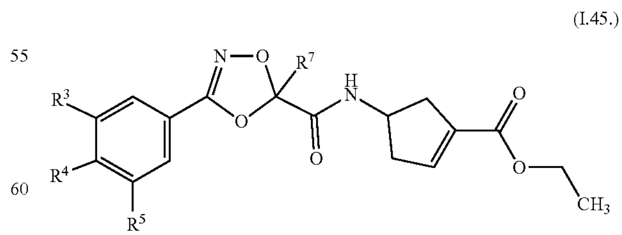

Compounds of formula I.46., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.46.1-I.46.768, are particularly preferred:

(I.46.)

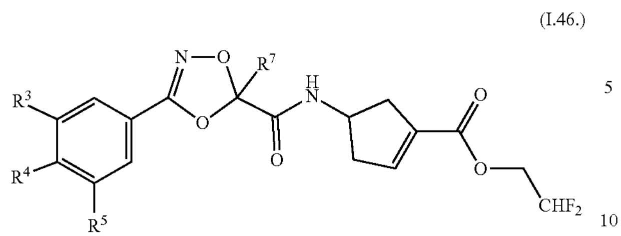

Compounds of formula I.47., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.47.1-I.47.768, are particularly preferred:

(I.47)

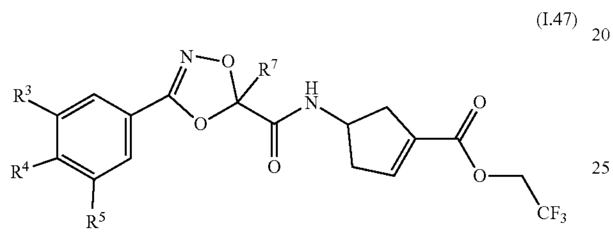

Compounds of formula I.48., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.48.1-I.48.768, are particularly preferred:

(I.48.)

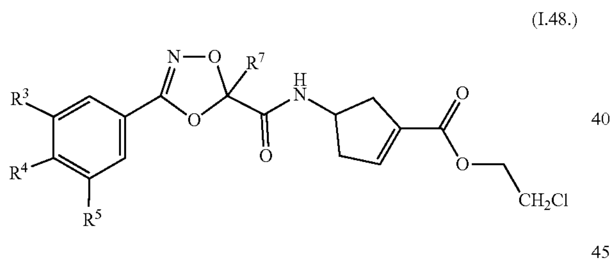

Compounds of formula I.49., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.49.1-I.49.768, are particularly preferred:

(I.49.)

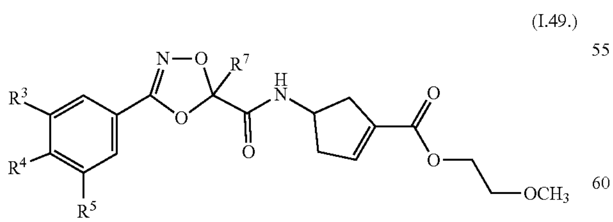

Compounds of formula I.50., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.50.1-I.50.768, are particularly preferred:

(I.50.)

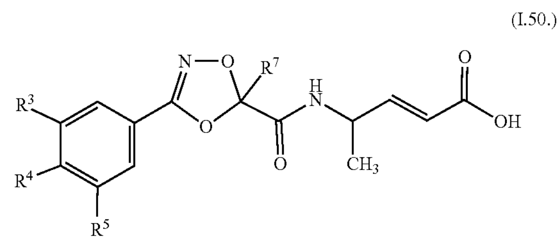

Compounds of formula I.51., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.51.1-I.51.768, are particularly preferred:

(I.51.)

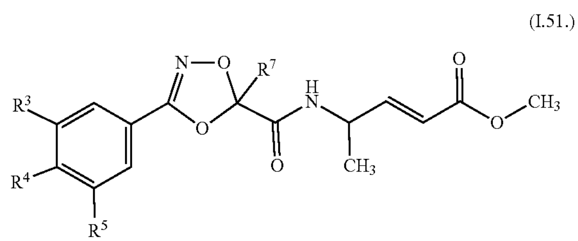

Compounds of formula I.52., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.52.1-I.52.768, are particularly preferred:

(I.52.)

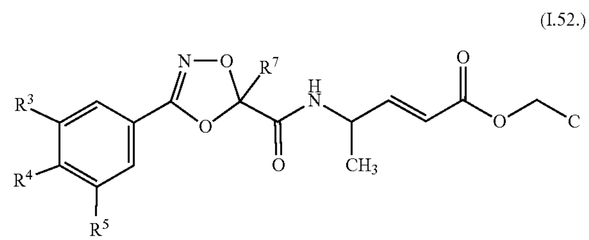

Compounds of formula I.53., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.53.1-I.53.768, are particularly preferred:

(I.53.)

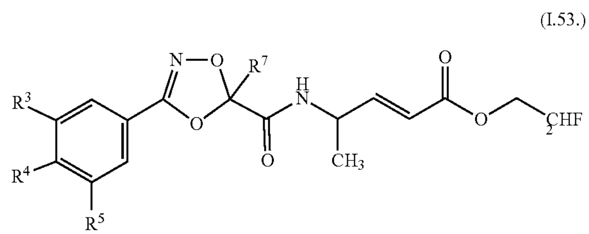

Compounds of formula I.54., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.54.1-I.54.768, are particularly preferred:

(I.55.)

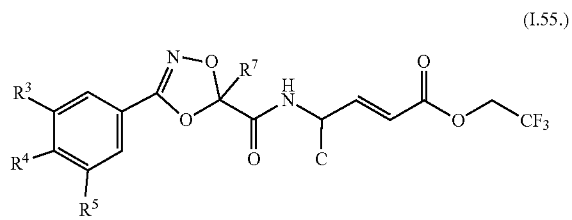

Compounds of formula I.55., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.55.1-I.55.768, are particularly preferred:

(I.55.)

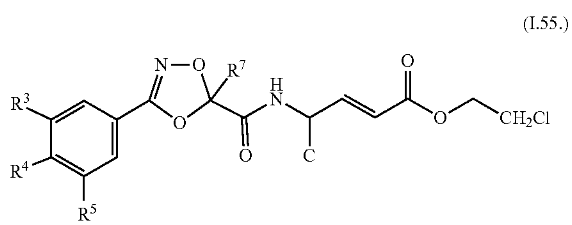

Compounds of formula I.56., wherein $R^1$, $R^2$, and $R^6$ are hydrogen, and $R^3$, $R^4$, $R^5$ and $R^7$ have the meanings as defined lines in 1 to 768 of Table 1 above, i.e. individual compounds I.56.1-I.56.768 are particularly preferred:

(I.56)

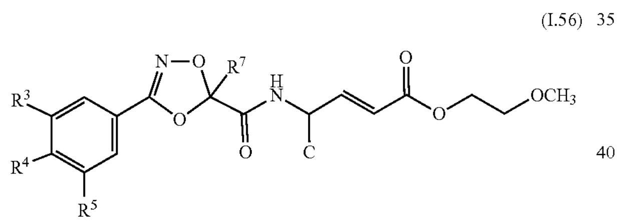

The compounds of formula (I) according to the invention can be prepared by standard processes of organic chemistry, for example by the following processes:

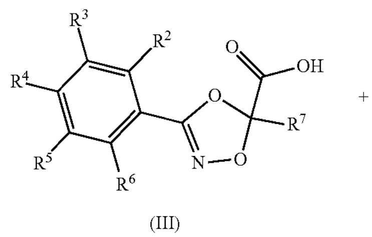

(III)

+

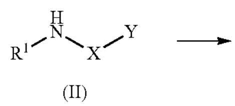

(II)

-continued

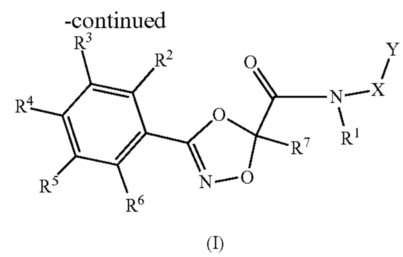

(I)

The compounds of formula (I) can be prepared according to methods or in analogy to methods that are described in the prior art. The synthesis takes advantage of starting materials that are commercially available or may be prepared according to conventional procedures starting from readily available compounds.

Compounds of the formula (I) can be prepared from the carboxylic acids (III) and commercially available amines (II) using an organic base and a coupling reagent. Thus, compounds of formula (I) can be synthesized from the corresponding carboxylic acids (1 eq.) using a coupling reagent (1-2 eq.), for example $T_3P$ (propanephosphonic acid anhydride) or HATU (O-(7-azabenzotriazole-1-yl)-N,N,N',N'-tetramethyluronium-hexafluorphosphate), an organic base (1-3 eq.) and the amines (II) (1-3 eq.). The reaction is typically carried out in an organic solvent. Preferably an aprotic organic solvent is used. Most preferably tetrahydrofuran (THF), N,N-dimethylformamide (DMF) or acetonitrile (ACN) are used. The reaction is carried out at temperatures between 0° C. and reflux. Preferably the reaction is carried out at room temperature. Preferably the organic base is triethylamine or N,N-diisopropylethylamine.

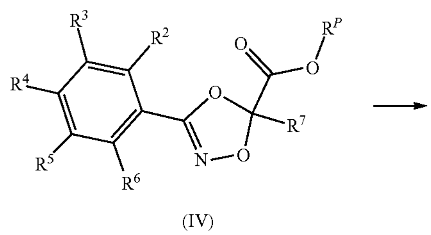

(IV)

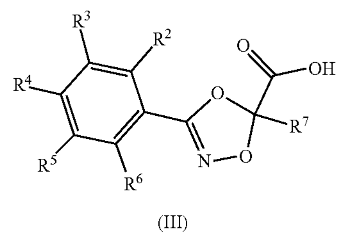

(III)

The carboxylic acids (III) are commercially available or can be prepared from the corresponding esters (IV) (wherein RP is alkyl or benzyl). If RP is alkyl, esters (IV) may be cleaved using aqueous alkali metal hydroxides. Preferably lithium hydroxide, sodium hydroxide or potassium hydroxide (1-2 eq.) are employed. The reaction is typically carried out in mixtures of water and an organic solvent. Preferably the organic solvent is THF, methanol or acetonitrile. The reaction is carried out at temperatures between 0° C. and 100° C. Preferably the reaction is carried at room temperature. If RP is benzyl in (IV), then the ester may be cleaved using palladium on charcoal (0.001-1 eq.) as catalyst and hydrogen gas at temperatures between 0° C. and reflux.

Preferably the reaction is carried out at room temperature. Typically, an organic solvent is employed. Preferably THF, methanol or ethanol are employed.

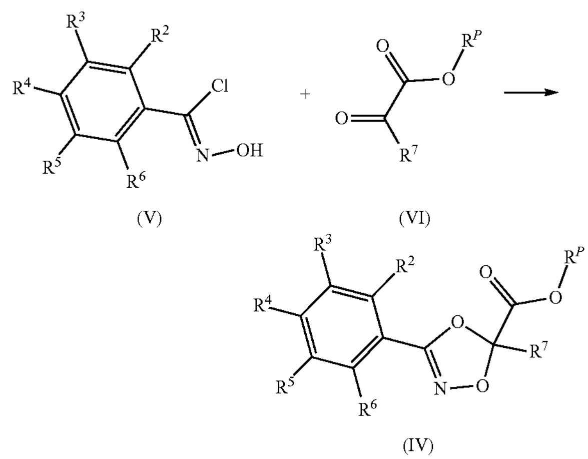

The esters (IV) can be prepared by combining the N-hydroxybenzene-1-carbonimidoyl chloride (V) and 2-oxo-carboxylic acid esters (VI) in the presence of a base in analogy to the procedures described in Chem. Ber. 105, 2805-2814 (1972). Preferably nitrogen-containing bases are used, such as $(C_1-C_6)$-alkylamines, preferably tri-$(C_1-C_6)$-alkylamines, for example triethylamine, trimethylamine, N-ethyldiisopropylamine, using 1-2 equivalents with respect to the N-hydroxybenzene-1-carbonimidoyl chlorides (V). The 2-oxo-carboxylic acid esters (VI) are used at 1-10 eq, preferably at 2-5 eq.

The reaction is typically carried out in an organic solvent. Preferably the organic solvent is an aromatic hydrocarbon such as benzene, chlorobenzene, toluene, cresols or o-, m- and p-xylene. The reaction is carried out at temperatures between 0° C. and 100° C. Preferably the reaction is carried at room temperature.

N-hydroxybenzene-1-carbonimidoyl chlorides (V) are commercially available or can be prepared by known methods (e.g. WO12130798, WO1404882, WO14048882, WO18228985, WO18228986, WO19034602 or WO19145245 and references described therein).

$R^7$ on compound (I), (III) or (IV) can be synthetically further modified by known methods.

To widen the spectrum of action, the compounds of formula (I) may be mixed with many representatives of other herbicidal or growth-regulating active ingredient groups and then applied concomitantly. Suitable components for combinations are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

It may furthermore be beneficial to apply the compounds of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

In one embodiment of the present invention the combinations according to the present invention comprise at least one compound of formula (I) (compound A or component A) and at least one further active compound selected from herbicides B (compound B), preferably herbicides B of class b1) to b15), and safeners C (compound C).

In another embodiment of the present invention the combinations according to the present invention comprise at least one compound of formula (I) and at least one further active compound B (herbicide B).

Examples of herbicides B which can be used in combination with the compounds A of formula (I) according to the present invention are:

b1) from the group of the lipid biosynthesis inhibitors:

ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:

amicarbazone, inhibitors of the photosystem II, e.g. 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8), 1-(5-tert-butylisoxazol-3-yl)-4-ethoxy-5-hydroxy-3-methyl-imidazolidin-2-one (CAS 1844836-64-1), triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, chlorphthalim, cinidon-ethyl, cyclopyranil, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-di-chloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4), 2-[2-chloro-5-[3-chloro-5-(trifluoromethyl)-2-pyridinyl]-4-fluorophenoxy]-2-methoxy-acetic acid methyl ester (CAS 1970221-16-9), 2-[2-[[3-chloro-6-[3,6-dihydro-3-methyl-2,6-dioxo-4-(trifluoro-methyl)-1(2H)-pyrimidinyl]-5-fluoro-2-pyridinyl]oxy]phenoxy]-acetic acid methyl ester (CAS 2158274-96-3), 2-[2-[[3-chloro-6-[3,6-dihydro-3-methyl-2,6-dioxo-4-(trifluoromethyl)-1(2H)-pyrimidinyl]-5-fluoro-2-pyridinyl]oxy]phenoxy] acetic acid ethyl ester (CAS 158274-50-9), methyl 2-[[3-[2-chloro-5-[4-(difluoromethyl)-3-methyl-5-oxo-1,2,4-triazol- 1-yl]-4-fluoro-phenoxy]-2-pyridyl]oxy]acetate (CAS 2271389-22-9), ethyl 2-[[3-[2-chloro-5-[4-(difluoromethyl)-3-methyl-5-oxo-1,2,4-triazol-1-yl]-4-fluoro-phenoxy]-2-pyridyl]oxy]acetate (CAS 2230679-62-4), 2-[[3-[[3-chloro-6-[3,6-dihydro-3-methyl-2,6-dioxo-4-(trifluoromethyl)-1(2H)-pyrimidinyl]-5-fluoro-2-pyridinyl]oxy]-2-pyridinyl]oxy]-acetic acid methyl ester (CAS 2158275-73-9), 2-[[3-[[3-chloro-6-[3,6-dihydro-3-methyl-2,6-dioxo-4-(trifluoromethyl)-1(2H)-pyrimidinyl]-5-fluoro-2-pyridinyl]oxy]-2-pyridinyl]oxy] acetic acid ethyl ester (CAS 2158274-56-5), 2-[2-[[3-chloro-6-[3,6-dihydro-3-methyl-2,6-dioxo-4-(trifluoromethyl)-1(2H)-pyrimidinyl]-5-fluoro-2-pyridinyl]oxy]phenoxy]-N-(methylsulfonyl)-acetamide (CAS 2158274-53-2), 2-[[3-[[3-chloro-6-[3,6-dihydro-3-methyl-2,6-dioxo-4-(trifluoromethyl)-1(2H)-pyrimidinyl]-5-fluoro-2-pyridinyl]oxy]-2-pyridinyl]oxy]-N-(methylsulfonyl)acetamide (CAS 2158276-22-1);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl) pyrimidine (CAS 180608-33-7), HPPD inhibitors: benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate, topramezone, bleacher, unknown target: aclonifen, amitrole flumeturon 2-chloro-3-methylsulfanyl-N-(1-methyltetrazol-5-yl)-4-(trifluoromethyl)benzamide (CAS 1361139-71-0), bixlozone and 2-(2,5-dichlorophenyl)methyl-4,4-dimethyl-3-isoxazolidinone (CAS 81778-66-7);

b6) from the group of the EPSP synthase inhibitors:

glyphosate, glyphosate-isopropylammonium, glyposate-potassium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium:

b8) from the group of the DHP synthase inhibitors:

asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:

chloroacetamides such as acetochlor, alachlor, amidochlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

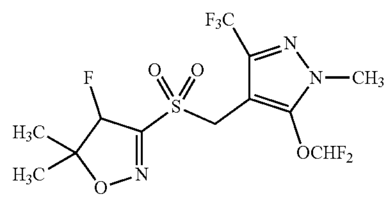
II.1

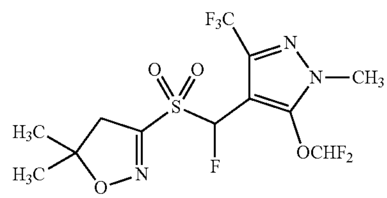
II.2

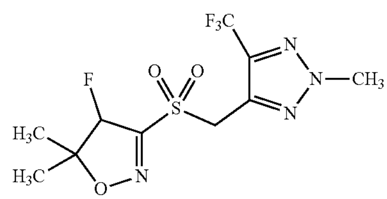
II.3

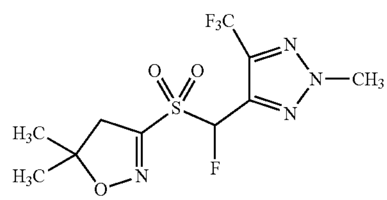
II.4

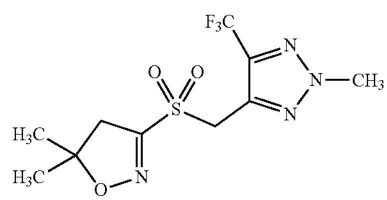
II.5

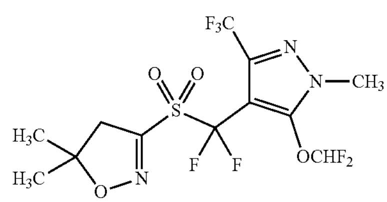
II.6

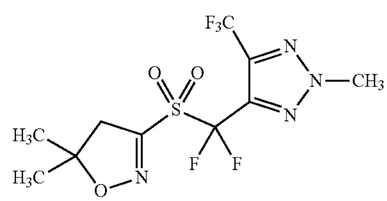
II.7

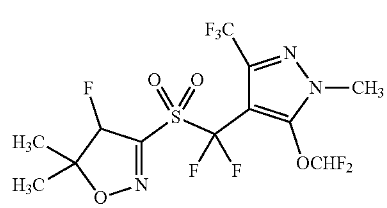
II.8

-continued

II.9

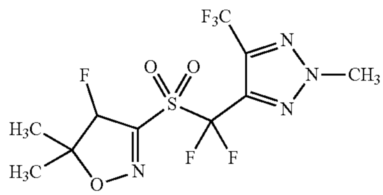

the isoxazoline compounds of the formula (II) are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors:

chlorthiamid, dichlobenil, flupoxam, indaziflam, isoxaben, triaziflam and 1-cyclohexyl-5-pentafluorphenyloxy-$1^4$-[1,2,4,6]thiatriazin-3-ylamine (CAS 175899-01-1);

b12) from the group of the decoupler herbicides:

dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6); b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin, methyl azide, methyl bromide, methyldymron, methyl iodide, MSMA, oleic acid, oxaziclomefone, pelargonic acid, pyributicarb, quinoclamine tetflupyrolimet, and tridiphane.

Moreover, it may be useful to apply the compounds of formula (I) in combination with safeners. Safeners are chemical compounds which prevent or reduce damage on useful plants without having a major impact on the herbicidal action of the compounds of the formula (I) towards undesired vegetation. They can be applied either before sowings (e.g. on seed treatments, shoots or seedlings) or in the pre-emergence application or post-emergence application of the useful plant. The safeners and the compounds of formula (I) and optionally the herbicides B can be applied simultaneously or in succession.

In another embodiment of the present invention the combinations according to the present invention comprise at least one compound of formula (I) and at least one safener C (component C).

Examples of safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alphaoximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of safener compounds C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4), metcamifen and BPCMS (CAS 54091-06-4).

The active compounds B of groups b1) to b15) and the active compounds C are known herbicides and safeners, see, for example, The Compendium of Pesticide Common Names; Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro [4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

The invention also relates to formulations comprising at least an auxiliary and at least one compound of formula (I) according to the invention.

A formulation comprises a pesticidally effective amount of a compound of formula (I). The term "effective amount" denotes an amount of the combination or of the compound of formula (I), which is sufficient for controlling undesired vegetation, especially for controlling undesired vegetation in crops (i.e. cultivated plants) and which does not result in a substantial damage to the treated crop plants. Such an amount can vary in a broad range and is dependent on various factors, such as the undesired vegetation to be controlled, the treated crop plants or material, the climatic conditions and the specific compound of formula (I) used.

The compounds of formula (I), their salts, amides, esters or thioesters can be converted into customary types of formulations, e. g. solutions, emulsions, suspensions, dusts, powders, pastes, granules, pressings, capsules, and mixtures thereof. Examples for formulation types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g.

WG, SG, GR, FG, GG, MG), insecticidal articles (e.g. LN), as well as gel formulations for the treatment of plant propagation materials such as seeds (e.g. GF). These and further formulation types are defined in the "Catalogue of pesticide formulation types and international coding system", Technical Monograph No. 2, $6^{th}$ Ed. May 2008, CropLife International.

The formulations are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetting agents, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of formula (I) on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for formulation types and their preparation are:

i) Water-Soluble Concentrates (SL, LS)

10-60 wt % of a compound of formula (I) or a combination comprising at least one compound of formula (I) (component A) and at least one further compound selected from the herbicidal compounds B (component B) and safeners C (component C) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a compound of formula (I) or a combination comprising at least one compound of formula (I) (component A) and at least one further compound selected from the herbicidal compounds B (component B) and safeners C (component C) according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of compound of formula (I) or a combination comprising at least one compound of formula (I) (component A) and at least one further compound selected from the herbicidal compounds B (component B) and safeners C (component C) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of compound of formula (I) or a combination comprising at least one compound of formula (I) (component A) and at least one further compound selected from the herbicidal compounds B (component B) and safeners C (component C) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound of formula (I) or a combination comprising at least one compound of formula (I) (component A) and at least one further compound selected from the herbicidal compounds B (component B) and safeners C (component C) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type formulation up to 40 wt % binder (e.g. polyvinylalcohol) is added.

vi) Water-Dispersible Granules and Water-Soluble Granules (WG, SG)

50-80 wt % of a compound of formula (I) or a combination comprising at least one compound of formula (I) (component A) and at least one further compound selected from the herbicidal compounds B (component B) and safeners C (component C) according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound of formula (I) or a combination comprising at least one compound of formula (I) (component A) and at least one further compound selected from the herbicidal compounds B (component B) and safeners C (component C) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound of formula (I) or a combination comprising at least one compound of formula (I) (component A) and at least one further compound selected from the herbicidal compounds B (component B) and safeners C (component C) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a compound of formula (I) or a combination comprising at least one compound of formula (I) (component A) and at least one further compound selected from the herbicidal compounds B (component B) and safeners C (component C) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a compound of formula (I) or a combination comprising at least one compound of formula (I) (component A) and at least one further compound selected from the herbicidal compounds B (component B) and safeners C (component C) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound of formula (I) according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS formulation.

ix) Dustable Powders (DP, DS)

1-10 wt % of a compound of formula (I) or a combination comprising at least one compound of formula (I) (component A) and at least one further compound selected from the herbicidal compounds B (component B) and safeners C (component C) according to the invention are ground finely and mixed intimately with solid carrier (e.g. finely divided kaolin) ad 100 wt %.

x) Granules (GR, FG)

0.5-30 wt % of a compound of formula (I) or a combination comprising at least one compound of formula (I) (component A) and at least one further compound selected from the herbicidal compounds B (component B) and safeners C (component C) according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of a compound of formula (I) or a combination comprising at least one compound of formula (I) (component A) and at least one further compound selected from the herbicidal compounds B (component B) and safeners C (component C) according to the invention are dissolved in organic solvent (e.g. aromatic hydrocarbon) ad 100 wt %.

The formulation types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The formulations and/or combinations generally comprise between 0.01 and 95%, preferably between 0.1 and 90%, and in particular between 0.5 and 75%, by weight of the compounds of formula (I).

The compounds of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The formulations in question give, after two-to-tenfold dilution, active substance concentrations of from 0.01 to 60% by weight, preferably from 0.1 to 40% by weight, in the ready-to-use preparations. (nach unten verschoben)

Methods for applying compounds of formula (I), formulations and/or combinations thereof, on to plant propagation material, especially seeds, include dressing, coating, pelleting, dusting, soaking and in-furrow application methods of the propagation material. Preferably, compounds of formula (I), formulations and/or combinations thereof, respectively, are applied on to the plant propagation material by a method such that germination is not induced, e. g. by seed dressing, pelleting, coating and dusting.

Various types of oils, wetting agents, adjuvants, fertilizer, or micronutrients, and further pesticides (e.g. herbicides, insecticides, fungicides, growth regulators, safeners) may be added to the compounds of formula (I), the formulations and/or the combinations comprising them as premix or, if appropriate not until immediately prior to use (tank mix). These agents can be admixed with the formulations according to the invention in a weight ratio of 1:100 to 100:1, preferably 1:10 to 10:1.

The user applies the compounds of formula (I) according to the invention, the formulations and/or the combinations comprising them usually from a pre-dosage device, a knapsack sprayer, a spray tank, a spray plane, or an irrigation system. Usually, the formulation is made up with water, buffer, and/or further auxiliaries to the desired application concentration and the ready-to-use spray liquor or the formulation according to the invention is thus obtained. Usually, 20 to 2000 liters, preferably 50 to 400 liters, of the ready-to-use spray liquor are applied per hectare of agricultural useful area.

According to one embodiment, either individual components of the formulation according to the invention or partially premixed components, e. g. components comprising compounds of formula (I) and optionally active substances from the groups B and/or C), may be mixed by the user in a spray tank and further auxiliaries and additives may be added, if appropriate.

In a further embodiment, individual components of the formulation according to the invention such as parts of a kit or parts of a binary or ternary mixture may be mixed by the user himself in a spray tank and further auxiliaries may be added, if appropriate.

In a further embodiment, either individual components of the formulation according to the invention or partially premixed components, e. g components comprising compounds of formula (I) and optionally active substances from the groups B and/or C), can be applied jointly (e.g. after tank mix) or consecutively.

The compounds of formula (I), are suitable as herbicides. They are suitable as such, as an appropriate formulation or in combination with at least one further compound selected from the herbicidal active compounds B (component B) and safeners C (component C).

The compounds of formula (I), or the formulations and/or combinations comprising the compounds of formula (I), control undesired vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

The compounds of formula (I), or the formulations and/or the combinations comprising them, are applied to the plants mainly by spraying the leaves. Here, the application can be carried out using, for example, water as carrier by customary spraying techniques using spray liquor amounts of from about 100 to 1000 l/ha (for example from 300 to 400 l/ha). The compounds of formula (I), or the formulations and/or the combinations comprising them, may also be applied by the low-volume or the ultra-low-volume method, or in the form of microgranules.

Application of the compounds of formula (I), or the formulations and/or the combinations comprising them, can be done before, during and/or after, preferably during and/or after, the emergence of the undesired vegetation.

Application of the compounds of formula (I), or the formulations and/or the combinations can be carried out before or during sowing.

The compounds of formula (I), or the formulations and/or the combinations comprising them, can be applied pre-, post-emergence or pre-plant, or together with the seed of a crop plant. It is also possible to apply the compounds of formula (I), or the formulations and/or the combinations comprising them, by applying seed, pretreated with the compounds of formula (I), or the formulations and/or the combinations comprising them, of a crop plant. If the active ingredients are less well tolerated by certain crop plants, application techniques may be used in which the combinations are sprayed, with the aid of the spraying equipment, in such a way that as far as possible they do not come into contact with the leaves of the sensitive crop plants, while the active ingredients reach the leaves of undesired vegetation growing underneath, or the bare soil surface (post-directed, lay-by).

In a further embodiment, the compounds of formula (I), or the formulations and/or the combinations comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the compounds of formula (I), or the formulations and/or the combinations prepared therefrom. Here, the combinations can be applied diluted or undiluted.

The term “seed” comprises seed of all types, such as, for example, corns, seeds, fruits, tubers, seedlings and similar forms. Here, preferably, the term seed describes corns and seeds.

The seed used can be seed of the crop plants mentioned above, but also the seed of transgenic plants or plants obtained by customary breeding methods.

When employed in plant protection, the amounts of active substances applied, i.e. the compounds of formula (I), component B and, if appropriate, component C without formulation auxiliaries, are, depending on the kind of effect desired, from 0.001 to 2 kg per ha, preferably from 0.005 to 2 kg per ha, more preferably from 0.05 to 0.9 kg per ha and in particular from 0.1 to 0.75 kg per ha.

In another embodiment of the invention, the application rate of the compounds of formula (I), component B and, if appropriate, component C, is from 0.001 to 3 kg/ha, preferably from 0.005 to 2.5 kg/ha and in particular from 0.01 to 2 kg/ha of active substance (a.s.).

In another preferred embodiment of the invention, the rates of application of the compounds of formula (I) according to the present invention (total amount of compounds of formula (I)) are from 0.1 g/ha to 3000 g/ha, preferably 10 g/ha to 1000 g/ha, depending on the control target, the season, the target plants and the growth stage.

In another preferred embodiment of the invention, the application rates of the compounds of formula (I) are in the range from 0.1 g/ha to 5000 g/ha and preferably in the range from 1 g/ha to 2500 g/ha or from 5 g/ha to 2000 g/ha.

In another preferred embodiment of the invention, the application rate of the compounds of formula (I) is 0.1 to 1000 g/ha, preferably 1 to 750 g/ha, more preferably 5 to 500 g/ha.

The required application rates of herbicidal compounds B are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of safeners C are generally in the range of from 0.0005 kg/ha to 2.5 kg/ha and preferably in the range of from 0.005 kg/ha to 2 kg/ha or 0.01 kg/ha to 1.5 kg/h of a.s.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. the compounds of formula (I), component B and, if appropriate, component C are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

In case of combinations according to the present invention it is immaterial whether the compounds of formula (I), and the further component B and/or the component C are formulated and applied jointly or separately.

In the case of separate application, it is of minor importance, in which order the application takes place. It is only necessary, that the compounds of formula (I), and the further component B and/or the component C are applied in a time frame that allows simultaneous action of the active ingredients on the plants, preferably within a time-frame of at most 14 days, in particular at most 7 days.

Depending on the application method in question, the compounds of formula (I), or the formulations and/or combinations comprising them, can additionally be employed in a further number of crop plants for eliminating undesired vegetation. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum*, (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*S. vulgare*), *Theobroma cacao, Trifolium pratense, Triticum aestivum, Triticale, Triticum durum, Vicia faba, Vitis vinifera* and *Zea mays*.

Preferred crops are *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum*, (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*s. vulgare*), *Triticale, Triticum aestivum, Triticum durum, Vicia faba, Vitis vinifera* and *Zea mays*.

Especially preferred crops are crops of cereals, corn, soybeans, rice, oilseed rape, cotton, potatoes, peanuts or permanent crops.

The compounds of formula (I) according to the invention, or the formulations and/or combinations comprising them, can also be used in crops which have been modified by mutagenesis or genetic engineering in order to provide a new trait to a plant or to modify an already present trait.

The term "crops" as used herein includes also (crop) plants which have been modified by mutagenesis or genetic engineering in order to provide a new trait to a plant or to modify an already present trait.

Mutagenesis includes techniques of random mutagenesis using X-rays or mutagenic chemicals, but also techniques of targeted mutagenesis, in order to create mutations at a specific locus of a plant genome. Targeted mutagenesis techniques frequently use oligonucleotides or proteins like CRISPR/Cas, zinc-finger nucleases, TALENs or meganucleases to achieve the targeting effect.

Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant in order to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name. Traits which have been introduced in plants or have been modified include in particular herbicide tolerance, insect resistance, increased yield and tolerance to abiotic conditions, like drought.

Herbicide tolerance has been created by using mutagenesis as well as using genetic engineering. Plants which have been rendered tolerant to acetolactate synthase (ALS) inhibitor herbicides by conventional methods of mutagenesis and breeding comprise plant varieties commercially available under the name Clearfield®. However, most of the herbicide tolerance traits have been created via the use of transgenes.

Herbicide tolerance has been created to glyphosate, glufosinate, 2,4-D, dicamba, oxynil herbicides, like bromoxynil and ioxynil, sulfonylurea herbicides, ALS inhibitor herbicides and 4-hydroxyphenylpyruvate dioxygenase (HPPD) inhibitors, like isoxaflutole and mesotrione.

Transgenes which have been used to provide herbicide tolerance traits comprise: for tolerance to glyphosate: cp4 epsps, epsps grg23ace5, mepsps, 2mepsps, gat4601, gat4621 and goxv247, for tolerance to glufosinate: pat and bar, for tolerance to 2,4-D: aad-1 and aad-12, for tolerance to dicamba: dmo, for tolerance to oxynil herbicies: bxn, for tolerance to sulfonylurea herbicides: zm-hra, csr1-2, gm-hra, S4-HrA, for tolerance to ALS inhibitor herbicides: csr1-2, for tolerance to HPPD inhibitor herbicides: hppdPF, W336 and avhppd-03.

Transgenic corn events comprising herbicide tolerance genes are for example, but not excluding others, DAS40278, MON801, MON802, MON809, MON810, MON832, MON87411, MON87419, MON87427, MON88017, MON89034, NK603, GA21, MZHGOJG, HCEM485, VCO01981-5, 676, 678, 680, 33121, 4114, 59122, 98140, Bt10, Bt176, CBH-351, DBT418, DLL25, MS3, MS6, MZIR098, T25, TC1507 and TC6275.

Transgenic soybean events comprising herbicide tolerance genes are for example, but not excluding others, GTS 40-3-2, MON87705, MON87708, MON87712, MON87769, MON89788, A2704-12, A2704-21, A5547-127, A5547-35, DP356043, DAS44406-6, DAS68416-4, DAS81419-2, GU262, SYHTOH2, W62, W98, FG72 and CV127.

Transgenic cotton events comprising herbicide tolerance genes are for example, but not excluding others, 19-51a, 31707, 42317, 81910, 281-24-236, 3006-210-23, BXN10211, BXN10215, BXN10222, BXN10224, MON1445, MON1698, MON88701, MON88913, GH1B119, GHB614, LLCotton25, T303-3 and T304-40.

Transgenic canola events comprising herbicide tolerance genes are for example, but not excluding others, MON88302, HCR-1, HCN10, HCN28, HCN92, MS1, MS8, PHY14, PHY23, PHY35, PHY36, RF1, RF2 and RF3.

Insect resistance has mainly been created by transferring bacterial genes for insecticidal proteins to plants. Transgenes which have most frequently been used are toxin genes of *Bacillus* spec. and synthetic variants thereof, like cry1A, cry1Ab, cry1Ab-Ac, cry1Ac, cry1A.105, cry1F, cry1Fa2, cry2Ab2, cry2Ae, mcry3A, ecry3.1Ab, cry3Bb1, cry34Ab1, cry35Ab1, cry9C, vip3A(a), vip3Aa20. However, also genes of plant origin have been transferred to other plants. In particular genes coding for protease inhibitors, like CpTI and pinII. A further approach uses transgenes in order to produce double stranded RNA in plants to target and downregulate insect genes. An example for such a transgene is dvsnf7.

Transgenic corn events comprising genes for insecticidal proteins or double stranded RNA are for example, but not excluding others, Bt10, Bt11, Bt176, MON801, MON802, MON809, MON810, MON863, MON87411, MON88017, MON89034, 33121, 4114, 5307, 59122, TC1507, TC6275, CBH-351, MIR162, DBT418 and MZIR098.

Transgenic soybean events comprising genes for insecticidal proteins are for example, but not excluding others, MON87701, MON87751 and DAS-81419.

Transgenic cotton events comprising genes for insecticidal proteins are for example, but not excluding others, SGK321, MON531, MON757, MON1076, MON15985, 31707, 31803, 31807, 31808, 42317, BNLA-601, Event1, COT67B, COT102, T303-3, T304-40, GFM Cry1A, GK12, MLS 9124, 281-24-236, 3006-210-23, GHB119 and SGK321.

Increased yield has been created by increasing ear biomass using the transgene athb17, being present in corn event MON87403, or by enhancing photosynthesis using the transgene bbx32, being present in the soybean event MON87712.

Crops comprising a modified oil content have been created by using the transgenes: gm-fad2-1, Pj.D6D, Nc.Fad3, fad2-1A and fatb1-A. Soybean events comprising at least one of these genes are: 260-05, MON87705 and MON87769.

Tolerance to abiotic conditions, in particular to tolerance to drought, has been created by using the transgene cspB, comprised by the corn event MON87460 and by using the transgene Hahb-4, comprised by soybean event IND-00410-5.

Traits are frequently combined by combining genes in a transformation event or by combining different events during the breeding process. Preferred combination of traits are herbicide tolerance to different groups of herbicides, insect tolerance to different kind of insects, in particular tolerance to lepidopteran and coleopteran insects, herbicide tolerance with one or several types of insect resistance, herbicide tolerance with increased yield as well as a combination of herbicide tolerance and tolerance to abiotic conditions.

Plants comprising singular or stacked traits as well as the genes and events providing these traits are well known in the art. For example, detailed information as to the mutagenized or integrated genes and the respective events are available from websites of the organizations "International Service for the Acquisition of Agri-biotech Applications (ISAAA)" and the "Center for Environmental Risk Assessment (CERA)", as well as in patent applications, like EP3028573 and WO2017/011288.

The use of the compounds of formula (I) or formulations or combinations comprising them according to the invention on crops may result in effects which are specific to a crop comprising a certain gene or event. These effects might involve changes in growth behavior or changed resistance to biotic or abiotic stress factors. Such effects may in particular comprise enhanced yield, enhanced resistance or tolerance to insects, nematodes, fungal, bacterial, *mycoplasma*, viral or viroid pathogens as well as early vigor, early or delayed ripening, cold or heat tolerance as well as changed amino acid or fatty acid spectrum or content.

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the compounds of formula (I) according to the invention, or the formulations and/or combinations comprising them, are also suitable for the defoliation and/or desiccation of plant parts of crops such as cotton, potato, oilseed rape, sunflower, soybean or field beans, in particular cotton. In this regard, formulations and/or combinations for the desiccation and/or defoliation of crops, processes for preparing these formulations and/or combinations and methods for desiccating and/or defoliating plants using the compounds of formula (I) have been found.

As desiccants, the compounds of formula (I) are particularly suitable for desiccating the aboveground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

A CHEMISTRY EXAMPLES

Chemical bonds, drawn as bars in chemical formulae, indicate the relative stereochemistry on the ring system.

EXAMPLES

Example 1: Synthesis of methyl (3S)-3-[[3-(3,5-dichlorophenyl)-5-(trifluoromethyl)-1,4,2-dioxazole-5-carbonyl]amino]butanoate (Cpd. 13)

Step 1

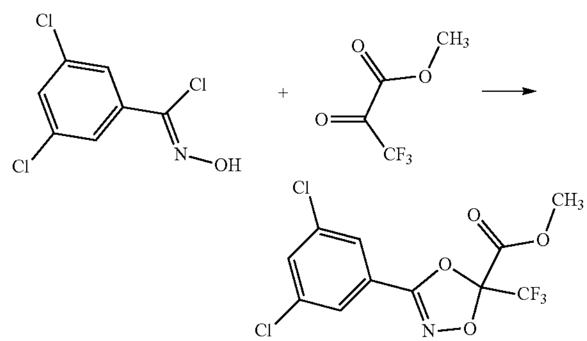

To a mixture of (1Z)-3,5-dichloro-N-hydroxy-benzimidoyl chloride (CAS 677727-73-0; 3 g, 13.33 mmol) in toluene (50 ml) and methyl 3,3,3-trifluoro-2-oxo-propanoate (10.4 g, 66.66 mmol) was added triethylamine (1.36 g, 13.33 mmol) in toluene (20 ml) dropwise at 25° C. and the mixture was stirred at 25° C. for 5 hours. The mixture was poured into water and extracted with ethylacetate. The combined organic layers were washed with brine, dried and concentrated. The crude material was purified by column chromatography (petrolether:ethylacetate=100:1 to 10:1) to give methyl 3-(3,5-dichlorophenyl)-5-(trifluoromethyl)-1,4,2-dioxazole-5-carboxylate (3.6 g, 82%) as yellow oil.

$^1$H NMR (400 MHz, CDCl3): δ 7.73 (d, J=1.88 Hz, 2H) 7.57 (t, J=1.82 Hz, 1H) 3.99 (s, 3H)

Step 2

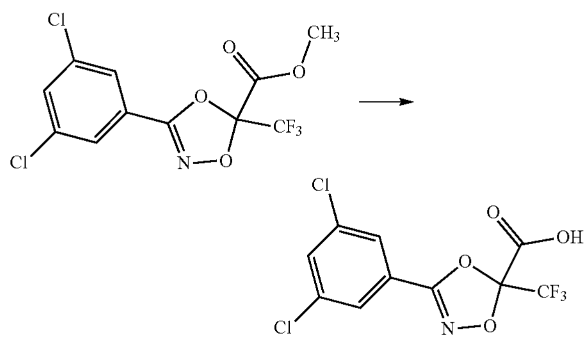

To a mixture of methyl 3-(3,5-dichlorophenyl)-5-(trifluoromethyl)-1,4,2-dioxazole-5-carboxylate (1 g, 3.31 mmol) in THF/$H_2O$ (12 ml/4 ml) was added lithium hydroxide (278 mg, 6.62 mmol) at 25° C. and the mixture was stirred at 25° C. for 2 hours. The mixture was poured into water, the pH adjusted to pH=3, and extracted with ethyl acetate. The combined organic layers were washed with brine, dried and concentrated. Purification by preparative HPLC (trifluoroacetic acid, acetonitrile-water) yielded 3-(3,5-dichlorophenyl)-5-(trifluoromethyl)-1,4,2-dioxazole-5-carboxylic acid (700 mg, 64%) as white solid. $^1$H NMR (400 MHz, CDCl3): δ 7.94 (t, J=1.82 Hz, 1H) 7.73 (d, J=1.88 Hz, 2H)

Step 3

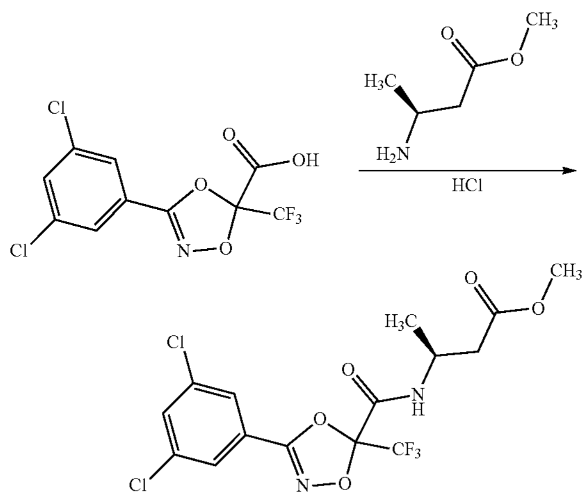

To a mixture of 3-(3,5-dichlorophenyl)-5-(trifluoromethyl)-1,4,2-dioxazole-5-carboxylic acid (1.1 g, 3.37 mmol) in dichloromethane (20 ml) was added dimethylformamide (1 drop) and $(COCl)_2$ (641.35 mg, 5.05 mmol) at 25° C. The mixture was stirred at 25° C. for 1 hour. The mixture was concentrated, dissolved in dichloromethane (5 mL) and added to methyl (3S)-3-aminobutanoate hydrochloride (834 mg, 5.05 mmol) in pyridine (22 ml) at 0° C. dropwise. The resulting mixture was stirred at 25° C. for 2 hours. The mixture was poured into water and extracted with ethylacetate. The combined organics were washed with brine, dried and concentrated. Purification by preparative HPLC (trifluoroacetic acid, acetonitrile-water) yielded methyl (3S)-3-[[3-(3,5-dichlorophenyl)-5-(trifluoromethyl)-1,4,2-dioxazole-5-carbonyl]amino]butanoate (130 mg, 9%) as white solid. $^1$H NMR (400 MHz, CDCl3): δ 7.75 (t, J=1.7 Hz, 2H), 7.57 (s, 1H), 7.52-7.40 (m, 1H), 4.49-4.34 (m, 1H), 3.75-3.69 (m, 3H), 2.69-2.53 (m, 2H), 1.35-1.30 (in, 3H)

High Performance Liquid Chromatography: HPLC-column Kinetex XB C18 1.7μ (50×2.1 mm); eluent: acetonitrile/water+0.1% trifluoroacetic acid (gradient from 5:95 to 100:0 in 1.5 min at 60° C., flow gradient from 0.8 to 1.0 ml/min in 1.5 min).

In analogy to the examples described above, the following compounds of formula (I), wherein $R^1$ is hydrogen, were prepared, starting from commercially available diesters and using commercially available amines:

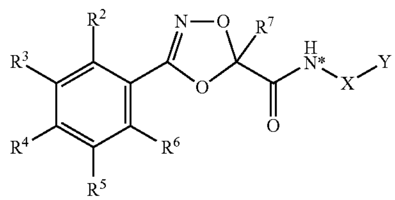

TABLE 2

| Cpd. | $R^2$ | $R^3$ | $R^4$ | $R^5$ | $R^6$ | $R^7$ | N*-X-Y | HPLC/MS |
|---|---|---|---|---|---|---|---|---|
| I1 | H | Cl | H | Cl | H | $CH_3$ | 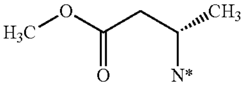 | 374.8 |
| I2 | H | Cl | H | Cl | H | $CH_3$ | 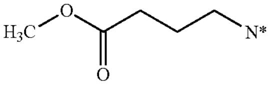 | 374.9 |
| I3 | H | Cl | H | Cl | H | $CF_3$ | 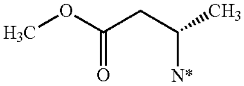 | 428.7 |
| I4 | H | F | H | F | H | $CH_3$ | 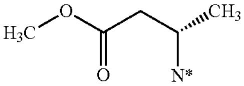 | 342.9 |
| I5 | H | F | H | F | H | $CH_3$ | 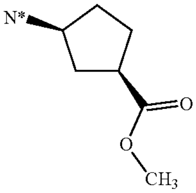 | 369.0 |
| I6 | H | F | H | F | H | $CH_3$ | 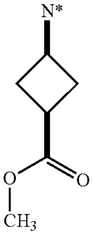 | 354.8 |
| I7 | H | Cl | H | Cl | H | $CH_3$ | 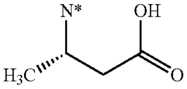 | 360.9 |

TABLE 2-continued

| Cpd. | $R^2$ | $R^3$ | $R^4$ | $R^5$ | $R^6$ | $R^7$ | N*-X-Y | HPLC/MS |
|---|---|---|---|---|---|---|---|---|
| I8 | H | F | H | F | H | $CH_3$ | 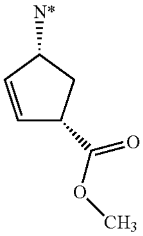 | 366.8 |
| I9 | H | Cl | H | Cl | H | $CF_3$ | 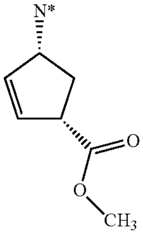 | 452.9 |
| I10 | H | Cl | H | Cl | H | $CHCH_2$ | 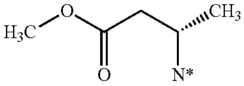 | 387.0 |
| I11 | H | Cl | H | Cl | H | $CHCH_2$ | 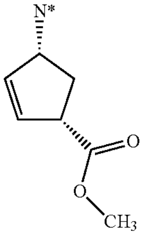 | 410.8 |
| I12 | H | Cl | H | Cl | H | $OCH_2CH_3$ | 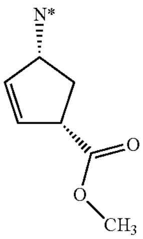 | |
| I13 | H | Cl | H | Cl | H | $OCH_3$ | 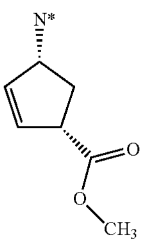 | |

HPLC/MS = MassChargeRatio

B USE EXAMPLES

The herbicidal activity of the compounds of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the test plants had rooted. This cover caused uniform germination of the test plants, unless this had been impaired by the active ingredients. For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the test plants were kept at 10-25° C. or 20-35° C., respectively. The test period extended over 2 to 4 weeks. During this time, the test plants were tended, and their response to the individual treatments was evaluated.

Evaluation was carried out using a scale from 0 to 100. 100 means no emergence of the test plants, or complete destruction of at least the aerial moieties, and 0 means no damage, or normal course of growth. A good herbicidal activity is given at values of 80 to 90 and a very good herbicidal activity is given at values of 90 to 100.

The test plants used in the greenhouse experiments were of the following species:

| Bayer code | Scientific name |
|---|---|
| ALOMY | *Alopercurus myosuroides* |
| AMARE | *Amaranthus retroflexus* |
| APESV | *Apera spica-venti* |
| AVEFA | *Avena fatua* |
| ECHCG | *Echinocloa crus-galli* |
| SETFA | *Setaria faberi* |
| SETVI | *Setaria viridis* |

At an application rate of 1,000 kg/ha, applied by the pre-emergence method:

- compounds 17, 18, 110 showed very good herbicidal activity against APESV.
- compound 18 showed very good herbicidal activity against AMARE.
- compound 110 showed good herbicidal activity against AMARE.
- compounds 18, 110 showed very good herbicidal activity against ECHCG.
- compound 17 showed good herbicidal activity against ECHCG.
- compound 17 showed very good herbicidal activity against SETFA.

At an application rate of 0,500 kg/ha, applied by the pre-emergence method:

- compound 13, showed very good herbicidal activity against AMARE.
- compound 12 showed good herbicidal activity against APESV.
- compounds 11, 13, 14, 15, 16 showed very good herbicidal activity against APESV.
- compounds 11, 14, 15, 16 showed very good herbicidal activity against ECHCG.

At an application rate of 0,250 kg/ha, applied by the pre-emergence method:

- compounds 19, 111 showed very good herbicidal activity against APESV.
- compounds 19, 111 showed good herbicidal activity against AMARE.
- compound 111 showed very good herbicidal activity against ECHCG.

At an application rate of 1,000 kg/ha, applied by the post-emergence method:

- compounds 17, 18, 110 showed very good herbicidal activity against ECHCG.
- compounds 17, 18 showed very good herbicidal activity against AMARE.
- compound 110 showed good herbicidal activity against AMARE.
- compounds 17, 18, 110 showed very good herbicidal activity against SETVI.

At an application rate of 0,500 kg/ha, applied by the post-emergence method:

- compounds 11, 12, 14, 15, 16 showed very good herbicidal activity against ALOMY.
- compound 13 showed good herbicidal activity against ALOMY.
- compounds 13, 14, 15, 16 showed very good herbicidal activity against AVEFA.
- compound 12 showed good herbicidal activity against AVEFA.
- compound 11 showed very good herbicidal activity against ECHCG.
- compound 16 showed very good herbicidal activity against SETVI.
- compounds 11, 12, 13, 14, 15 showed good herbicidal activity against SETVI.

At an application rate of 0,250 kg/ha, applied by the post-emergence method:

- compounds 19, 111 showed very good herbicidal activity against ALOMY.
- compound 19 showed very good herbicidal activity against AVEFA.
- compound 111 showed very good herbicidal activity against ECHCG.
- compounds 19, 111 showed very good herbicidal activity against SETVI.

The invention claimed is:

1. A compound of formula (I)

(I)

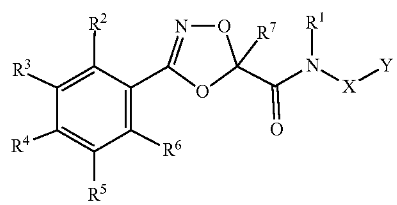

wherein the substituents have the following meanings:

$R^1$ is hydrogen;
$R^2$ is hydrogen;
$R^3$ is halogen;
$R^4$ is hydrogen;
$R^5$ is halogen;
$R^6$ is hydrogen;
$R^7$ is $(C_1-C_2)$-alkyl, cyclopropyl, $(C_1-C_2)$-haloalkyl, or $(C_2-C_3)$-alkenyl;
X is a bond
Y is Z;
Z is a four- or five-membered saturated or partly unsaturated ring which is formed from r carbon atoms, and which is substituted by m radicals selected from the group consisting of $CO_2R^e$;
$R^e$ is hydrogen, or $(C_1-C_6)$-alkyl, $(C_3-C_6)$-cycloalkyl, $(C_2-C_4)$-alkenyl, phenyl-$(C_1-C_3)$-alkyl, or $(C_2-C_4)$-alkynyl, each of which is substituted by m radicals selected from the group consisting of fluorine, chlorine, bromine, cyano, and $(C_1-C_2)$-alkoxy;
m is 0, 1, 2, 3, 4, or 5;
r is 4 or 5.

2. The compound as claimed in claim 1, wherein the substituents have the following meaning:

Z is selected from the group consisting of cyclobutyl, cyclopentyl, and cyclopentenyl, each substituted by m radicals from the group consisting of $CO_2R^e$.

3. A composition comprising at least one compound as claimed in claim 1, and at least one auxiliary, which is customary for formulating crop protection compositions.

4. The composition as claimed in claim 3, further comprising a additional herbicide.

5. A method for controlling unwanted vegetation which comprises applying an herbicidally effective amount of at least one compound as claimed in claim 1 to the unwanted vegetation, its seed, and/or its habitat.

6. A compound of formula (I)

(I)

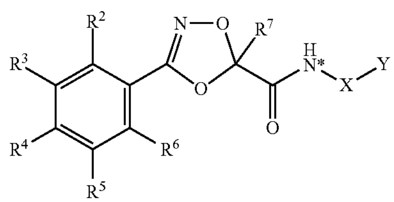

wherein the substituents have the following meanings:

$R^1$ is hydrogen;
$R^2$ is hydrogen;
$R^3$ is halogen;
$R^4$ is hydrogen;
$R^5$ is halogen;
$R^6$ is hydrogen;
$R^7$ is methyl, chloromethyl, trifluoromethyl, cyclopropyl, or ethenyl;
X is a bond;
Y is Z;
Z is selected from the group consisting of cyclobutyl, cyclopentyl, and cyclopentenyl, each substituted by m radicals from the group consisting of $CO_2R^e$;
$R^e$ is hydrogen or $(C_1-C_6)$-alkyl;
m is 0, 1, 2, 3, 4, or 5.

7. A composition comprising at least one compound as claimed in claim 6, and at least one auxiliary, which is customary for formulating crop protection compositions.

8. The composition as claimed in claim 7, further comprising an additional herbicide.

9. A method for controlling unwanted vegetation which comprises applying a herbicidally effective amount of at least one compound as claimed in claim 6 to act on the unwanted vegetation, plants, seeds thereof, and/or its habitat.

* * * * *